(12) United States Patent
Ledwith et al.

(10) Patent No.: US 12,117,797 B2
(45) Date of Patent: Oct. 15, 2024

(54) LIFT COMMUNICATIONS SYSTEMS COMPRISING WALL-MOUNTED DISPLAYS AND METHODS OF USING AND CONFIGURING THE SAME

(71) Applicant: LIKO RESEARCH & DEVELOPMENT AB, Luleå (SE)

(72) Inventors: James Ledwith, Syracuse, NY (US); Melissa R. Stancato, Syracuse, NY (US); Jesse Newman, Rochester, NY (US); Karin Olsson, Sodra Sunderbyn (SE); Daniel Johansson, Råneå (SE); Sheeza Hussain, Raleigh, NC (US); Scott M. Corbin, Sunman, IN (US); Sravan Mamidi, Columbus, IN (US); Todd P. O'Neal, Fairfield, OH (US); Joseph T. Canter, Harrison, OH (US); Jason M. Williams, Cary, NC (US); Gregory J. Shannon, Indianapolis, IN (US); Bryan Weidman, Columbus, IN (US)

(73) Assignee: LIKO RESEARCH & DEVELOPMENT AB, Luleå (SE)

( * ) Notice: Subject to any disclaimer, the term of this patent is extended or adjusted under 35 U.S.C. 154(b) by 1214 days.

(21) Appl. No.: 16/708,709

(22) Filed: Dec. 10, 2019

(65) Prior Publication Data

US 2020/0183362 A1    Jun. 11, 2020

Related U.S. Application Data

(60) Provisional application No. 62/857,002, filed on Jun. 4, 2019, provisional application No. 62/778,021, filed on Dec. 11, 2018.

(51) Int. Cl.
*G05B 19/4155* (2006.01)
*A61G 7/10* (2006.01)
(Continued)

(52) U.S. Cl.
CPC ....... *G05B 19/4155* (2013.01); *A61G 7/1017* (2013.01); *A61G 7/1042* (2013.01);
(Continued)

(58) Field of Classification Search
None
See application file for complete search history.

(56) References Cited

U.S. PATENT DOCUMENTS

| 5,699,038 A | 12/1997 | Ulrich et al. |
| 7,472,439 B2 | 1/2009 | Lemire et al. |

(Continued)

FOREIGN PATENT DOCUMENTS

| EP | 2684549 A2 | 1/2014 |
| EP | 2355766 B1 | 10/2015 |
| WO | 2018147476 A1 | 8/2018 |

OTHER PUBLICATIONS

Extended European Search Report for European Application No. 19214610.8 dated Sep. 17, 2020, 9 pages.

*Primary Examiner* — David Earl Ogg
(74) *Attorney, Agent, or Firm* — Dinsmore & Shohl LLP

(57) ABSTRACT

Lift communications systems, wall-mounted controls, and methods of using and configuring the same are disclosed. A lift communications system includes one or more lifts, each one of the one or more lifts is movable within a space. The lift communications system further includes a wall-mounted control coupled to a wall of the space. The wall-mounted control is configured to communicatively couple to the one or more lifts via a wireless connection. When the wall-mounted control is communicatively coupled to a lift of the one or more lifts, the wall-mounted control is configured to direct operation of the lift and receive data from the lift.

20 Claims, 25 Drawing Sheets

(51) Int. Cl.
   *G05B 19/414* (2006.01)
   *G06F 3/14* (2006.01)
   *H04L 41/22* (2022.01)
   *H04L 61/5014* (2022.01)
   *H04W 76/10* (2018.01)

(52) U.S. Cl.
   CPC ......... *A61G 7/1048* (2013.01); *G05B 19/414* (2013.01); *G06F 3/14* (2013.01); *H04L 41/22* (2013.01); *H04L 61/5014* (2022.05); *H04W 76/10* (2018.02); *A61G 2203/12* (2013.01); *A61G 2203/20* (2013.01); *A61G 2203/44* (2013.01); *G05B 2219/45014* (2013.01)

(56) References Cited

U.S. PATENT DOCUMENTS

| | | | |
|---|---|---|---|
| 8,085,146 B2 | 12/2011 | Rees | |
| 8,334,777 B2 | 12/2012 | Wilson et al. | |
| 8,538,710 B2 | 9/2013 | Todd et al. | |
| 8,789,222 B2 | 7/2014 | Blanchard et al. | |
| 9,125,630 B2 | 9/2015 | Menzel | |
| 9,408,765 B2 | 8/2016 | Andersson et al. | |
| 9,492,341 B2 | 11/2016 | Huster et al. | |
| 9,517,034 B2 | 12/2016 | Collings, Jr. et al. | |
| 9,561,147 B2 | 2/2017 | Todd et al. | |
| 9,661,119 B2 | 5/2017 | Mankopf et al. | |
| 9,833,194 B2 | 12/2017 | Hayes et al. | |
| 10,068,461 B2 | 9/2018 | Wildman et al. | |
| 10,124,997 B2 | 11/2018 | Jaipaul | |
| 2008/0143280 A1 | 6/2008 | Rock | |
| 2010/0224841 A1 | 9/2010 | Liljedahl | |
| 2010/0293611 A1 | 11/2010 | Ablabutyan | |
| 2012/0068832 A1* | 3/2012 | Feldstein | G06F 1/1632 340/12.5 |
| 2012/0198613 A1* | 8/2012 | Jelinek | A61G 7/015 5/86.1 |
| 2013/0076517 A1 | 3/2013 | Penninger et al. | |
| 2014/0013503 A1* | 1/2014 | Dixon | A61G 7/1017 5/85.1 |
| 2014/0020175 A1* | 1/2014 | Dixon | A61G 7/1051 5/85.1 |
| 2014/0297327 A1* | 10/2014 | Heil | G16H 40/40 700/282 |
| 2015/0033295 A1* | 1/2015 | Huster | G06F 21/44 726/4 |
| 2017/0000673 A1* | 1/2017 | Harmeyer | A61G 7/108 726/4 |
| 2017/0027796 A1* | 2/2017 | Kaikenger | A61G 7/1042 |
| 2017/0071807 A1* | 3/2017 | Liljedahl | A61G 7/10 |
| 2017/0323555 A1 | 11/2017 | Embree et al. | |
| 2018/0369039 A1 | 12/2018 | Bhimavarapu et al. | |

* cited by examiner

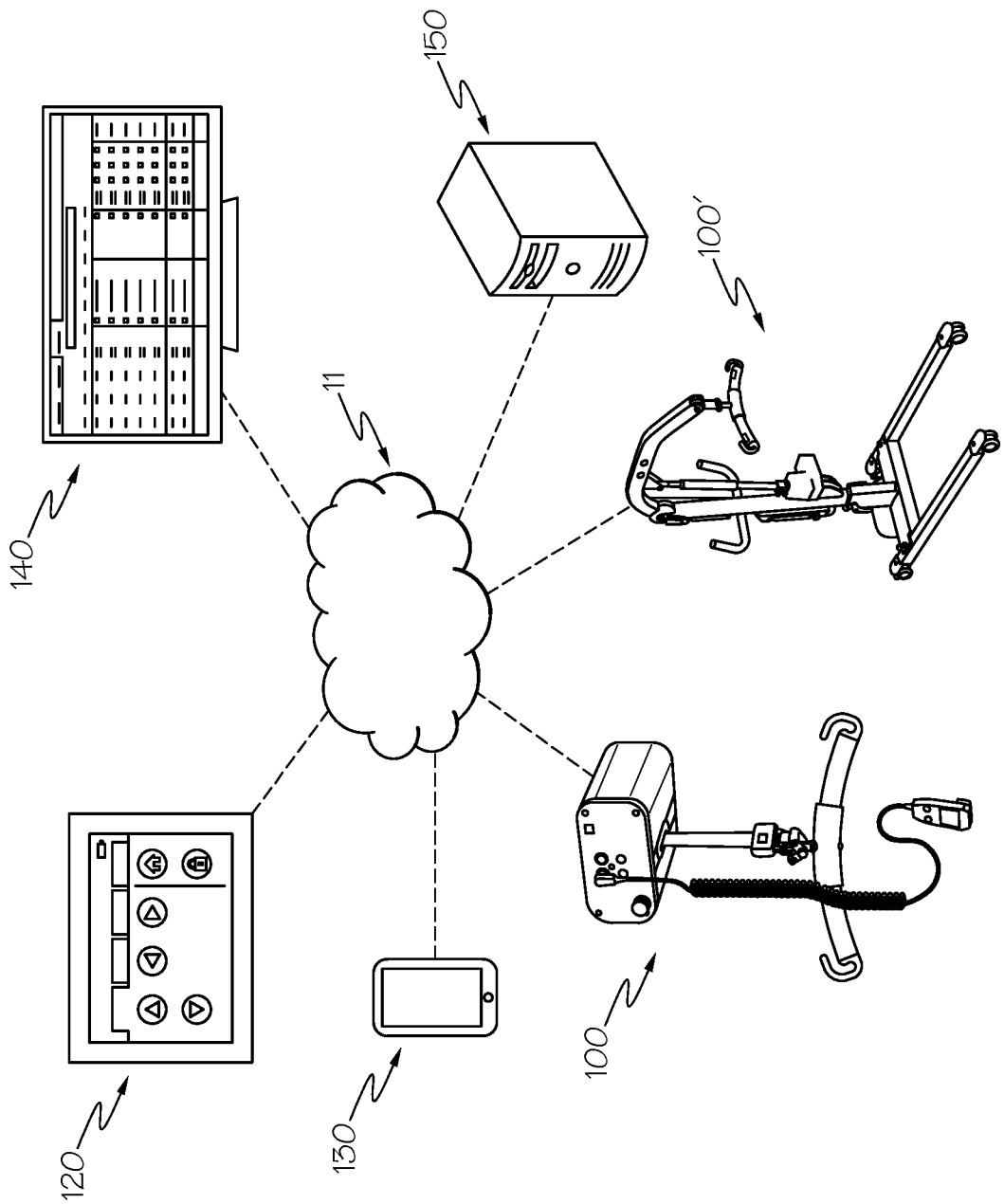

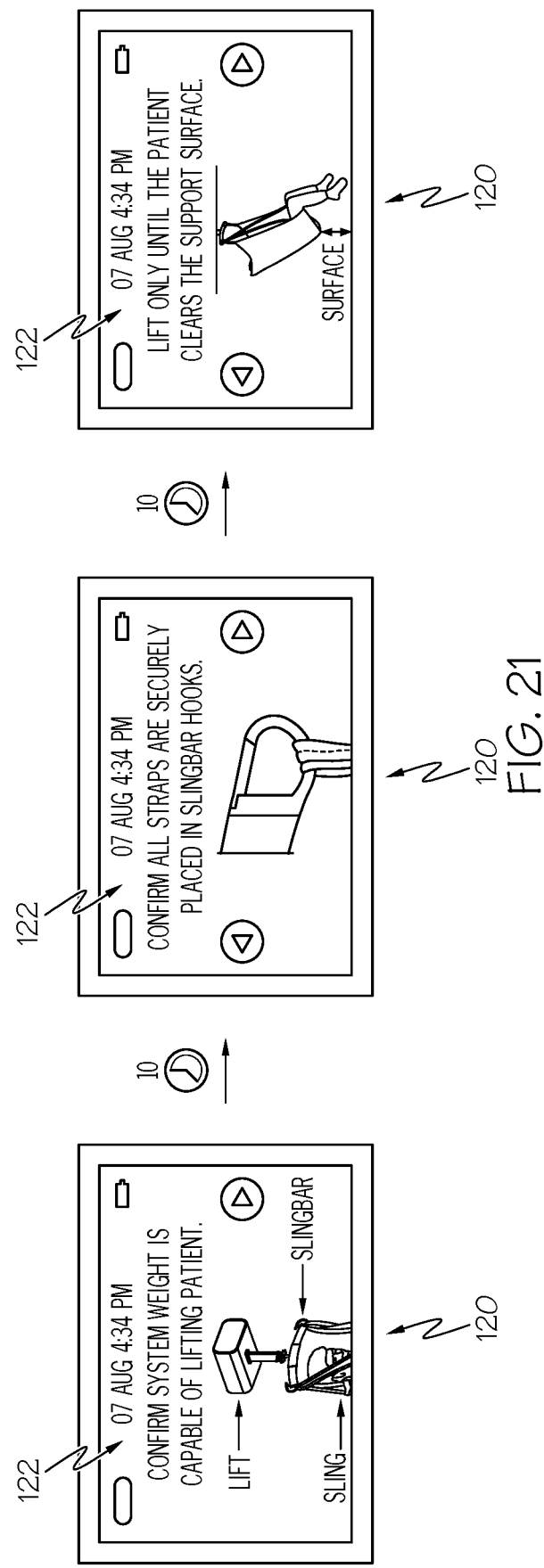

LIFT COMMUNICATIONS SYSTEMS COMPRISING WALL-MOUNTED DISPLAYS AND METHODS OF USING AND CONFIGURING THE SAME

CROSS-REFERENCE TO RELATED APPLICATION

The present application claims the priority benefit of U.S. Provisional Patent Application Ser. No. 62/778,021, filed Dec. 11, 2018 and entitled "RAIL-MOUNTED LIFTS WITH UNTETHERED, WALL MOUNTED CONTROLS" and U.S. Provisional Patent Application Ser. No. 62/857,002, filed Jun. 4, 2019 and entitled "SYSTEMS AND METHODS FOR UTILIZING DATA ASSOCIATED WITH RAIL-MOUNTED LIFT SYSTEMS FOR FEEDBACK, COMPLIANCE, AND LIFT CONTROL," the entire contents of each is incorporated herein by reference in their respective entireties.

BACKGROUND

Field

The present specification generally relates to rail-mounted lifts and, more specifically, to rail-mounted lifts having various components that are wirelessly coupled to the lift unit such that data is transmissible between the lift unit and the various components.

Technical Background

Current overhead lifts are operated entirely by a corded hand control. The cord is tethered to the overhead lift itself. The tethered operation offers plenty of challenges, including, but not limited to, the hand control and its attachment point (e.g., the sling bar) can only be stored at a reachable height, which creates an obstacle in the room during non-operation. In rooms with curtains or ceiling obstacles, the tethered remote provides a challenge to move the lift across the room while also holding onto the hand control. Caregivers have to swing the cord around object, which can become tangled at a height that may be unreachable to the caregiver. Further, current lifts generally do not offer connectivity to support devices, nor do they offer visual support for the caregiver beyond some LED light alerts or the like. Certain products may have a small screen on the corded hand control, but the screen offers very little benefit to caregivers because the screen is too small to provide any relevant and easily readable information.

Further, some overhead lifts are capable of generating data pertaining to use of the lift (e.g., to lift a subject out of a bed, to transfer a subject, to move paraplegic subjects, and/or the like), location of the lift, status of the lift (e.g., repair status, weight rating, and/or the like), information pertaining to subjects associated with the lift, information pertaining to a user or authorized group of users of the lift, and/or the like. However, such lifts do not include components for providing the data in a manner such that it is usable to provide a user with feedback, track compliance, ensure correct operation, and/or the like. In addition, overhead lifts do not offer connectivity to additional devices, nor do the overhead lifts offer an ability to display information pertaining to the generated and provided data.

SUMMARY

In an aspect, a lift communications system includes one or more lifts, each one of the one or more lifts is movable within a space. The lift communications system further includes a wall-mounted control coupled to a wall of the space. The wall-mounted control is configured to communicatively couple to the one or more lifts via a wireless connection. When the wall-mounted control is communicatively coupled to a lift of the one or more lifts, the wall-mounted control is configured to direct operation of the lift and receive data from the lift.

In another aspect, a lift communications system includes one or more lifts, each one of the one or more lifts is movable within a space. The lift communications system further includes a wall-mounted control coupled to a wall of the space, the wall-mounted control configured to communicatively couple to the one or more lifts via a wireless connection. When the wall-mounted control is communicatively coupled to a lift of the one or more lifts, the wall-mounted control is configured to direct operation of the lift. The lift communications system further includes a remote control communicatively coupled to the wall-mounted control. The remote control is programmed to selectively operate the wall-mounted control. The lift communications system further includes a remote display communicatively coupled to the wall-mounted control and the one or more lifts. The remote display provides information pertaining to operation of the one or more lifts. Data pertaining to the operation of the one or more lifts is generated by the one or more lifts and is transmitted to the wall-mounted control and the remote display.

In yet another aspect, a wall-mounted control coupled to a wall of a space includes network interface hardware, a processing device communicatively coupled to the network interface hardware, and a non-transitory, processor-readable storage medium communicatively coupled to the processing device. The non-transitory, processor-readable storage medium includes one or more programming instructions thereon that, when executed, cause the processing device to receive an input from a user via a network configuration interface, the input corresponding to network information for coupling the wall-mounted control to a network. The non-transitory, processor-readable storage medium further includes one or more programming instructions thereon that, when executed, cause the processing device to connect to a DHCP server via the network interface hardware using the network information and receive DHCP information from the DHCP server and communicatively couple to a lift via the network using the network interface hardware.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 10A schematically depicts an illustrative lift communications network according to one or more embodiments shown and described herein;

FIG. 21 schematically depicts a succession of screen shots of an instructions module user interface of a wall-mounted control that provides instructions for configuring one or more components of a lift according to one or more embodiments shown and described herein;

DETAILED DESCRIPTION

Figure 1A:
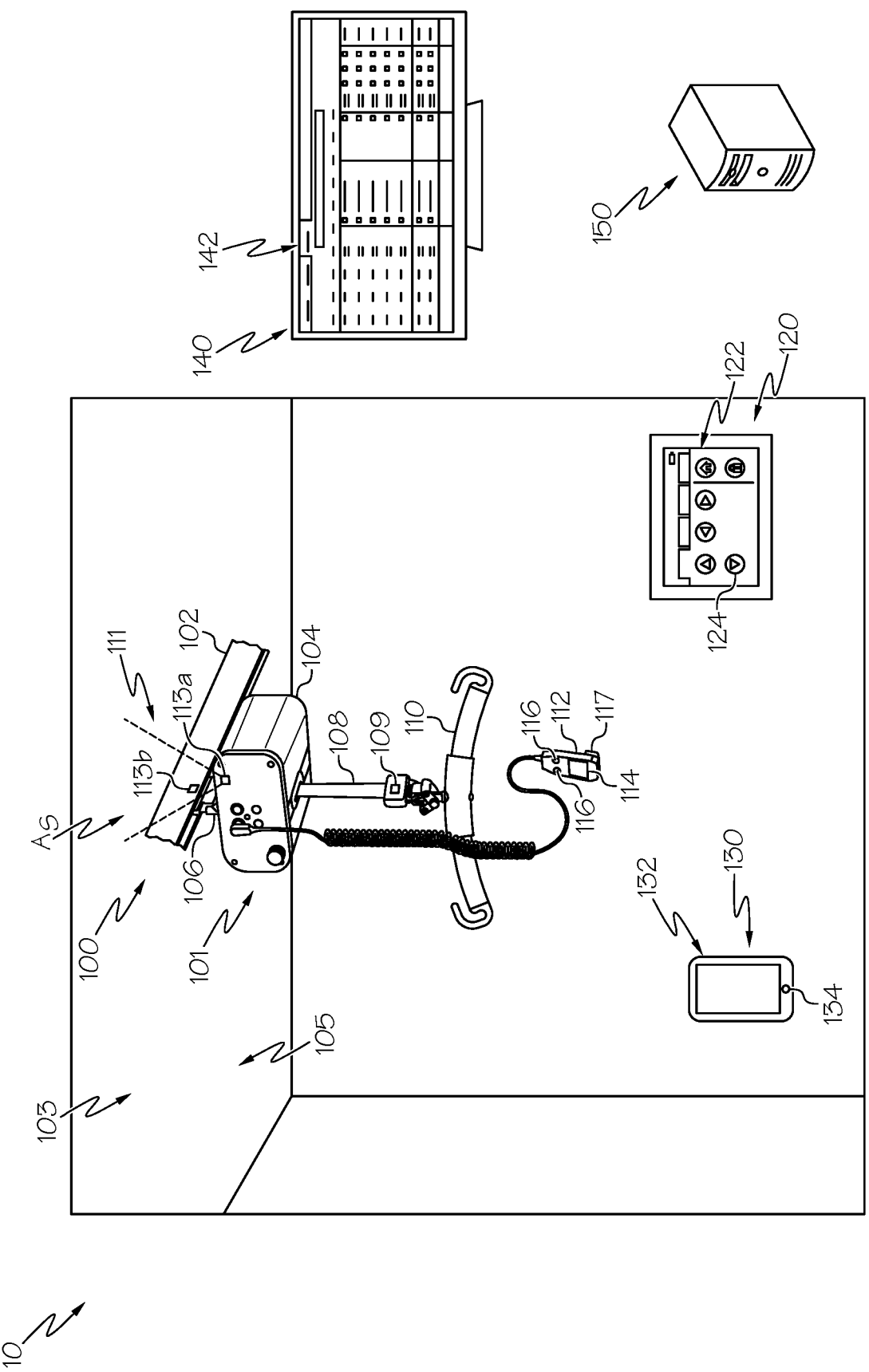
FIG. 1A schematically depicts an illustrative lift including a rail mounted lift unit, an untethered, wall-mounted control, a remote control, a remote display, and a server according to one or more embodiments shown and described herein.
Figure 1B:
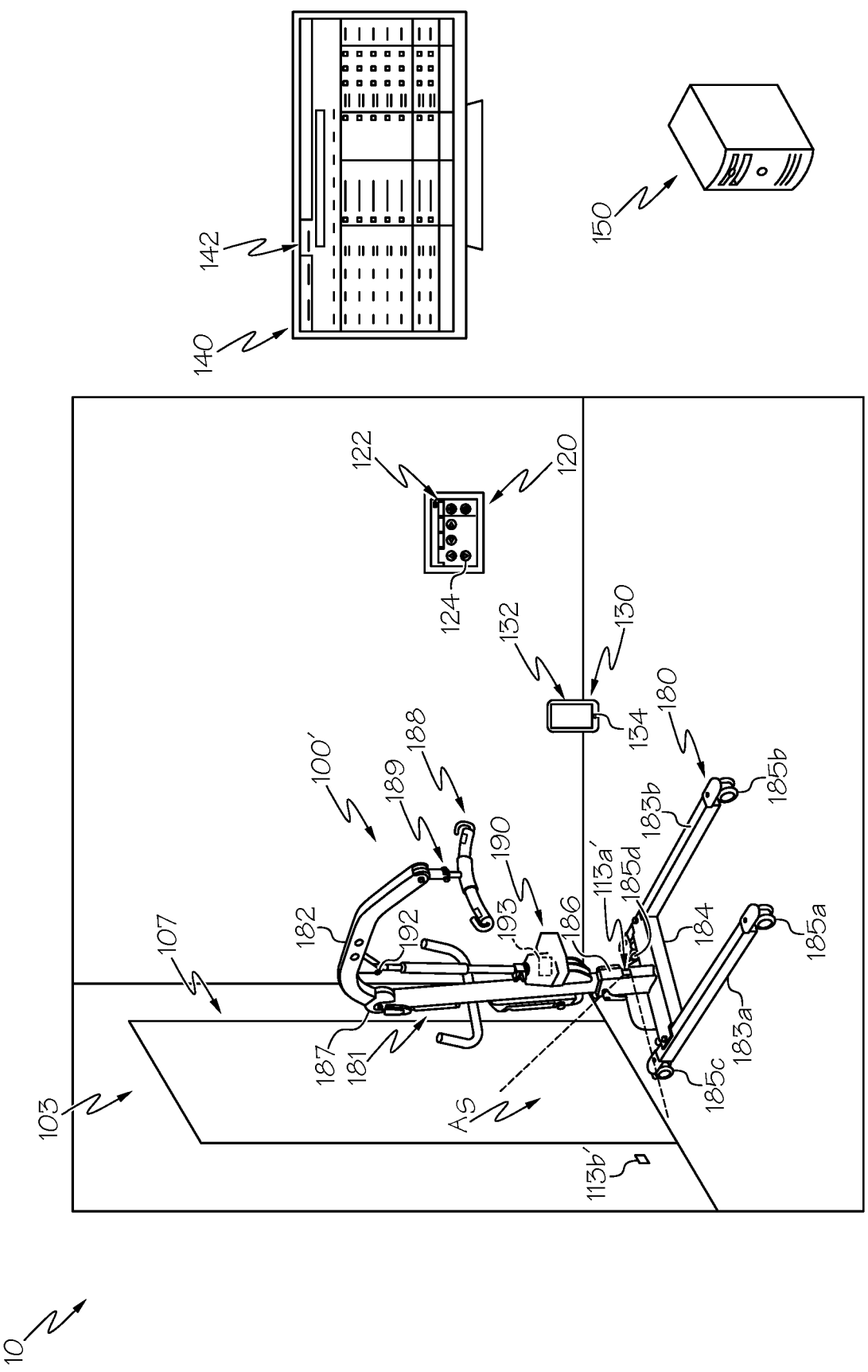
FIG. 1B schematically depicts an illustrative lift including a mobile lift, an untethered, wall-mounted control, a remote control, a remote display, and a server according to one or more embodiments shown and described herein.

Reference will now be made in detail to embodiments of interconnected components of a lift that allows for a lift unit to be coupled to an untethered, wall-mounted control and/or a remote control and allows for data to be transmitted between the various components of the lift, examples of which are illustrated in the accompanying drawings. Whenever possible, the same reference numerals will be used throughout the drawings to refer to the same or like parts. One embodiment of a lift is depicted in FIG. 1A, in which the lift includes a rail-mounted lift. Another embodiment of a lift is depicted in FIG. 1B, in which the lift includes a mobile lift. In both of the embodiments depicted in FIGS. 1A-1B, the lift units are communicatively coupled to various additional components, including an untethered, wall-mounted control, a remote control, a remote display, and/or a server. The communications between the various components allow for pairing of lift units to particular components based on location, remote control of lift units, display of information that is at least partially from data transmitted from a lift unit, and/or the like.

The phrase "communicatively coupled" is used herein to describe the interconnectivity of various components of the lifts for the purposes of transmitting and/or receiving signals, transmitting and/or receiving data, and/or the like and means that the components are generally coupled wirelessly such that signals may be exchanged between the components. It should be understood that other means of connecting the various components of the system not specifically described herein (e.g., wired connections) are included without departing from the scope of the present disclosure.

As will be evident from the present disclosure, wall-mounted controls that are communicatively coupled to a lift may provide several advantages over controls that are tethered to a lift or even remote controls such as a caregiver's mobile phone. For example, the wall-mounted controls described herein are provided at an accessible location to a user (e.g., a caregiver) and do not hinder movement of certain lifts, such as rail-mounted lifts, as such lifts must sometimes move over other equipment. Having a tethered control would cause the control to get caught or otherwise impede movement of the lift when the lift is moved over equipment. Further, sometimes the tether may not be reachable in instances where ceilings are high and/or users are short, but a wall-mounted control is always reachable. Also, tethered controls have very small screens (if any at all), and are not capable of displaying a wealth of data generated by the lift and other associated components, displaying operating instructions, displaying information pertaining to a subject (e.g., electronic medical records), and/or the like. While a user's mobile device may be able to provide such information, it may be lost or misplaced, may be subject to new installation of software when a user upgrades their device, and/or the like. In contrast, a wall-mounted control generally remains in or attached to a wall and is less likely to be lost or misplaced.

FIG. 1A generally depicts one embodiment of a lift communications system 10. The lift communications system 10 generally includes a rail-mounted lift 100 having an assembly 101 that is slidably coupled to a rail 102 via a carriage 106. The rail 102 extends along a ceiling 105 of a space 103, such as various rooms and corridors of a hospital or other medical facility. The assembly 101 of the rail-mounted lift 100 contains one or more components that can be used to lift a person, as described in greater detail herein. In some embodiments, the rail-mounted lift 100 may also include a hand control unit 112 that is used for controlling the assembly 101.

Referring briefly to FIG. 1B, the lift communications system 10 may include a mobile lift 100'. The mobile lift 100' is generally a free standing device that is movable along a floor surface of a hospital or medical facility. The mobile lift 100' contains one or more components that can be used to lift a person, as described in greater detail herein. In some embodiments, the mobile lift 100' may also include a hand control unit (not shown) that is used for controlling the mobile lift 100'.

In some embodiments, the mobile lift 100' may be included in addition to the rail-mounted lift 100 (FIG. 1A). That is, both the mobile lift 100' (FIG. 1B) and the rail-mounted lift 100 (FIG. 1A) are usable with the various components of the lift communications system 10 as described herein. In other embodiments, the mobile lift 100' (FIG. 1B) may be used in lieu of the rail-mounted lift 100 (FIG. 1A). That is, either the mobile lift 100' (FIG. 1B) or the rail-mounted lift 100 (FIG. 1A) are used in the lift communications system 10, but not both. For purposes of brevity, the present disclosure outside of FIG. 1B primarily relates to the rail-mounted lift 100 depicted in FIG. 1A. However, it should be understood that communications components the rail-mounted lift 100 and/or the functionality of the rail-mounted lift 100 described herein also apply to the mobile lift 100' of FIG. 1B.

Referring to FIGS. 1A and 1B, the lift communications system 10 may further include a wall-mounted control 120 that is communicatively coupled to the rail-mounted lift 100 and/or the mobile lift 100'. As described in greater detail herein, the wall-mounted control 120 controls various components of the rail-mounted lift 100 and/or the mobile lift 100'. In further embodiments, the lift communications system 10 may include a remote control 130 that can also be used for controlling the rail-mounted lift 100 (or components thereof) and/or the mobile lift 100' in some embodiments. FIGS. 1A and 1B further depict a remote display 140 for displaying information pertaining to data collected by the rail-mounted lift 100, data collected by the mobile lift 100' and/or data pertaining to the rail-mounted lift 100 and/or the mobile lift 100', as well as a server computing device 150 that is used for processing of various data, as described herein.

Using the components shown in FIGS. 1A and 1B, the rail-mounted lift 100 and/or the mobile lift 100' can be operated via controls within a user interface of the wall-mounted control 120, the hand control unit 112 of the rail-mounted lift 100, the hand control unit of the mobile lift 100' (not shown), and/or the remote control 130, including, but not limited to, moving components up/down, moving components laterally, activating the rail-mounted lift 100 and/or the mobile lift 100', pairing a subject with the rail-mounted lift 100 and/or the mobile lift 100', returning the rail-mounted lift 100 and/or the mobile lift 100' to a "home" position/location, receiving information from the rail-mounted lift 100 and/or the mobile lift 100' (e.g., battery status, weight of load supported by lift unit, movement history, associated subjects, etc.), performing an emergency stop of the rail-mounted lift 100 and/or the mobile lift 100', resetting the rail-mounted lift 100 and/or the mobile lift 100', and/or the like. In addition, the wall-mounted control 120 and/or the remote control 130 may provide instructions to a user for operating the rail-mounted lift 100 and/or the mobile lift 100', configuring the rail-mounted lift 100 and/or the mobile lift 100', and/or the like. The wall-mounted control 120, the remote control 130, and/or the remote display 140 may further provide data to a user pertaining to the rail-mounted lift 100 and/or the mobile lift 100'. Further, the wall-mounted control 120 may be wirelessly paired with the rail-mounted lift 100 and/or the mobile lift 100' and/or configured to pair the remote control 130 with the rail-mounted lift 100 and/or the mobile lift 100' as the rail-mounted lift 100 and/or the mobile lift 100' are moved into the space 103 (e.g., a room or the like) where the wall-mounted control 120 is located. The lift communications system 10 and the various components of the lift communications system 10 will be described in more detail herein with specific reference to the appended figures.

As will be described in further detail herein, the wall-mounted control 120 can provide connectivity, location, status, configuration, and (unloaded) control; connect to the rail-mounted lift 100 and/or the mobile lift 100' via a wireless (e.g., Bluetooth) connection, connect to the remote control 130, connect to the remote display 140, and/or connect to the server computing device 150 via a wired and/or a wireless (e.g., Wi-Fi) connection. In some embodiments, the wall-mounted control 120 can be powered by a wall plug or be hardwired into an existing electrical system. In some embodiments, the wall-mounted control 120 can be battery powered such that the wall-mounted control 120 is removable from a wall plug or hardwired electrical system and still operable. In some embodiments, the various components of the lift communications system 10 can be integrated with clinical data to track lifts per subject over time and/or integrated with service data for the purposes of providing device status, software management, and/or the like, as discussed in greater detail herein. In addition, the wall-mounted control 120 can be integrated with clinical data to track lifts per subject over time and/or integrated with service data for the purposes of providing device status, software management, and/or the like.

The systems and methods described herein addresses the problems noted above and offers a channel into future solutions. By having a larger wall-mounted control available to individuals such as, for example, a caregiver, at a reachable height, the individual can operate the lift at a more convenient height. In addition, the various systems and methods described herein allow for control of the rail-mounted lift 100 and/or the mobile lift 100' without having to use hand control unit, particularly in instances where it may be difficult or impossible to use hand control unit 112 (e.g., because of a location of the rail-mounted lift 100 and/or the mobile lift 100', a location of other items in the space 103, an inability to continuously move the rail-mounted lift 100 with the hand control unit 112 because of obstructions present while moving, and/or the like). The various systems and methods described herein address issues pertaining to a lack of data provided to users that allow the users to make informed decisions regarding usage of the rail-mounted lift 100 and/or the mobile lift 100'. By having a larger wall-mounted control 120 and/or a remote control 130 available to a caregiver at an accessible location and providing other information that is pertinent to use/movement of the rail-mounted lift 100, the caregiver can now use operation controls on the wall-mounted control 120 and/or the remote control 130 in a way that is much more effective and avoids operational issues pertaining to use of a hand control unit 112 that does not detach from the assembly 101 or have the capability to display other pertinent information relating to the rail-mounted lift 100. As a result, a caregiver can store the hand control unit 112 and/or a sling bar 110 coupled to the assembly 101 all the way up in the ceiling 105, out of the way. The caregiver can also transfer the rail-mounted lift 100 across the space 103 while it is stored in the highest position up and over any curtains or obstacles. Lastly, the caregiver is given a larger, more informative screen to view and navigate subject information, support information on how to operate the rail-mounted lift 100 and/or the mobile lift 100', additional information that might influence operation of the rail-mounted lift 100 and/or the mobile lift 100', and controls for operating the rail-mounted lift 100 and/or the mobile lift 100', all at a size that is easily read and understood and does not require reference to other devices, charts, and/or the like while operating.

Figure 2:
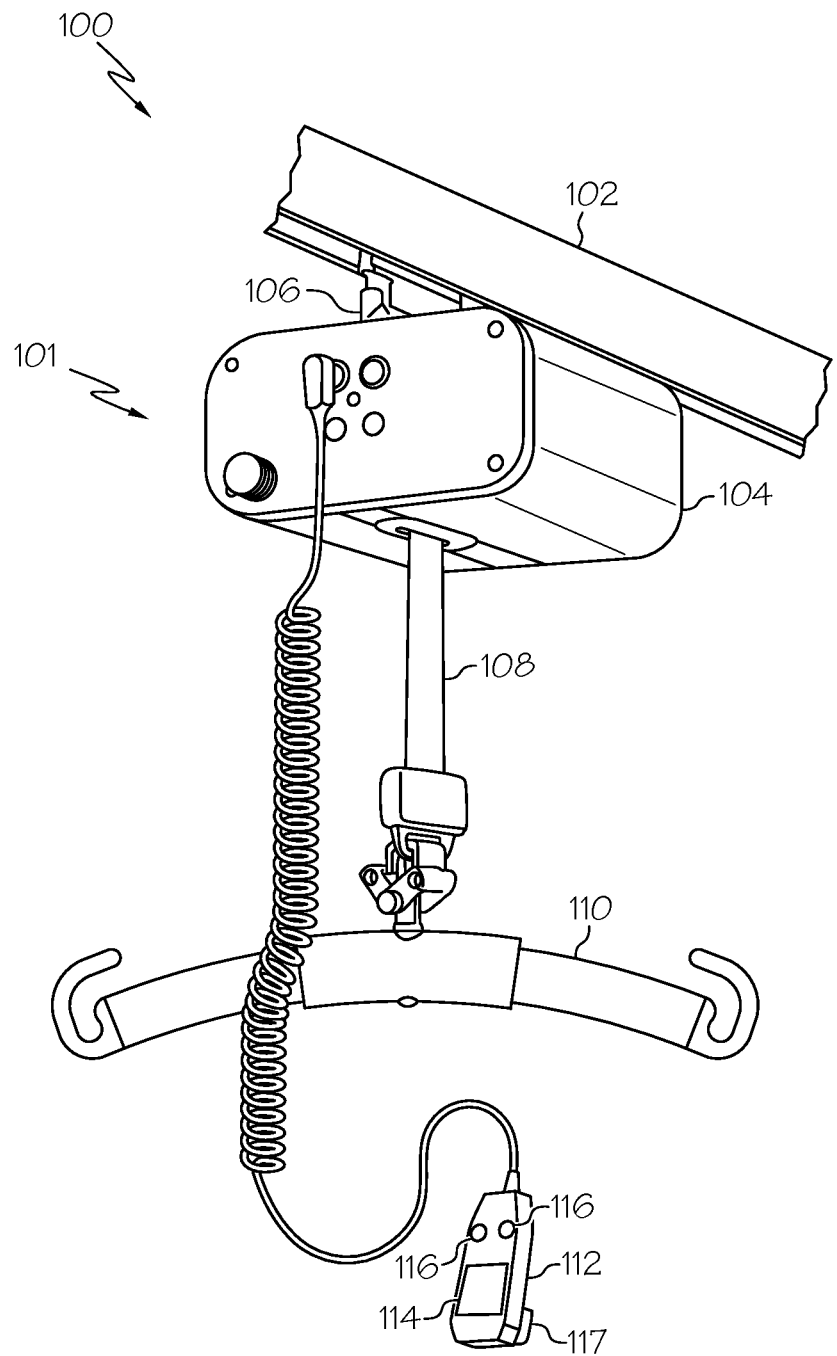
FIG. 2 schematically depicts an illustrative rail-mounted lift according to one or more embodiments described herein.

Referring now to FIGS. 1A and 2, the rail-mounted lift 100 generally includes an assembly 101 coupled to a rail 102. More specifically, the assembly 101 includes a lift unit 104 that is slidably coupled to a rail 102 via a carriage 106. The lift unit 104 may be used to support and/or lift a subject with a lifting strap 108 which is coupled to a motor (not shown) contained within the lift unit 104. The motor facilitates extending or retracting the lifting strap 108 from the lift unit 104, thereby raising and lowering a subject attached to the lifting strap 108.

In the embodiment of the rail-mounted lift 100 depicted in FIGS. 1A and 2, a subject may be attached to the lifting strap 108 with a sling bar 110 or a similar accessory attached to the lifting strap 108. More specifically, the sling bar 110 or a similar accessory may be attached to a harness or sling in which the subject is positioned, thereby facilitating the lifting operation.

Various components of the assembly 101, such as the lift unit 104 and/or components thereof, may be operated with the hand control unit 112 that is communicatively coupled to the lift unit 104, the wall-mounted control 120, and/or the remote control 130. In the embodiment shown in FIGS. 1A and 2, the hand control unit 112 is directly wired to the lift unit 104. In other embodiments, the hand control unit 112 may be omitted. Rather, control of the lift unit 104 is completed via one or more of the wall-mounted control 120 and the remote control 130.

In some embodiments, the hand control unit 112 may include a display 114, one or more user interface controls 116, and/or a sensing device 117. The display 114 is generally any liquid crystal display (LCD), light emitting diode (LED) display, electronic ink (e-ink) display, or the like that can display information to a user. In some embodiments, the display 114 may be configured as an interactive display that can receive user inputs (e.g., a touch screen display or the like). The one or more user interface controls 116 may be hardware components that receive inputs from a user and transmit signals corresponding to the inputs, such as a keyboard, a mouse, a joystick, a touch screen, a remote control, a pointing device, a video input device, an audio input device, a haptic feedback device, and/or the like. In some embodiments, the display 114 and one or more of the user interface controls 116 may be combined into a single device, such as a touchscreen display or the like. The display 114 and/or the one or more user interface controls 116 may be used, for example, to allow a user to manually input information pertaining to an identity of the user, an identity of a subject, a location or sub-location of the assembly 101, to provide instructions for programming and/or pairing the assembly 101 with one or more other components, and/or the like. In some embodiments, the sensing device 117 of the hand control unit 112 contains hardware for sensing a code and transmitting data corresponding to the code. Illustrative hardware includes, but is not limited to, an imaging device, an IR receiver, an RFID detector (e.g., an electromagnetic field generator), a wireless receiver (e.g., a radio utilizing a wireless technology standard such as Bluetooth or 802.11x), or the like. In a particular embodiment, the sensing device 117 is an imaging device that is adapted to read a barcode (or any other symbology, QR code, or the like).

Figure 3:
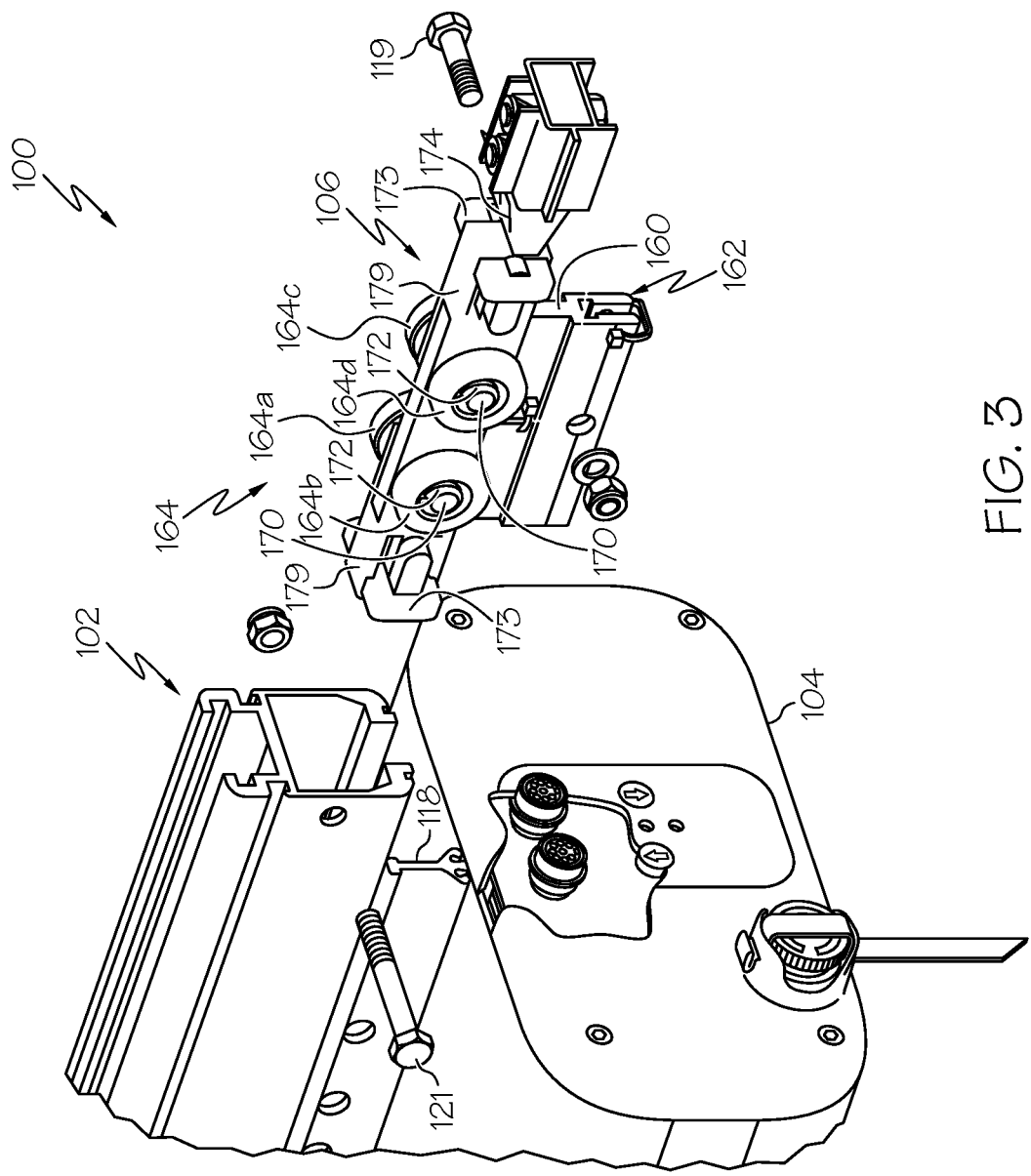
FIG. 3 schematically depicts an exploded view of various components of an interconnection between an illustrative carriage and an illustrative rail of a rail-mounted lift according to one or more embodiments shown and described herein.

Referring now to the exploded view of the rail-mounted lift 100 schematically depicted in FIG. 3, the lift unit 104 is mechanically coupled to a carriage 106 which facilitates slidably positioning the lift unit 104 along the rail 102. In the embodiments of the lift unit 104 described herein, the lift unit 104 includes a connection rail 118 which is mounted to a top surface of the lift unit 104. The connection rail 118 facilitates connecting and securing the lift unit 104 to the carriage 106. In the embodiment of the lift unit 104 shown in FIG. 3, the connection rail 118 has a T-shaped configuration and the carriage 106 has a receiving slot 162 with a complimentary configuration for receiving the connection rail 118. The carriage 106 may be secured to the connection rail 118 with a fastener 119, such as a bolt and nut as depicted in FIG. 3, which extends transversely through openings in the carriage 106 and a corresponding opening in the connection rail 118.

In embodiments, the carriage 106 generally includes a carriage body 160 having an extension 166 to which a plurality of support wheels 164*a*, 164*b*, 164*c*, and 164*d* (collectively, support wheels 164) are rotatably attached for supporting the carriage 106 in the rail 102. The support wheels 164 facilitate positioning the carriage 106 and lift unit 104 along the length of the rail 102. In the embodiments described herein, the carriage 106 is depicted with four support wheels 164. However, it is contemplated that the carriage 106 may be constructed with fewer than four (4) support wheels 164. For example, in some embodiments, the carriage 106 may be constructed with one or two support wheels 164 (e.g., a pair of support wheels 164). Accordingly, it should be understood that the carriage 106 includes at least one support wheel 164. The support wheels 164 are positioned on axles 170 which extend transversely through the carriage body 160. Each support wheel 164 is secured to the axle 170 with a fastener, such as retaining clips 172, such that the support wheels 164 are rotatable on the axle 170.

In the embodiment of the carriage 106 depicted in FIG. 3, the support wheels 164 are passive (i.e., the support wheels 164 are not actively driven with a motor or a similar drive mechanism) and the lift unit 104 is manually traversed along the rail 102 (e.g., such as when a user pushes or pulls the lift unit 104 along the rail 102). However, in alternative embodiments (not shown), the support wheels may be actively driven, such as when the support wheels are coupled to a motor or a similar mechanism. In such embodiments, referring also to FIG. 1A, the drive mechanism may be communicatively coupled to a control unit (such as the hand control unit 112, the wall-mounted control 120, and/or the remote control 130) which actuates the drive mechanism and facilitates traversing the lift unit 104 along the rail 102 with the drive mechanism. As such, a user may actuate one or more user interface controls on the hand control unit 112, the wall-mounted control 120, and/or the remote control 130 to cause the lift unit 104 to traverse along the rail 102. Further, a user may adjust a speed, a direction, and/or the like of the movement of the lift unit 104 along the rail 102 via the one or more user interface controls on the hand control unit 112, the wall-mounted control 120, and/or the remote control 130. Further, a user may utilize data obtained regarding the rail-mounted lift 100, a subject, and/or the like to determine potential movement parameters (e.g., speed, direction, starting/stopping, and/or the like). In some embodiments, the one or more user interface controls on the hand control unit 112, the wall-mounted control 120, and/or the remote control 130 may be provided to a user based on potential movement parameters. For example, if a subject has a particular mobility score or the like, the one or more user interface controls on the hand control unit 112, the wall-mounted control 120, and/or the remote control 130 may be adjusted, limited, provided, and/or the like based on the mobility score. For example, a speed may be limited to a particular speed (e.g., a maximum, not-to-exceed speed) for a particular mobility score such that, when the user actuates the one or more user interface controls on the hand control unit 112, the wall-mounted control 120, and/or the remote control 130, the lift unit 104 will not move along the rail 102 at a speed higher than the limited particular speed.

Still referring to FIG. 3, the carriage 106 may further include bumper assemblies 179 positioned on either end of the carriage body 160 in some embodiments. The bumper assemblies 179 may be attached to the carriage body 160 and secured in place with the axles 170 which extend transversely through the carriage body 160. The bumper assemblies 179 may include rubber end caps 173 which cushion the carriage 106 when the carriage 106 encounters an end stop 174 located at either end of the rail 102, the end stops 174 being secured in the rail 102 by a fastener 121, which may be a bolt and a nut in some embodiments. In the embodiments of the carriage 106 described herein, the bumper assemblies 179 are optional and, as such, it should be understood that the carriage 106 may be constructed without the bumper assemblies 179.

Figure 4:
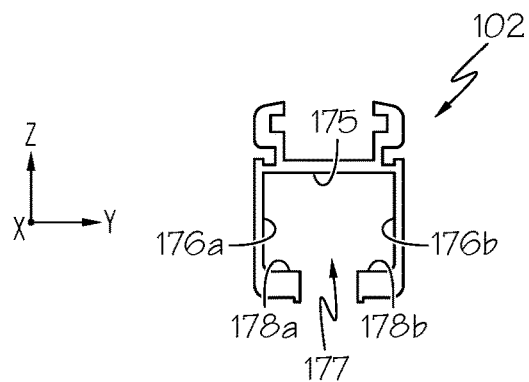
FIG. 4 schematically depicts a cross section of an illustrative rail of the rail-mounted lift according to one or more embodiments described herein.

Referring to FIGS. 3 and 4, the rail-mounted lift 100 further includes a rail 102 in which the carriage 106 is slidably disposed for relative movement to the rail 102. Accordingly, it should be understood that, when the lift unit 104 is mechanically coupled to the carriage 106, the lift unit 104 may be traversed along the rail 102 with the carriage 106. In the embodiment of the rail 102 shown in FIG. 4, the rail 102 is generally formed from a metallic material, such as aluminum, an aluminum alloy, or a similar metallic material. Still referring to FIGS. 3 and 4, the rail 102 generally includes an upper portion 175, a first sidewall 176*a* integrally formed with the upper portion 175, and a second sidewall 176*b* integrally formed with the upper portion 175. The upper portion 175, first sidewall 176*a* and second sidewall 176*b* are oriented such that the upper portion 175, first sidewall 176*a* and second sidewall 176*b* form a carriage support channel 177 in which the carriage 106 is slidably disposed. To that end, the first sidewall 176*a* further includes a first support flange 178*a* which extends from the first sidewall 176*a* into the carriage support channel 177 and the second sidewall 176*b* further includes a second support flange 178*b* which extends from the second sidewall 176*b* into the carriage support channel 177. In the embodiments described herein, the first support flange 178*a* and the second support flange 178*b* are generally opposed to one another and lie in a common horizontal plane (e.g., the x-y plane in the coordinate axes shown in FIG. 4). The first support flange 178*a* and the second support flange 178*b* may also be substantially parallel with the upper portion 175 of the rail 102. However, it should be understood that other configurations of the support flanges 178*a*, 178*b* and the upper portion 175 of the rail 102 are also contemplated. For example, in an alternative embodiment, the support flanges 178*a*, 178*b* may be upwardly angled with respect to the horizontal plane. Moreover, it should be understood that the structure of the rail 102 depicted in FIGS. 3 and 4 is illustrative and that other rail configurations are contemplated.

Figure 5:
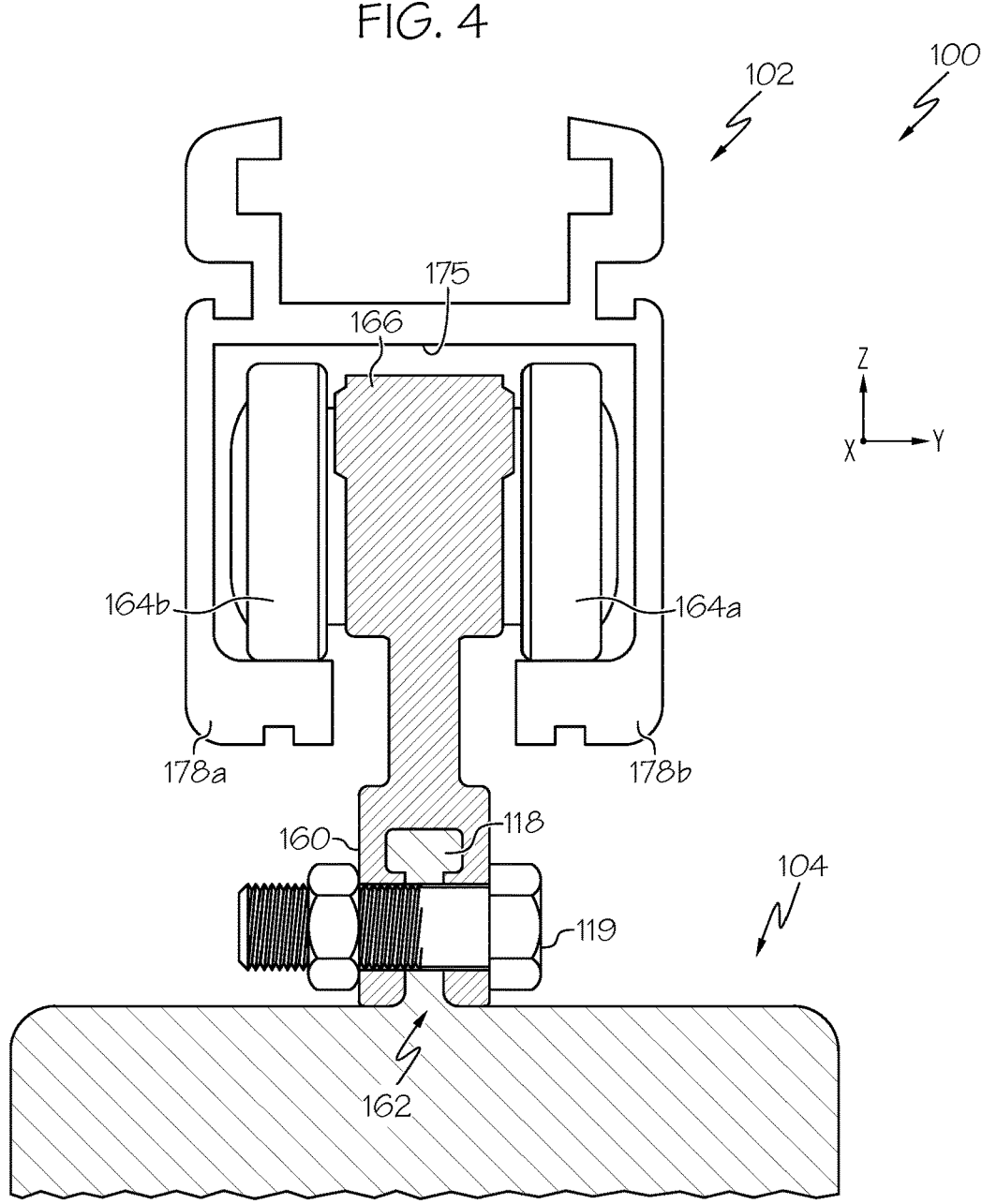
FIG. 5 schematically depicts a cross section of a rail-mounted lift engaged with an illustrative rail in a rail-mounted lift according to one or more embodiments shown and described herein.

The construction of the rail-mounted lift 100 will now be described with specific reference to the exploded view of the rail-mounted lift 100 shown in FIG. 3 and the cross section of the assembled rail-mounted lift 100 shown in FIG. 5. As shown in FIGS. 3 and 5, the carriage 106 is installed on the lift unit 104 by inserting the connection rail 118 into the corresponding receiving slot 162 of the carriage 106 and securing the carriage 106 on the connection rail 118 with a fastener 119. The lift unit 104 with attached carriage 106 is then suspended from the rail 102 by positioning the extension 166 of the carriage body 160 in the rail 102 such that the support wheels 164a, 164b are slidably engaged with the first support flange 178a and the second support flange 178b, respectively.

Referring again to FIG. 1A, also depicted is a load sensor 109 associated with the rail-mounted lift 100. The load sensor 109 depicted in FIG. 1A may generally be a sensor that is arranged and configured to sense various characteristics and/or parameters associated with the rail-mounted lift 100. For example, the load sensor 109 may be positioned on or adjacent to the lifting strap 108 to sense a tension of the lifting strap 108, which may be used to determine a type of sling bar 110 being used, whether a subject is presently being supported by the sling bar 110, the weight of a subject supported by the sling bar 110, and/or a positioning of a subject supported by the sling bar 110. As such, the load sensor 109 may be a load cell, such as a hydraulic load cell, a pneumatic load cell, a piezoelectric load cell, a strain gauge load cell, and/or the like. While only a single one of the load sensor 109 is depicted in FIG. 1A, it should be understood that this is merely illustrative. That is, a plurality of load sensors 109 positioned on or adjacent to the lifting strap 108 are contemplated and included within the scope of the present disclosure. As described in greater detail herein, the load sensor 109 may provide information that is transmitted to one or more components of the lift communications system 10 and used for a plurality of purposes, such as displaying load related data to a user or the like. The rail-mounted lift 100 may also include one or more other sensors that sense various characteristics associated with the rail-mounted lift 100, such as movement of the lift unit 104, movement of the lifting strap 108, and/or the like. One illustrative, non-limiting example of such a sensor is a potentiometer.

FIG. 1A also depicts a locating system 111 that is coupled to one or more components of the rail-mounted lift 100. The locating system 111 generally includes a first component 113a and a second component 113b. The first component 113a and the second component 113b function as a receiver and a transmitter. That is, the first component 113a may be a receiver or a transmitter and the second component 113b may be a transmitter or a receiver. For example, in embodiments where the first component 113a is a receiver, the second component 113b may be a transmitter. Additionally, in embodiments where the first component 113a is a transmitter, the second component 113b may be a receiver.

The first component 113a and the second component 113b, when configured as a transmitter, are generally any device or component that transmits, displays, or otherwise provides an encoded signal that is obtainable or otherwise receivable by the receiver. Accordingly, the first component 113a and the second component 113b, when configured as a receiver, are generally any device or component that obtains or otherwise receives the encoded signal from the transmitter. The transmitter may be a passive device such as a printed code (such as a barcode, a QR code, or the like), or may be an active device such as an infrared (IR) beacon, a radio frequency identification (RFID) emitter or tag, a wireless transmitter, or the like. The transmitter is printed, attached, or otherwise affixed to an area on or around the rail 102 or a portion of the assembly 101, such as the lift unit 104 or the carriage 106. In embodiments where the transmitter is an RFID emitter or tag affixed to the rail 102, the RFID emitter or tag may be affixed in such a manner that the RFID signal is not propagated through the rail 102 (e.g., by coupling the RFID emitter or tag to an insulation device or the like).

In addition, the receiver may be an imaging device, an IR receiver, an RFID detector (e.g., an electromagnetic field generator), a wireless receiver (e.g., a radio utilizing a wireless technology standard such as Bluetooth or 802.11x), or the like. In a particular embodiment, the receiver may include, for example, a CS468 RFID reader and a CS790 antenna available from Convergence Systems Ltd. of Hong Kong, which may be used in conjunction with one another to shape an active area of the receiver. The receiver may be attached to or integrated with a component of the assembly 101, such as, for example, the lift unit 104 or the carriage 106, or may be attached or integrated on or near the rail 102. The transmitter and the receiver may further be positioned or otherwise arranged such that the encoded signal provided by the transmitter is received by the receiver when the transmitter and the receiver pass one another due to movement of the carriage 106 along the rail 102, as described in greater detail herein. For example, the transmitter and the receiver may be arranged such that a line-of-sight alignment is achieved between the transmitter and the receiver when the carriage 106 passes a particular location along the rail 102.

In the embodiment depicted in FIG. 1A, the first component 113a is coupled to the lift unit 104 and the second component 113b is positioned on the rail 102. However, these locations are merely illustrative, and the first component 113a and the second component 113b may be located elsewhere with respect to the rail-mounted lift 100 (or components thereof) in other embodiments. Solely for the purposes of explanation herein, the embodiment of FIG. 1A depicts the first component 113a coupled to the lift unit 104 and configured as a receiver, and the second component 113b positioned on the rail 102 and configured as a transmitter.

The portion of the locating system 111 that functions as the receiver (e.g., the first component 113a or the second component 113b) may sense a sensed area $A_s$ that generally encompasses an area adjacent to the receiver. That is, the sensed area $A_s$ may be an area completely surrounding the receiver in some embodiments. In other embodiments, the sensed area $A_s$ may be an area encompassed by the field of view of the receiver, such as when the receiver is an imaging device or an IR receiver. In some embodiments, the sensed area $A_s$ may be an active region that is shaped through use of appropriate antennas and readers such that only components in a particular area (e.g., along the rail 102) are sensed. In the embodiment depicted in FIG. 1A, the sensed area $A_s$ may generally be an area bound by the dashed lines, which extends from the lift unit 104 to a portion of the rail 102.

The portion of the locating system 111 that functions as the transmitter (e.g., the first component 113a or the second component 113b) may be located in any location on the rail 102 throughout the space 103, particularly in locations where it may be advantageous to determine a location of the rail-mounted lift 100. For example, for ease of associating the correct wall-mounted control 120 to the correct rail-mounted lift 100 in embodiments where a facility includes a plurality of each, the transmitter may be positioned at a location on the rail 102 that would be passed when the lift unit 104 enters the space 103, such as near a doorway or the like. However, such a location is merely illustrative and other locations are contemplated.

It should be understood that the locating system 111 is only one illustrative example of a system that is used to determine a location of the rail-mounted lift 100. Other systems and methods are also contemplated, such as, for example, one or more signal triangulation algorithms that are adapted to determine a location based on signals wirelessly transmitted to or from the rail-mounted lift 100, other tracking hardware such as global positioning satellite (GPS) hardware, and/or the like.

Referring again to FIG. 1B, the mobile lift 100' may also include a base 180, a lift mast 181 and a lift arm 182. The base may include one or more base legs (e.g., base legs 183a, 183b) which are attached to a cross support 184. The base legs 183a, 183b may include one or more casters (e.g., a pair of front casters 185a, 185b and/or a pair of rear casters 185c, 185d). The rear casters 185c, 185d may comprise caster brakes (not shown). In some embodiments, the casters may be powered casters that are coupled to a motor, actuator, or the like that drives movement of the casters, and thus the mobile lift 100' throughout the space 103. Control of the motor, actuator, or the like may be completed using the remote control 130 and/or the wall-mounted control 120, as described in greater detail herein.

In one embodiment, the base 180 may further include a mast support 186 disposed on the cross support 184. In one embodiment, the mast support 186 may be a rectangular receptacle configured to receive the lift mast 181 of the mobile lift 100'. For example, a first end of the lift mast 181 may be adjustably received in the mast support 186 and secured with a pin, threaded fastener, or a similar fastener. The pin or threaded fastener may extend through the mast support 186 and into a corresponding adjustment hole(s) (not shown) on the lift mast 181. In another example, the mast support 186 may include an actuator therein that couples to the lift mast and allows for vertical movement of the lift mast 181 (e.g., up and down movement of the lift mast 181). Accordingly, it will be understood that the position of the lift mast 181 may be adjusted vertically with respect to the base 180 by repositioning the lift mast 181 in the mast support 186 using the actuator. Control of the actuator may be completed using the remote control 130 and/or the wall-mounted control 120, as described in greater detail herein.

In some embodiments, the lift arm 182 is pivotally coupled to the lift mast 181 at a lift arm pivot 187 at a second end of the lift mast 181 such that the lift arm 182 may be pivoted (e.g., raised, lowered, moved from side to side) with respect to the base 180. In some embodiments, the lift arm 182 may be coupled to one or more actuators at the lift arm pivot 187 such that the actuators facilitate the pivot movement of the lift arm 182. Control of the one or more actuators may be completed using one or more of the remote control 130 and/or the wall-mounted control 120, as described in greater detail herein.

The lift arm 182 may comprise at least one sling bar 188 coupled to the lift arm 182 with a coupling member 189 such that the sling bar 188 is raised or lowered with the lift arm 182. In the embodiment shown in FIG. 1B, the coupling member 189 is pivotally attached to the lift arm 182 at an end of the lift arm 182 opposite the lift arm pivot 187. In one embodiment, the coupling member 189 is pivotally attached to the lift arm 182 at attachment pivot such that the sling bar 188 may be pivoted with respect to the lift arm 182. However, it should be understood that, in other embodiments, the coupling member 189 may be fixedly attached to the lift arm 182 or that the sling bar 188 may be directly coupled to the lift arm 182 without the use of a coupling member 189.

In the embodiments described herein, the mobile lift 100' is a mechanized lifting device. Accordingly, raising and lowering the lift arm 182 with respect to the base 180 may be achieved using an actuator such as a lift actuator 190 or the like. The lift actuator 190 may be a linear actuator that includes a motor (not shown) mechanically coupled to an actuator arm 191. More specifically, the motor may include a rotating armature (not shown) and the actuator arm 191 may include one or more threaded rods coupled to the armature such that, when the armature is rotated, the threaded rods are extended or retracted relative to one another and the actuator arm 191 is extended or retracted. In some embodiments, the lift actuator 190 may further include a support tube disposed over the actuator arm 191. The support tube provides lateral support to the actuator arm 191 as the actuator arm is extended. As will be described in greater detail herein, the lift actuator 190 (as well as any other actuator within the mobile lift 100') is coupled to an electronic control unit that facilitates actuation and control of the lift actuator 190.

In the embodiment shown in FIG. 1B, the lift actuator 190 is fixedly mounted on the lift mast 181 and pivotally coupled to the lift arm 182. In particular, the lift mast 181 includes a bracket to which the lift actuator 190 is attached while the actuator arm 191 is pivotally coupled to the lift arm 182 at an actuator pivot 192. Accordingly, it should be understood that, by actuating the lift actuator 190 with the motor, the actuator arm 191 is extended or retracted, thereby raising or lowering the lift arm 182 relative to the base 180. In one embodiment, the lift actuator 190 may further include an emergency release. The emergency release facilitates the manual retraction of the actuator arm 191 in the event of a mechanical or electrical malfunction of the lift actuator 190.

While the embodiments described herein refer to the lift actuator 190 as including a motor and an actuator arm 191, it will be understood that the lift actuator 190 may have various other configurations and may include a hydraulic or pneumatic actuator comprising a mechanical pump or compressor, or a similar type of actuator. Further, in other embodiments, where the lifting device is a cable-based lift, the lift actuator 190 may be a motor which pays out and/or takes-up cable, thereby raising and/or lowering an attached load. Accordingly, it will be understood that various other types of actuators may be used to facilitate raising and lowering the lift arm 182 and/or an attached load with respect to the base 180.

Also depicted in the embodiment of FIG. 1B is a load sensor 193 associated with the mobile lift 100'. The load sensor 193 depicted in FIG. 1B may generally be a sensor that is arranged and configured to sense various characteristics and or parameters associated with the mobile lift 100'. For example, the load sensor 193 may be positioned on or adjacent to the lift actuator 190 to sense a tension that may result from operation of the lift actuator 190, which may be used to determine a type of sling bar 188 being used, whether a subject is presently being supported by the sling bar 188, the weight of a subject supported by the sling bar 188, and/or a positioning of a subject supported by the sling bar 188. As such, the load sensor 193 may be a load cell, such as a hydraulic load cell, a pneumatic load cell, a piezoelectric load cell, a strain gauge load cell, and/or the like. While only a single one of the load sensor 193 is depicted in FIG. 1B, it should be understood that this is merely illustrative. That is a plurality of load sensors 193 positioned on or adjacent to the lift actuator 190 (or on other areas of the mobile lift 100') are contemplated and included within the scope of the present disclosure. As described in greater detail herein, the load sensor 193 may provide information that is transmitted to one or more components of the lift communications system 10 and used for a plurality of purposes, such as displaying load related data to a user or the like.

In the embodiment shown in FIG. 1B, the mobile lift 100' also includes a locating system 111' that is coupled to one or more components of the mobile lift 100'. The locating system 111' generally includes a first component 113a' and a second component 113b'. The first component 113a' and the second component 113b' function as a receiver and a transmitter. That is, the first component 113a' may be a receiver or a transmitter and the second component 113b' may be a transmitter or a receiver. For example, in embodiments where the first component 113a' is a receiver, the second component 113b' may be a transmitter. Additionally, in embodiments where the first component 113a' is a transmitter, the second component 113b' may be a receiver.

The first component 113a' and the second component 113b', when configured as a transmitter, are generally any device or component that transmits, displays, or otherwise provides an encoded signal that is obtainable or otherwise receivable by the receiver. Accordingly, the first component 113a' and the second component 113b', when configured as a receiver, are generally any device or component that obtains or otherwise receives the encoded signal from the transmitter. The transmitter may be a passive device such as a printed code (such as a barcode, a QR code, or the like), or may be an active device such as an infrared (IR) beacon, a radio frequency identification (RFID) emitter or tag, a wireless transmitter, or the like. The transmitter is printed, attached, or otherwise affixed to an area within the space 103 or a portion of the mobile lift 100'. For example, the transmitter may be positioned on a wall of the space 103 that is adjacent to an opening 107 into the space 103 through which the mobile lift 100' can travel, such as a doorway or the like. Such a positioning may ensure that information pertaining to the mobile lift 100' can be obtained for the purposes of pairing the mobile lift 100' with various components of the lift communications system 10, controlling the mobile lift 100', transmitting information, and/or the like, as described herein.

In addition, the receiver may be an imaging device, an IR receiver, an RFID detector (e.g., an electromagnetic field generator), a wireless receiver (e.g., a radio utilizing a wireless technology standard such as Bluetooth or 802.11x), or the like. In a particular embodiment, the receiver may include, for example, a CS468 RFID reader and a CS790 antenna available from Convergence Systems Ltd. of Hong Kong, which may be used in conjunction with one another to shape an active area of the receiver. The receiver may be attached to or integrated with a component of the mobile lift 100' or may be attached or integrated on or near a component within the space 103. The transmitter and the receiver may further be positioned or otherwise arranged such that the encoded signal provided by the transmitter is received by the receiver when the transmitter and the receiver pass one another due to movement of the mobile lift 100' within the space. For example, the transmitter and the receiver may be arranged such that a line-of-sight alignment is achieved between the transmitter and the receiver when the mobile lift 100' passes a particular area of the space 103, such as the opening 107 into the space 103.

In the embodiment depicted in FIG. 1B, the first component 113a' is coupled to a portion of the mobile lift 100' and the second component 113b' is positioned on a wall of the space 103 near the opening 107 into the space. However, these locations are merely illustrative, and the first component 113a' and the second component 113b' may be located elsewhere with respect to the mobile lift 100' (or components thereof) in other embodiments. Solely for the purposes of explanation herein, the embodiment of FIG. 1B depicts the first component 113a' coupled to a portion of the mobile lift 100' and configured as a receiver, and the second component 113b' positioned on a wall of the space 103 and configured as a transmitter.

The portion of the locating system 111' that functions as the receiver (e.g., the first component 113a' or the second component 113b') may sense a sensed area $A_s$ that generally encompasses an area adjacent to the receiver. That is, the sensed area $A_s$ may be an area completely surrounding the receiver in some embodiments. In other embodiments, the sensed area $A_s$ may be an area encompassed by the field of view of the receiver, such as when the receiver is an imaging device or an IR receiver. In some embodiments, the sensed area $A_s$ may be an active region that is shaped through use of appropriate antennas and readers such that only components in a particular area (e.g., a particular area of the space 103) are sensed. In the embodiment depicted in FIG. 1B, the sensed area $A_s$ may generally be an area bound by the dashed lines, which extends from the first component 113a' to the second component 113b'.

It should be understood that the locating system 111' is only one illustrative example of a system that is used to determine a location of the mobile lift 100'. Other systems and methods are also contemplated, such as, for example, one or more signal triangulation algorithms that are adapted to determine a location based on signals wirelessly transmitted to or from the mobile lift 100', other tracking hardware such as global positioning satellite (GPS) hardware, and/or the like Referring again to the embodiments depicted in FIGS. 1A and 1B, the wall-mounted control 120 includes one or more components that provide functionality for using the lift unit 104. For example, the wall-mounted control 120 may cause the motor within the lift unit 104 to extend or retract the lifting strap 108, move components up/down, move components laterally, activate the lift unit 104, pair a subject with a lift unit 104, return a lift unit 104 to a "home" position/location, receive information from a lift unit 104 (e.g., battery status, weight of load supported by lift unit 104, movement history, associated subjects, etc.), perform an emergency stop of the lift unit 104, reset the lift unit 104, and/or the like. In another example, the wall-mounted control includes components for using the mobile lift 100', causing a motor within the mobile lift 100' to move components up/down, moving components laterally, activating the mobile lift 100', pairing a subject with the mobile lift 100', returning the mobile lift 100' to a "home" position/location, receiving information from the mobile lift 100' (e.g., battery status, weight of load supported by the mobile lift 100', movement history, associated subjects, etc.), performing an emergency stop of the mobile lift 100', resetting the mobile lift 100', and/or the like.

The wall-mounted control 120 may include, for example, a display 122 and/or one or more user interface controls 124. The display 122 is generally any liquid crystal display (LCD), light emitting diode (LED) display, electronic ink (e-ink) display, or the like that can display information to a user. In some embodiments, the display 122 may be configured as an interactive display that can receive user inputs (e.g., a touch screen display or the like). The one or more user interface controls 124 may be hardware components that receive inputs from a user and transmit signals corresponding to the inputs. The embodiment of FIG. 1 includes user interface controls 124 in the form of a touch screen.

However, other user interface controls are contemplated and included within the scope of the present disclosure, including, but not limited to, a keyboard, a mouse, a joystick, a remote control, a pointing device, a video input device, an audio input device, a haptic feedback device, and/or the like. In some embodiments, the display 122 and one or more of the user interface controls 124 may be combined into a single device, such as a touchscreen display or the like (as depicted in FIGS. 1A-1B). The display 122 and/or the one or more user interface controls 124 may be used, for example, to allow a user to interact with the wall-mounted control 120 for the purposes of moving components up/down, moving components laterally, activating the lift unit 104 and/or the mobile lift 100', pairing a subject with a lift unit 104 and/or a mobile lift 100', returning a lift unit 104 and/or a mobile lift 100' to a "home" position/location, receiving information from a lift unit 104 and/or a mobile lift 100' (e.g., battery status, weight of load supported by lift unit 104, movement history, associated subjects, etc.), performing an emergency stop of the lift unit 104 and/or the mobile lift 100', resetting the lift unit 104 and/or the mobile lift 100', and/or the like. Additional details regarding the wall-mounted control 120 will be discussed herein with respect to FIG. 7.

Still referring to FIGS. 1A and 1B, the remote control 130 includes one or more components that provide functionality for using the lift unit 104 and/or the mobile lift 100'. For example, the remote control 130 may include one or more components for causing the motor within the lift unit 104 to extend or retract the lifting strap 108, moving components up/down, moving components laterally, activating the lift unit 104 and/or the mobile lift 100', pairing a subject with a lift unit 104 and/or the mobile lift 100', returning a lift unit 104 and/or the mobile lift 100' to a "home" position/location, receiving information from a lift unit 104 and/or the mobile lift 100' (e.g., battery status, weight of load supported by a lift, movement history, associated subjects, etc.), performing an emergency stop of the lift unit 104 and/or the mobile lift 100', resetting the lift unit 104 and/or the mobile lift 100', and/or the like.

The remote control 130 may include, for example, a display 132 and/or one or more user interface controls 134. The display 132 is generally any liquid crystal display (LCD), light emitting diode (LED) display, electronic ink (e-ink) display, or the like that can display information to a user. In some embodiments, the display 132 may be configured as an interactive display that can receive user inputs (e.g., a touch screen display or the like). The one or more user interface controls 134 may be hardware components that receive inputs from a user and transmit signals corresponding to the inputs. The embodiments of FIGS. 1A and 1B include user interface controls 134 in the form of physical buttons. However, other user interface controls are contemplated and included within the scope of the present disclosure, including, but not limited to, a keyboard, a mouse, a joystick, a remote control, a pointing device, a video input device, an audio input device, a haptic feedback device, a touch screen, and/or the like. In some embodiments, the display 132 and one or more of the user interface controls 134 may be combined into a single device, such as a touchscreen display or the like. The display 132 and/or the one or more user interface controls 134 may be used, for example, to allow a user to interact with the remote control 130 for the purposes of moving components up/down, moving components laterally, activating the lift unit 104 and/or the mobile lift 100', pairing a subject with a lift unit 104 and/or the mobile lift 100', returning a lift unit 104 and/or the mobile lift 100' to a "home" position/location, receiving information from a lift unit 104 and/or the mobile lift 100' (e.g., battery status, weight of load supported by lift unit 104 and/or the mobile lift 100', movement history, associated subjects, etc.), performing an emergency stop of the lift unit 104 and/or the mobile lift 100', resetting the lift unit 104 and/or the mobile lift 100', and/or the like.

In some embodiments, the remote control 130 may be a portable electronic device, such as a smartphone, a tablet computing device, a laptop, and/or the like. In such embodiments, the remote control 130 may contain software programming thereon (e.g., an app or the like) that generates an electronic user interface when the software programming is executed. Further, the software programming, when executed, can cause the remote control 130 to complete one or more tasks upon receiving particular inputs from a user via the user interface controls 134. However, it should be understood that the remote control 130 can also be used for other purposes other than those described herein, as is typical for portable electronic devices (e.g., making telephone calls, sending text messages, sending emails, browsing the internet, and/or the like).

In some embodiments, the remote control 130 may be a standalone unit that is particularly used for the purposes described herein. That is, the remote control 130 may solely be used for the purposes of displaying information pertaining to a particular subject, displaying information pertaining to the lift communications system 10 (including components thereof), providing a user input that is usable to control various components, such as the lift unit 104 and/or the mobile lift 100', and/or the like. As such, the remote control 130 may only have software programming that is suitable for the purposes described herein, and may lack programming for executing other processes. Additional details regarding the remote control will be described herein with respect to FIG. 8.

Still referring to FIGS. 1A and 1B, the remote display 140 includes one or more components that provide functionality for providing information pertaining to various components of the lift communications system 10, subjects associated with one or more components of the lift communications system 10, and/or users of one or more components the lift communications system 10. For example, the remote display 140 may include components for displaying a location and/or a status of the rail-mounted lift 100 and/or the mobile lift 100', a location and/or status of the wall-mounted control 120, a location and/or a status of the remote control 130, a subject associated with the rail-mounted lift 100 and/or the mobile lift 100', a user of the rail-mounted lift 100 and/or the mobile lift 100', a user of the wall-mounted control 120, a user of the remote control 130, and/or the like. Accordingly, the remote display 140 may include, for example, a display component 142. The display component 142 is generally any liquid crystal display (LCD), light emitting diode (LED) display, electronic ink (e-ink) display, or the like that can display information to a user. In some embodiments, the display component 142 may be configured as an interactive display that can receive user inputs (e.g., a touch screen display or the like). In some embodiments, the remote display 140 may further include one or more user interface controls (not shown) located on the remote display 140 or peripherally coupled to the remote display 140. The one or more user interface controls may be hardware components that receive inputs from a user and transmit signals corresponding to the inputs. For example, the user interface controls may include, but are not limited to, a touchscreen, a keyboard, a mouse, a joystick, a remote control, a pointing device, a video input device, an audio input device, a haptic feedback device, and/or the like. The display component 142 and/or the one or more user interface controls may be used, for example, to allow a user to interact with the remote display 140 for the purposes of reviewing information pertaining to the components of the lift communications system 10, such as viewing a chart pertaining to a subject, reviewing a mobility score associated with a subject, reviewing the type of components coupled to the rail-mounted lift 100 and/or the mobile lift 100', reviewing data provided by the load sensor 109 and/or the load sensor 193, reviewing data provided by the locating system 111 and/or the locating system 111', reviewing data provided by various other sensors, and/or the like.

The server computing device 150 is generally a computing device that contains components for executing various processes, such as the processes described herein. That is, the server computing device 150 may include at least one or more processing devices and a non-transitory memory component, where the non-transitory memory component includes programming instructions that cause the one or more processing devices to execute the various processes described herein. In some embodiments, the server computing device 150 may include a data storage component that is used for storing data pertaining to the various components of the lift communications system 10 such that the data can be later accessed. In some embodiments, the server computing device 150 may include networking hardware that is used for communicating with the various components of the lift communications system 10. Other components and functionality of the server computing device 150 should generally be understood.

Each of the components of the lift communications system 10 may be positioned inside or outside of the space 103. For example, the embodiments depicted in FIGS. 1A and 1B, the rail-mounted lift 100, the mobile lift 100', the wall-mounted control 120, and the remote control 130 are positioned within the space 103 (e.g., within a subject room in a hospital, an operating room, or the like) while the remote display 140 and the server computing device 150 are located at some location outside the space 103. For example, the remote display 140 may be located elsewhere in a facility containing the space 103, such as at a nurses station, a monitoring area, and/or the like. In a particular embodiment, the remote display 140 may be positioned in a location that is outside a subject room in a facility. In another example, the server computing device 150 may be located elsewhere in a facility containing the space 103, or may be located at an offsite location (e.g., at a server farm or the like).

In some embodiments, various components of the lift communications system 10 may be movable in and out of the space 103, whereas other components of the lift communications system 10 may be fixed in a particular location. For example, in some embodiments, the rail 102 depicted in the embodiment of FIG. 1A may extend both inside and outside of the space 103 such that the carriage 106 can move along the rail to move the lift unit 104 inside and outside of the space 103. That is, the lift unit 104 is movable between various rooms or areas of a facility based on the location of the rail 102. In another example, the casters 185*a*-185*d* on the mobile lift 100' depicted in the embodiment of FIG. 1B may be used to direct (either by remote control or by physically pushing or pulling the mobile lift 100' in or out of the space 103 via the opening 107 or the like). Referring again to both FIGS. 1A and 1B, in another example, the remote control 130 may be movable inside and outside the space 103. For example, a user of the remote control 130 may carry the remote control as the user moves throughout a facility, particularly if the remote control 130 is a software application installed on the user's portable electronic device (e.g., a user's smartphone). Thus, the remote control 130 may be moved in and out of the space 103 as the user moves in and out of the space 103. It should generally be understood that the wall-mounted control 120 may generally be fixed in a position within the space 103, the remote display 140 may be fixed in a position outside of the space 103, and the server computing device 150 may be fixed in a position outside of the space 103. However, the present disclosure is not limited to these configurations, and other configurations are contemplated without departing from the scope of the present disclosure.

Figure 6:
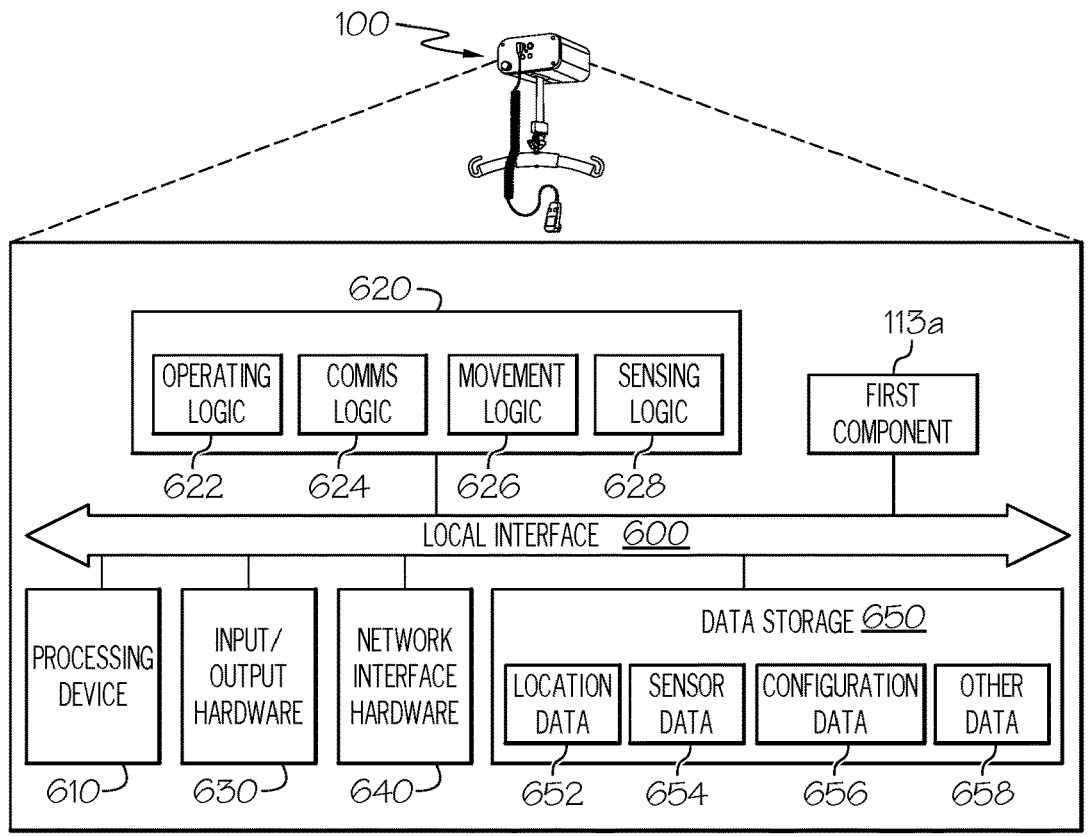
FIG. 6 depicts a block diagram of illustrative internal components within a lift according to one or more embodiments shown and described herein.

FIG. 6 depicts illustrative internal components of the rail-mounted lift 100 that are communicatively coupled to one another to provide the functionality of the rail-mounted lift 100 described herein. However, it should be understood that similar components may also be within the mobile lift 100' (FIG. 1B) without departing from the scope of the present disclosure. Only the internal components of the rail-mounted lift 100 are described for the purposes of brevity. As shown in FIG. 6, the rail-mounted lift 100 may further include a local interface 600 (e.g., a bus) that communicatively interconnects the various components, including, but not limited to, a processing device 610, memory 620, input/output hardware 630, network interface hardware 640, and/or a data storage device 650.

The processing device 610, such as one or more computer processing units (CPU), may be the central processing unit of the rail-mounted lift 100, performing calculations and logic operations required to execute a program. The processing device 610, alone or in conjunction with one or more of the other elements disclosed in FIG. 6, is an illustrative processing device, computing device, processor, or combination thereof, as such terms are used in this disclosure.

The memory 620, such as read only memory (ROM) and random access memory (RAM), may constitute illustrative memory devices (i.e., non-transitory, processor-readable storage media). Such memory 620 may include one or more programming instructions thereon that, when executed by the processing device 610, cause the processing device 610 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media.

In some embodiments, the program instructions contained on the memory 620 may be embodied as a plurality of software modules, where each module provides programming instructions for completing one or more tasks. For example, as shown in FIG. 6, the memory 620 may contain one or more of operating logic 622, communications logic 624, movement logic 626, and sensing logic 628. The operating logic 622 may include an operating system and/or other software for managing components of the rail-mounted lift 100. The communications logic 624 may include programming instructions for facilitating communications between the rail-mounted lift 100 and the various components of the lift communications system 10 (FIG. 1A). The movement logic 626 may generally include programming instructions for receiving movement commands from an external component (e.g., the wall-mounted control 120 and/or the remote control 130 of FIG. 1A) and causing various components of the rail-mounted lift 100 to move the rail-mounted lift 100 as described herein. Still referring to FIG. 6, the sensing logic 628 may generally include programming instructions for directing operation of the locating system 111 (FIG. 1A) or a portion thereof (such as the first component 113a). For example, the sensing logic 628 may direct the first component 113a to turn on/off, to collect data corresponding to the code provided by the second component 113b (FIG. 1A), and/or the like. In some embodiments, one or more of the logic modules of the memory 620 may be a non-volatile memory bank that is separate from the other portions of the memory 620 and is capable of receiving data for upgrading the software of the rail-mounted lift 100, as described in greater detail herein. It should be understood that the various logic modules described herein with respect to FIG. 6 are merely illustrative, and that other logic modules, including logic modules that combine the functionality of two or more of the modules described hereinabove, may be used without departing from the scope of the present application.

Referring to FIGS. 1A and 6, the data storage device 650, which may generally be a storage medium that is separate from the memory 620, may contain a data repository for storing electronic data and/or the like relating to the location of an assembly 101 of the rail-mounted lift 100, an identification of the assembly 101, a sensed code, configuration settings, and/or the like. The data storage device 650 may be any physical storage medium, including, but not limited to, a hard disk drive (HDD), memory, removable storage, and/or the like. While the data storage device 650 is depicted as a local device, it should be understood that the data storage device 650 may be a remote storage device that is remotely located from the rail-mounted lift 100, such as, for example, a server computing device or the like (e.g., the server computing device 150 of FIG. 1A).

Still referring to FIGS. 1A and 6, illustrative data that may be contained within the data storage device 650 may include, for example, location data 652, sensor data 654, configuration data 656, and/or other data 658. Location data 652 may include, for example, information pertaining to a location and/or an identity of the rail-mounted lift 100, such as a code corresponding to the last stored location of the rail-mounted lift 100 or the like. The sensor data 654 may include, for example, data relating to information that is sensed by the receiver of the locating system 111 of FIG. 1A (e.g., the first component 113a or the second component 113b), including a code that is usable by a server computing device (e.g., the server computing device 150 of FIG. 1A) to identify the location of the rail-mounted lift 100, a code that is usable by a server computing device (e.g., the server computing device 150 of FIG. 1A) to identify an associated subject, a code that is usable by a server computing device (e.g., the server computing device 150 of FIG. 1A) to identify an associated user, and/or the like. The configuration data 656 may include, for example, data relating to configuring the rail-mounted lift 100 such that the rail-mounted lift 100 can be communicatively coupled to a remote server (e.g., the server computing device 150 of FIG. 1A), as described in greater detail herein.

Still referring to FIGS. 1A and 6, the input/output hardware 630 may generally include hardware contained within the hand control unit 112 (if the assembly 101 is equipped with a hand control unit 112). That is, the display 114 and/or the one or more user interface controls 116 may be communicatively coupled to or may represent a portion of the input/output hardware 630 such that one or more user inputs received via the display 114 and/or the one or more user interface controls 116 are transmitted via the input/output hardware 630 and one or more outputs to be displayed to the user are transmitted to the display 114 via the input/output hardware 630. In some embodiments, the sensing device 117 may also be communicatively coupled to the input/output hardware 630 such that data corresponding to a sensed code (e.g., image data containing a sensed code) are transmitted via the input/output hardware 630.

The network interface hardware 640 may generally provide the rail-mounted lift 100 with an ability to interface with one or more external components, such as, for example, the wall-mounted control 120, the remote control 130, the remote display 140, the server computing device 150, and/or the like. Communication with external devices may occur using various communication ports (not shown). An illustrative communication port may be attached to a communications network, such as the Internet, an intranet, a local network, a direct connection, and/or the like, such as the various networks described herein with respect to FIGS. 10A-10C.

Referring again to FIG. 6, it should be understood that in some embodiments, the input/output hardware 630 and the network interface hardware 640 may be combined into a single device that allows for communications with other devices, regardless of whether such other devices are located within the rail-mounted lift 100.

It should be understood that the components illustrated in FIG. 6 are merely illustrative and are not intended to limit the scope of this disclosure. More specifically, while the components in FIG. 6 are illustrated as residing within the rail-mounted lift 100, this is a nonlimiting example. In some embodiments, one or more of the components may reside external to rail-mounted lift 100. Similarly, one or more of the components may be embodied in other devices not specifically described herein.

Figure 7:
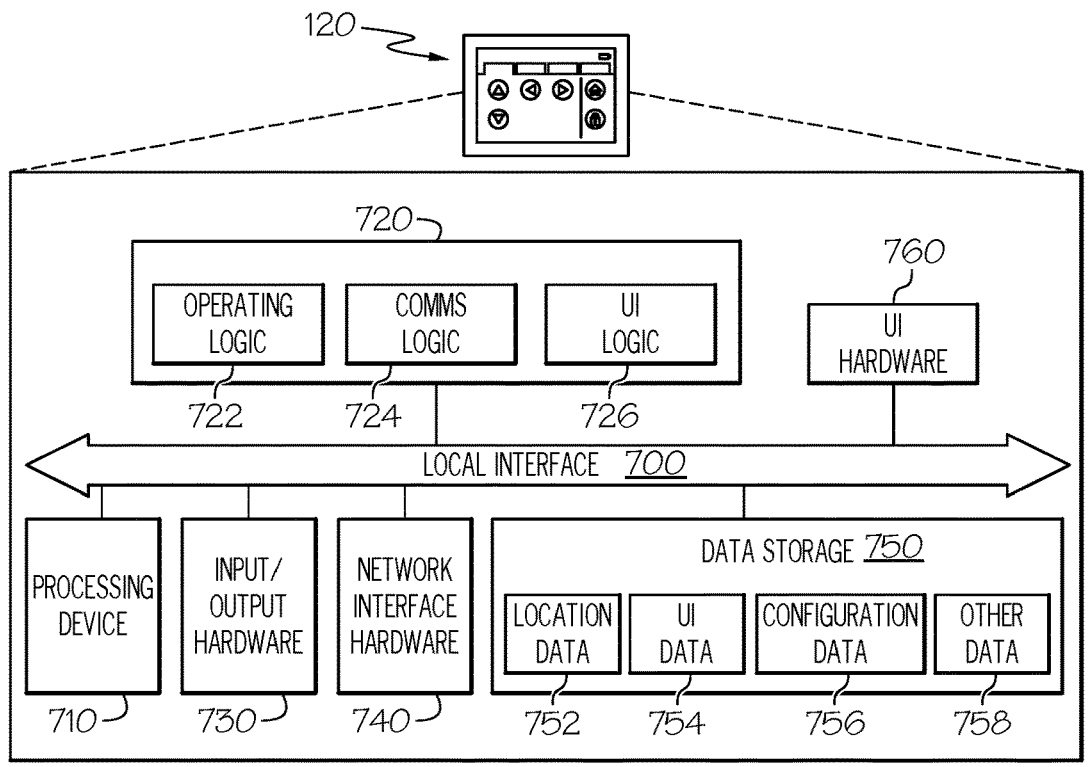
FIG. 7 depicts a block diagram of illustrative internal components within wall-mounted control of a rail-mounted lift according to one or more embodiments shown and described herein.

FIG. 7 depicts illustrative internal components of the wall-mounted control 120 that are communicatively coupled to one another to provide the functionality described herein. As shown in FIG. 7, the wall-mounted control 120 may further include a local interface 700 (e.g., a bus) that communicatively interconnects the various components, including, but not limited to, a processing device 710, memory 720, input/output hardware 730, network interface hardware 740, a data storage device 750, and/or UI hardware 760.

The processing device 710, such as one or more computer processing units (CPU), may be the central processing unit of the wall-mounted control 120, performing calculations and logic operations required to execute a program. The processing device 710, alone or in conjunction with one or more of the other elements disclosed in FIG. 7, is an illustrative processing device, computing device, processor, or combination thereof, as such terms are used in this disclosure.

The memory 720, such as read only memory (ROM) and random access memory (RAM), may constitute illustrative memory devices (i.e., non-transitory, processor-readable storage media). Such memory 720 may include one or more programming instructions thereon that, when executed by the processing device 710, cause the processing device 710 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media. In some embodiments, the memory 720 may be partitioned into a plurality of logic banks, where each logic bank is used for a particular use. For example, in some embodiments, a first partition may contain a logic bank specifically used for operating the wall-mounted control 120 (e.g., containing the logic modules described herein) and a second partition may contain a logic bank used for executing software update programming. Such partitions may be separated to facilitate updating of software without rebooting the wall-mounted control 120 during operation and risking downtime associated with a reboot and update.

In some embodiments, the program instructions contained on the memory 720 may be embodied as a plurality of software modules, where each module provides programming instructions for completing one or more tasks. For example, as shown in FIG. 7, the memory 720 may contain one or more of operating logic 722, communications logic 724, and UI logic 726. The operating logic 722 may include an operating system and/or other software for managing components of the wall-mounted control 120. The communications logic 724 may include programming instructions for facilitating communications between the wall-mounted control 120 and the various components of the lift communications system 10 (FIGS. 1A-1B). Still referring to FIG. 7, the UI logic 726 may generally include programming instructions for providing a user interface to a user via the wall-mounted control 120, as well as programming instructions for receiving user inputs via the user interface. It should be understood that the various logic modules described herein with respect to FIG. 7 are merely illustrative, and that other logic modules, including logic modules that combine the functionality of two or more of the modules described hereinabove, may be used without departing from the scope of the present application.

The data storage device 750, which may generally be a storage medium that is separate from the memory 720, may contain a data repository for storing electronic data and/or the like relating to the location of the wall-mounted control 120, an identification of the wall-mounted control 120, configuration settings, UI data, and/or the like. The data storage device 750 may be any physical storage medium, including, but not limited to, a hard disk drive (HDD), memory, removable storage, and/or the like. While the data storage device 750 is depicted as a local device, it should be understood that the data storage device 750 may be a remote storage device that is remotely located from the wall-mounted control 120, such as, for example, a server computing device or the like. In some embodiments, the data storage device 750 may be partitioned into a plurality of data banks, where each data bank is used for a particular use. For example, in some embodiments, a first partition may contain a data bank used for operating the wall-mounted control 120 and a second partition may contain a data bank used for receiving software updates. Such partitions may be separated to facilitate updating of software without rebooting the wall-mounted control 120 during operation and risking downtime associated with a reboot and update.

Illustrative data that may be contained within the data storage device 750 may include, for example, location data 752, UI data 754, configuration data 756, and/or other data 758. The location data 752 is generally data pertaining to a location of the wall-mounted control 120. The UI data is generally data pertaining to the user interface, such as user interface elements, logs of what users have entered via the user interface, and/or the like. The configuration data 756 generally contains data pertaining to how the wall-mounted control 120 is configured, including, but not limited to, information pertaining to a particular room or space in which the wall-mounted control 120 is mounted, information pertaining to paired devices (e.g., the rail-mounted lift 100 and/or the remote control 130), information pertaining to a subject associated with the wall-mounted control 120 (e.g., a subject assigned to the room in which the wall-mounted control 120 is located), and/or the like.

Referring to FIGS. 1A-1B and 7, the input/output hardware 730 may generally include hardware contained within the wall-mounted control 120. That is, the display 122 and/or the one or more user interface controls 124 may be encompassed by the input/output hardware 730 and communicatively coupled to the local interface 400 such that one or more user inputs received via the display 122 and/or the one or more user interface controls 124 are transmitted via the local interface 700 and one or more outputs to be displayed to the user are transmitted to the display 122 via the local interface 700.

Still referring to FIGS. 1A-1B and 7, the network interface hardware 740 may generally provide the wall-mounted control 120 with an ability to interface with one or more external components, such as, for example, the rail-mounted lift 100 and/or components thereof (e.g., the assembly 101), the mobile lift 100' and/or components thereof, the remote control 130, and/or the like. Communication with external devices may occur using various communication ports (not shown). An illustrative communication port may be attached to a communications network, such as the Internet, an intranet, a local network, a direct connection, and/or the like.

It should be understood that in some embodiments, the input/output hardware 730 and the network interface hardware 740 may be combined into a single device that allows for communications with other devices, regardless of whether such other devices are located within the wall-mounted control 120.

Still referring to FIGS. 1A-1B and 7, the UI hardware 760 may generally be one or more hardware components that provide a user interface to a user. Illustrative components include, but are not limited to, the display 122 and/or the one or more user interface controls 124.

It should be understood that the components illustrated in FIG. 7 are merely illustrative and are not intended to limit the scope of this disclosure. More specifically, while the components in FIG. 7 are illustrated as residing within the wall-mounted control 120, this is a nonlimiting example. In some embodiments, one or more of the components may reside external to the wall-mounted control 120. Similarly, one or more of the components may be embodied in other devices not specifically described herein.

Figure 8:
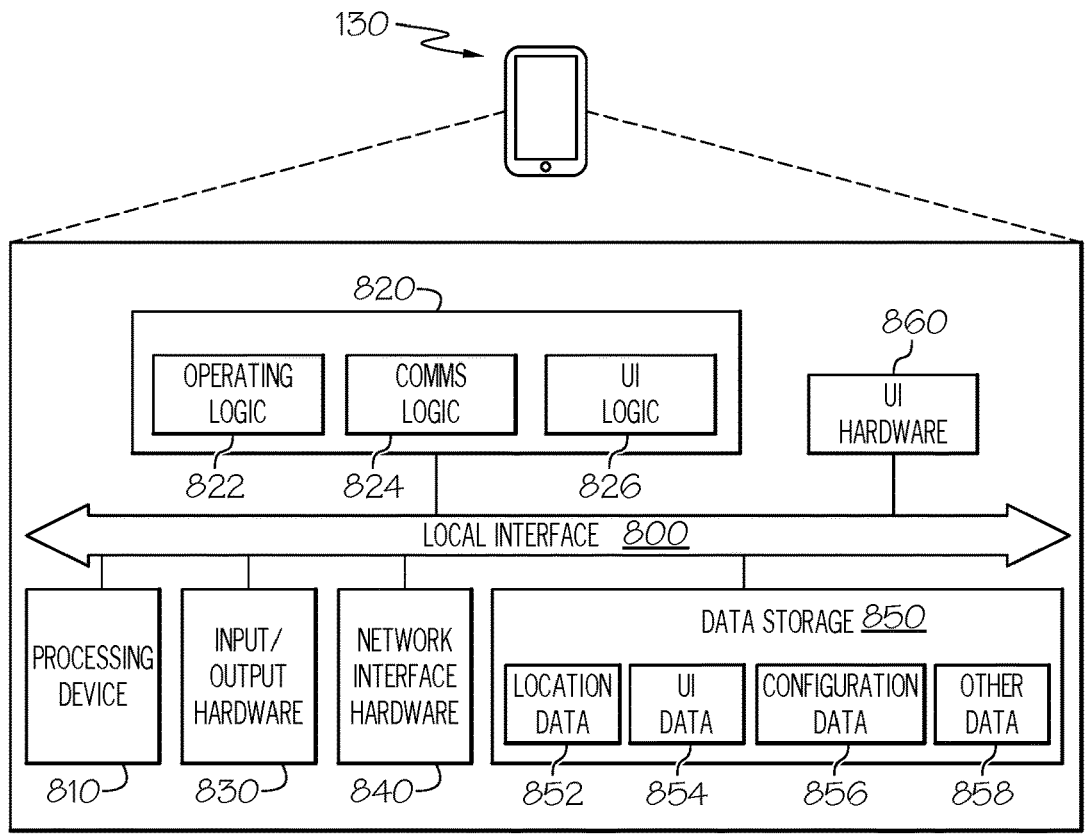
FIG. 8 depicts a block diagram of illustrative internal components within a remote control according to one or more embodiments shown and described herein.

FIG. 8 depicts illustrative internal components of the remote control 130 that are communicatively coupled to one another to provide the functionality described herein. As shown in FIG. 8, the remote control 130 may further include a local interface 800 (e.g., a bus) that communicatively interconnects the various components, including, but not limited to, a processing device 810, memory 820, input/output hardware 830, network interface hardware 840, a data storage device 850, and/or UI hardware 860.

The processing device 810, such as one or more computer processing units (CPU), may be the central processing unit of the remote control 130, performing calculations and logic operations required to execute a program. The processing device 810, alone or in conjunction with one or more of the other elements disclosed in FIG. 8, is an illustrative processing device, computing device, processor, or combination thereof, as such terms are used in this disclosure.

The memory 820, such as read only memory (ROM) and random access memory (RAM), may constitute illustrative memory devices (i.e., non-transitory, processor-readable storage media). Such memory 820 may include one or more programming instructions thereon that, when executed by the processing device 810, cause the processing device 810 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media. In some embodiments, the memory 820 may be partitioned into a plurality of logic banks, where each logic bank is used for a particular use. For example, in some embodiments, a first partition may contain a logic bank specifically used for operating the remote control 130 (e.g., containing the logic modules described herein) and a second partition may contain a logic bank used for executing software update programming. Such partitions may be separated to facilitate updating of software without rebooting the remote control 130 during operation and risking downtime associated with a reboot and update.

In some embodiments, the program instructions contained on the memory 820 may be embodied as a plurality of software modules, where each module provides programming instructions for completing one or more tasks. For example, as shown in FIG. 8, the memory 820 may contain one or more of operating logic 822, communications logic 824, and UI logic 826. The operating logic 822 may include an operating system and/or other software for managing components of the remote control 130. The communications logic 824 may include programming instructions for facilitating communications between the remote control 130 and the various components of the lift communications system 10 (FIGS. 1A-1B). The UI logic 826 may generally include programming instructions for providing a user interface to a user via the remote control 130, as well as programming instructions for receiving user inputs via the user interface. It should be understood that the various logic modules described herein with respect to FIG. 8 are merely illustrative, and that other logic modules, including logic modules that combine the functionality of two or more of the modules described hereinabove, may be used without departing from the scope of the present application.

Still referring to FIG. 8, the data storage device 850, which may generally be a storage medium that is separate from the memory 820, may contain a data repository for storing electronic data and/or the like relating to the location of the remote control 130, an identification of the remote control 130, configuration settings, UI data, and/or the like. The data storage device 850 may be any physical storage medium, including, but not limited to, a hard disk drive (HDD), memory, removable storage, and/or the like. While the data storage device 850 is depicted as a local device, it should be understood that the data storage device 850 may be a remote storage device that is remotely located from the remote control 130, such as, for example, a server computing device or the like. In some embodiments, the data storage device 850 may be partitioned into a plurality of data banks, where each data bank is used for a particular use. For example, in some embodiments, a first partition may contain a data bank used for operating the remote control 130 and a second partition may contain a data bank used for receiving software updates. Such partitions may be separated to facilitate updating of software without rebooting the remote control 130 during operation and risking downtime associated with a reboot and update.

Illustrative data that may be contained within the data storage device 850 may include, for example, location data 852, UI data 854, configuration data 856, and/or other data 858. The location data 852 is generally data pertaining to a location of the remote control 130, including a location history of the remote control 130. The UI data is generally data pertaining to the user interface, such as user interface elements, logs of what users have entered via the user interface, and/or the like. The configuration data 856 generally contains data pertaining to how the remote control 130 is configured, including, but not limited to, information pertaining to a particular room or space in which the remote control 130 is used, information pertaining to paired devices (e.g., the rail-mounted lift 100, the remote lift 100' (FIG. 1B), and/or the wall-mounted control 120), information pertaining to a subject associated with the remote control 130 (e.g., a subject assigned to the room in which the remote control 130 is located at a particular point in time), and/or the like.

Referring to FIGS. 1A-B and 8, the input/output hardware 830 may generally include hardware contained within the remote control 130. That is, the display 132 and/or the one or more user interface controls 134 may be encompassed as the input/output hardware 830 and communicatively coupled to the local interface 800 such that one or more user inputs received via the display 132 and/or the one or more user interface controls 134 are transmitted via the local interface 800 and one or more outputs to be displayed to the user are transmitted to the display 132 via the local interface 800.

Referring to FIGS. 1A-1B, and 8, the network interface hardware 840 may generally provide the remote control 130 with an ability to interface with one or more external components, such as, for example, the rail-mounted lift 100 and/or components thereof (e.g., the assembly 101), the mobile lift 100' and/or components thereof, the wall-mounted control 120, and/or the like. Communication with external devices may occur using various communication ports (not shown). An illustrative communication port may be attached to a communications network, such as the Internet, an intranet, a local network, a direct connection, and/or the like.

It should be understood that in some embodiments, the input/output hardware 830 and the network interface hardware 840 may be combined into a single device that allows for communications with other devices, regardless of whether such other devices are located within the wall-mounted control.

Referring again to FIGS. 1A-1B and 8, the UI hardware 860 may generally be one or more hardware components that provide a user interface to a user. Illustrative components include, but are not limited to, the display 132 and/or the one or more user interface controls 134.

It should be understood that the components illustrated in FIG. 8 are merely illustrative and are not intended to limit the scope of this disclosure. More specifically, while the components in FIG. 8 are illustrated as residing within the remote control 130, this is a nonlimiting example. In some embodiments, one or more of the components may reside external to the remote control 130. Similarly, one or more of the components may be embodied in other devices not specifically described herein.

Figure 9:
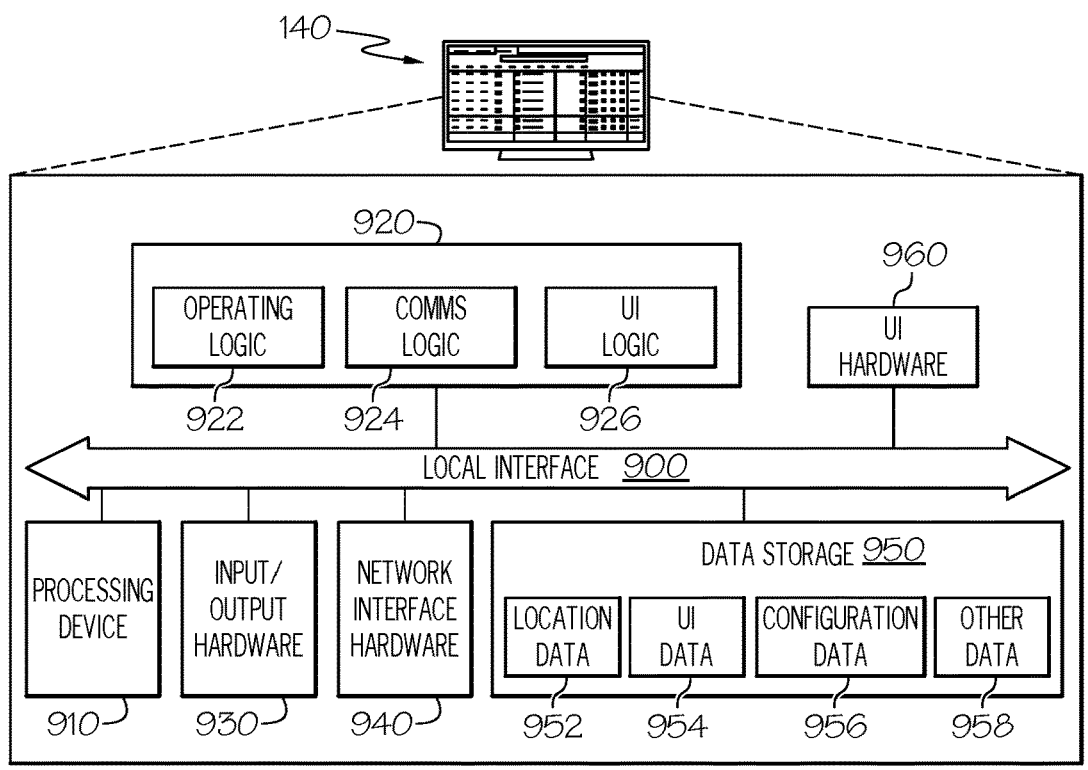
FIG. 9 depicts a block diagram of illustrative internal components within a remote display according to one or more embodiments shown and described herein.

FIG. 9 depicts illustrative internal components of the remote display 140 that are communicatively coupled to one another to provide the functionality described herein. As shown in FIG. 9, the remote display 140 may further include a local interface 900 (e.g., a bus) that communicatively interconnects the various components, including, but not limited to, a processing device 910, memory 920, input/ output hardware 930, network interface hardware 940, a data storage device 950, and/or UI hardware 960.

The processing device 910, such as one or more computer processing units (CPU), may be the central processing unit of the remote display 140, performing calculations and logic operations required to execute a program. The processing device 910, alone or in conjunction with one or more of the other elements disclosed in FIG. 9, is an illustrative processing device, computing device, processor, or combination thereof, as such terms are used in this disclosure.

The memory 920, such as read only memory (ROM) and random access memory (RAM), may constitute illustrative memory devices (i.e., non-transitory, processor-readable storage media). Such memory 920 may include one or more programming instructions thereon that, when executed by the processing device 910, cause the processing device 910 to complete various processes, such as the processes described herein. Optionally, the program instructions may be stored on a tangible computer-readable medium such as a digital disk, flash memory, a memory card, a USB drive, an optical disc storage medium (e.g., Blu-ray™, CD, DVD), and/or other non-transitory processor-readable storage media.

In some embodiments, the program instructions contained on the memory 920 may be embodied as a plurality of software modules, where each module provides programming instructions for completing one or more tasks. For example, as shown in FIG. 9, the memory 920 may contain one or more of operating logic 922, communications logic 924, and UI logic 926. The operating logic 922 may include an operating system and/or other software for managing components of the remote display 140. The communications logic 924 may include programming instructions for facilitating communications between the remote display 140 and the various components of the lift communications system 10 (FIGS. 1A-1B). The UI logic 926 may generally include programming instructions for providing a user interface to a user via the remote display 140, as well as programming instructions for receiving user inputs via the user interface. It should be understood that the various logic modules described herein with respect to FIG. 9 are merely illustrative, and that other logic modules, including logic modules that combine the functionality of two or more of the modules described hereinabove, may be used without departing from the scope of the present application.

Still referring to FIG. 9, the data storage device 950, which may generally be a storage medium that is separate from the memory 920, may contain a data repository for storing electronic data and/or the like relating to the location of the remote display 140, an identification of the remote display 140, configuration settings, UI data, and/or the like. The data storage device 950 may be any physical storage medium, including, but not limited to, a hard disk drive (HDD), memory, removable storage, and/or the like. While the data storage device 950 is depicted as a local device, it should be understood that the data storage device 950 may be a remote storage device that is remotely located from the remote display 140, such as, for example, a server computing device or the like.

Illustrative data that may be contained within the data storage device 950 may include, for example, location data 952, UI data 954, configuration data 956, and/or other data 958. The location data 952 is generally data pertaining to a location of the remote display 140. The UI data is generally data pertaining to any user interface that may be present in the remote display 140, such as user interface elements, logs of what users have entered via the user interface, and/or the like. The configuration data 956 generally contains data pertaining to how the remote display 140 is configured, including, but not limited to, information pertaining to particular rooms or spaces in which the remote display 140 is associated, particular rooms or spaces in which the remote display 140 is configured to monitor, and/or the like.

Referring to FIGS. 1A-1B and 9, the input/output hardware 930 may generally include hardware contained within the remote display 140. That is, the display component 142 and/or one or more user interface controls may be encompassed as the input/output hardware 930 such that one or more user inputs received via the display component 142 and/or the one or more user interface controls are transmitted via the local interface 900 and one or more outputs to be displayed to the user are transmitted to the display component 142 via the local interface 900.

Still referring to FIGS. 1A-1B and 9, the network interface hardware 940 may generally provide the remote display 140 with an ability to interface with one or more external components, such as, for example, the rail-mounted lift 100 and/or components thereof (e.g., the assembly 101), the mobile lift 100' and/or components thereof, the wall-mounted control 120, the remote control 130, and/or the like. Communication with external devices may occur using various communication ports (not shown). An illustrative communication port may be attached to a communications network, such as the Internet, an intranet, a local network, a direct connection, and/or the like.

It should be understood that in some embodiments, the input/output hardware 930 and the network interface hardware 940 may be combined into a single device that allows for communications with other devices, regardless of whether such other devices are located within the wall-mounted control 120.

Still referring to FIGS. 1A-1B and 9, the UI hardware 960 may generally be one or more hardware components that provide a user interface to a user. Illustrative components include, but are not limited to, the display component 142 and/or the one or more user interface controls.

It should be understood that the components illustrated in FIG. 9 are merely illustrative and are not intended to limit the scope of this disclosure. More specifically, while the components in FIG. 9 are illustrated as residing within the remote display 140, this is a nonlimiting example. In some embodiments, one or more of the components may reside external to the remote display 140. Similarly, one or more of the components may be embodied in other devices not specifically described herein.

The interconnectivity of the various components depicted in FIGS. 1A and 1B may vary. That is, in certain embodiments, the interconnectivity of the various components may be in one configuration whereas in other embodiments, the interconnectivity of the various components may be in another configuration. Three illustrative configurations are depicted in FIGS. 10A-10C.

FIG. 10A depicts one embodiment of the interconnectivity of the various components of the lift communications system 10 (FIGS. 1A-1B) whereby all of the components are communicatively interconnected via a network 11. As illustrated in FIG. 10A, the network 11 may include a wide area network (WAN), such as the Internet, a local area network (LAN), a mobile communications network, a public service telephone network (PSTN), a personal area network (PAN), a metropolitan area network (MAN), a virtual private network (VPN), and/or another network. The network 11 may generally be configured to electronically connect one or more of the components of the lift communications system 10 (FIGS. 1A-1B), including, but not limited to, the rail-mounted lift 100, the mobile lift 100', the wall-mounted control 120, the remote control 130, the remote display 140, and/or the server computing device 150. Other components, such as other computing devices, data repositories, or the like, may also be coupled to the network 11 in some embodiments.

Figure 10B:
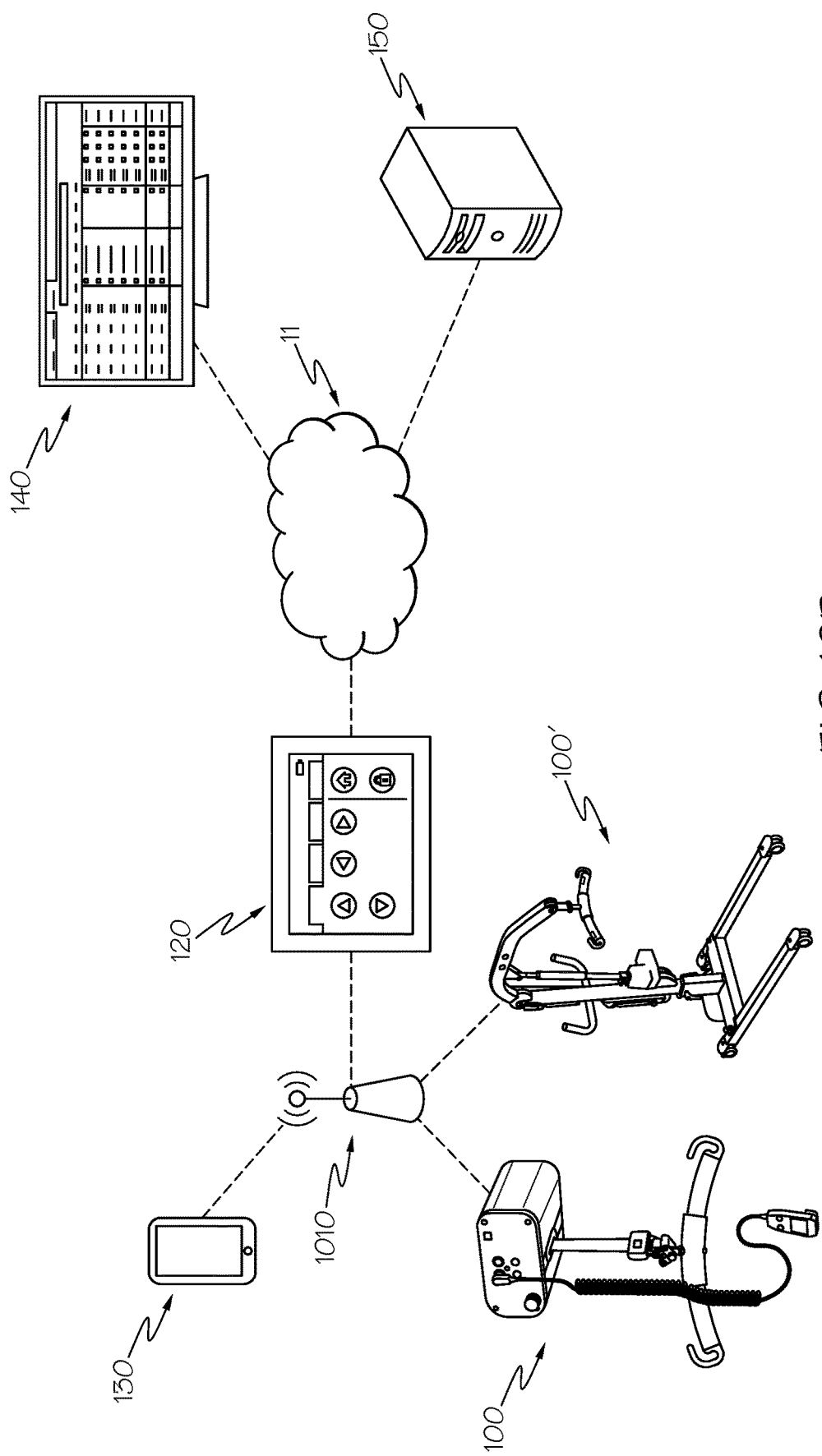
FIG. 10B schematically depicts another illustrative lift communications network according to one or more embodiments shown and described herein.

FIG. 10B depicts another embodiment of the interconnectivity of the various components of the lift communications system 10 (FIGS. 1A-1B) whereby certain components are communicatively coupled via a direct connection to one another and others are communicatively interconnected via the network 11. More specifically, as shown in the embodiment of FIG. 10B, the wall-mounted control 120 may act as a hub or a gateway to the network 11 for various other components, such as the rail-mounted lift 100, the mobile lift 100' and/or the remote control 130. That is, the rail-mounted lift 100, the mobile lift 100' and/or the remote control 130 may be communicatively coupled via an access point 1010 or the like that provides access to the wall-mounted control 120. Further access to the network 11 (and consequently the remote display 140 and/or the server computing device 150) may be granted by the wall-mounted control 120 for the rail-mounted lift 100, the mobile lift 100', and/or the remote control 130 in some embodiments. In some embodiments, the remote control 130 may act as a remote of the wall-mounted control 120, containing the same functionality and displaying the same user interfaces as the wall-mounted control 120 such that a user may use the wall-mounted control 120 without having to be physically present at the wall-mounted control 120. That is, the remote control 130 may act as a "master" device controlling the "slave" wall-mounted control 120 in such embodiments. In the embodiment depicted in FIG. 10B, the remote control 130 may be configured to control the rail-mounted lift 100 and/or the mobile lift 100' on its own or via the wall-mounted control 120 by transmitting signals to and receiving signals from the access point 1010.

Figure 10C:
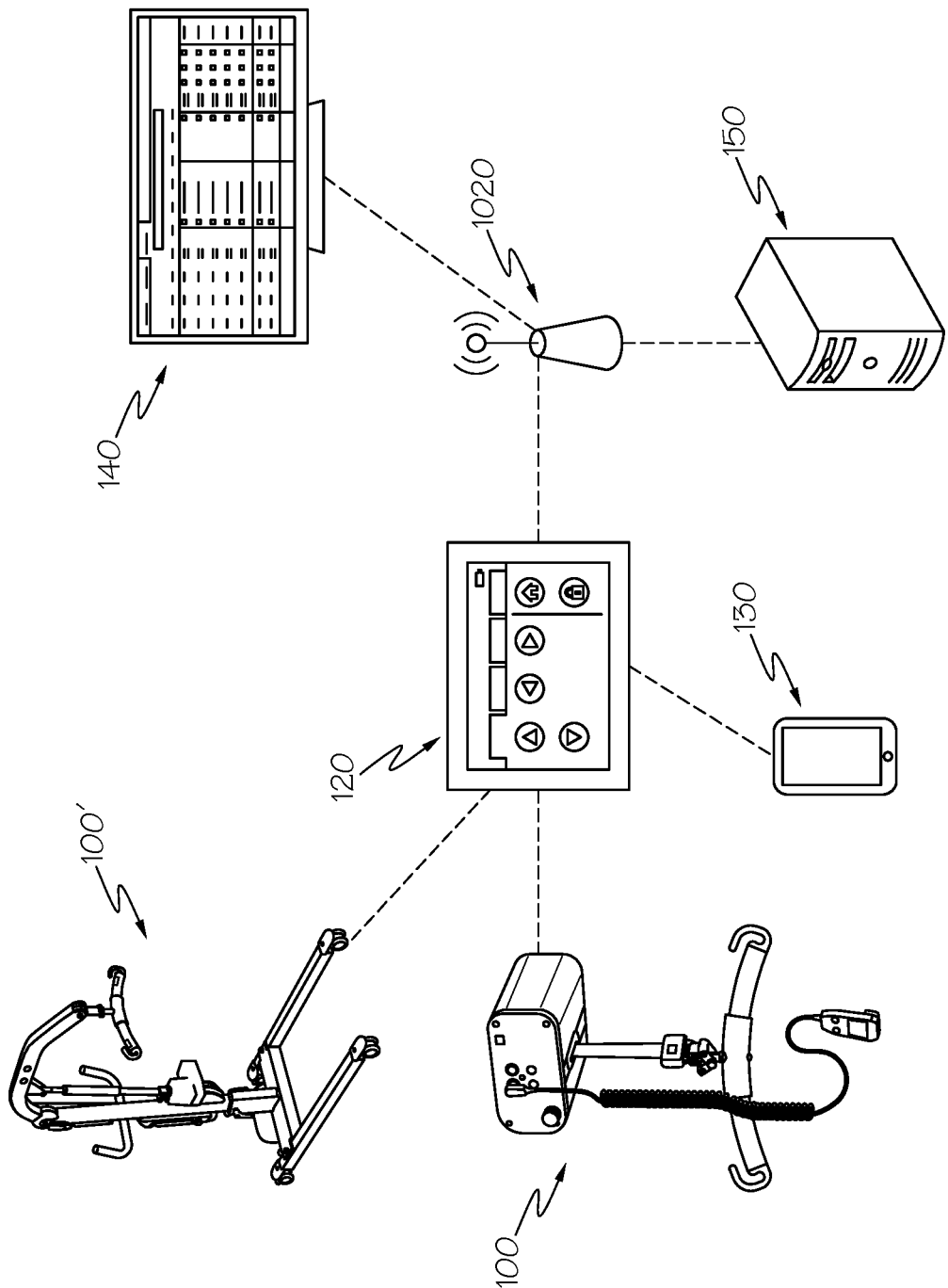
FIG. 10C schematically depicts an illustrative direct connectivity of components in a lift according to one or more embodiments shown and described herein.

FIG. 10C depicts another embodiment of the interconnectivity of the various components of the lift communications system 10 (FIGS. 1A-1B) whereby all components are communicatively coupled via a direct connection to one another. More specifically, as shown in the embodiment of FIG. 10C, the wall-mounted control 120 may act as a hub for various other components, such as the rail-mounted lift 100, the mobile lift 100' and/or the remote control 130. That is, the rail-mounted lift 100, the mobile lift 100' and/or the remote control 130 may be communicatively coupled directly to the wall-mounted control 120 (e.g., via a wireless connection such as 802.11x, Bluetooth, or the like). In addition, the remote display 140 and/or the server computing device 150 may be communicatively coupled via an access point 1020 to the wall-mounted control 120. Further access to the remote display 140 and/or the server computing device 150 may be granted by the wall-mounted control 120 for the rail-mounted lift 100, the mobile lift 100', and/or the remote control 130 in some embodiments. In some embodiments, the remote control 130 may act as a remote of the wall-mounted control 120, containing the same functionality and displaying the same user interfaces as the wall-mounted control 120 such that a user may use the wall-mounted control 120 without having to be physically present at the wall-mounted control 120. That is, the remote control 130 may act as a "master" device controlling the "slave" wall-mounted control 120 in such embodiments. In the embodiment depicted in FIG. 10C, the remote control 130 may be configured to control the rail-mounted lift 100 and/or the mobile lift 100' on its own or via the wall-mounted control 120 by transmitting signals to and receiving signals from the wall-mounted control 120.

It should be understood that the various interconnectivity of components depicted in FIGS. 10A-10C is not all encompassing, and other configurations are contemplated and within the scope of the present disclosure. In some embodiments, certain components may be communicatively coupled via a direct connection with one another. For example, the remote display 140 may be communicatively coupled to the rail mounted lift 100 and/or the mobile lift 100' via a direct connection such that data is directly transmitted between the remote display and the rail mounted lift 100 and/or the mobile lift 100'. In some embodiments, the remote display 140 may be communicatively coupled to the server computing device 150 via a direct connection.

Figure 12:
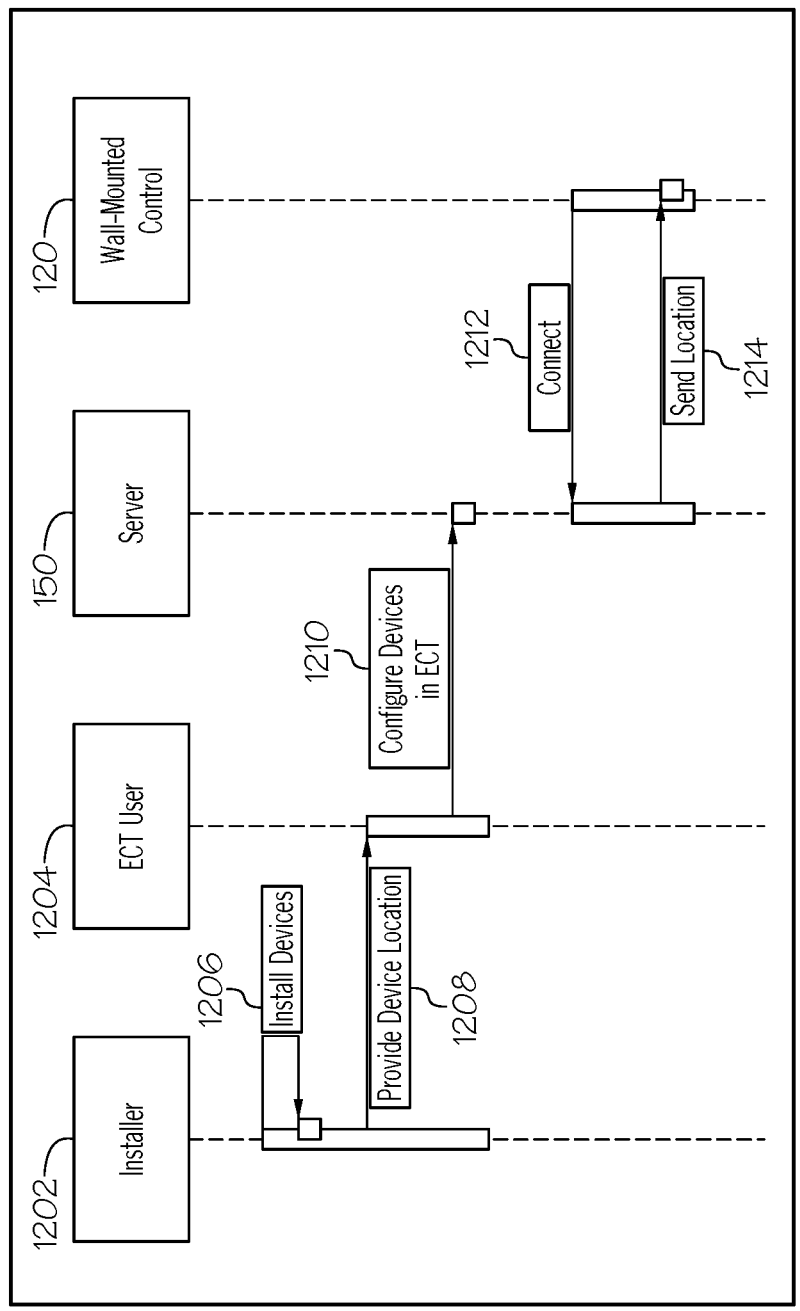
FIG. 12 depicts a flow diagram of an illustrative process for establishing a location of various components according to one or more embodiments shown and described herein.
Figure 13:
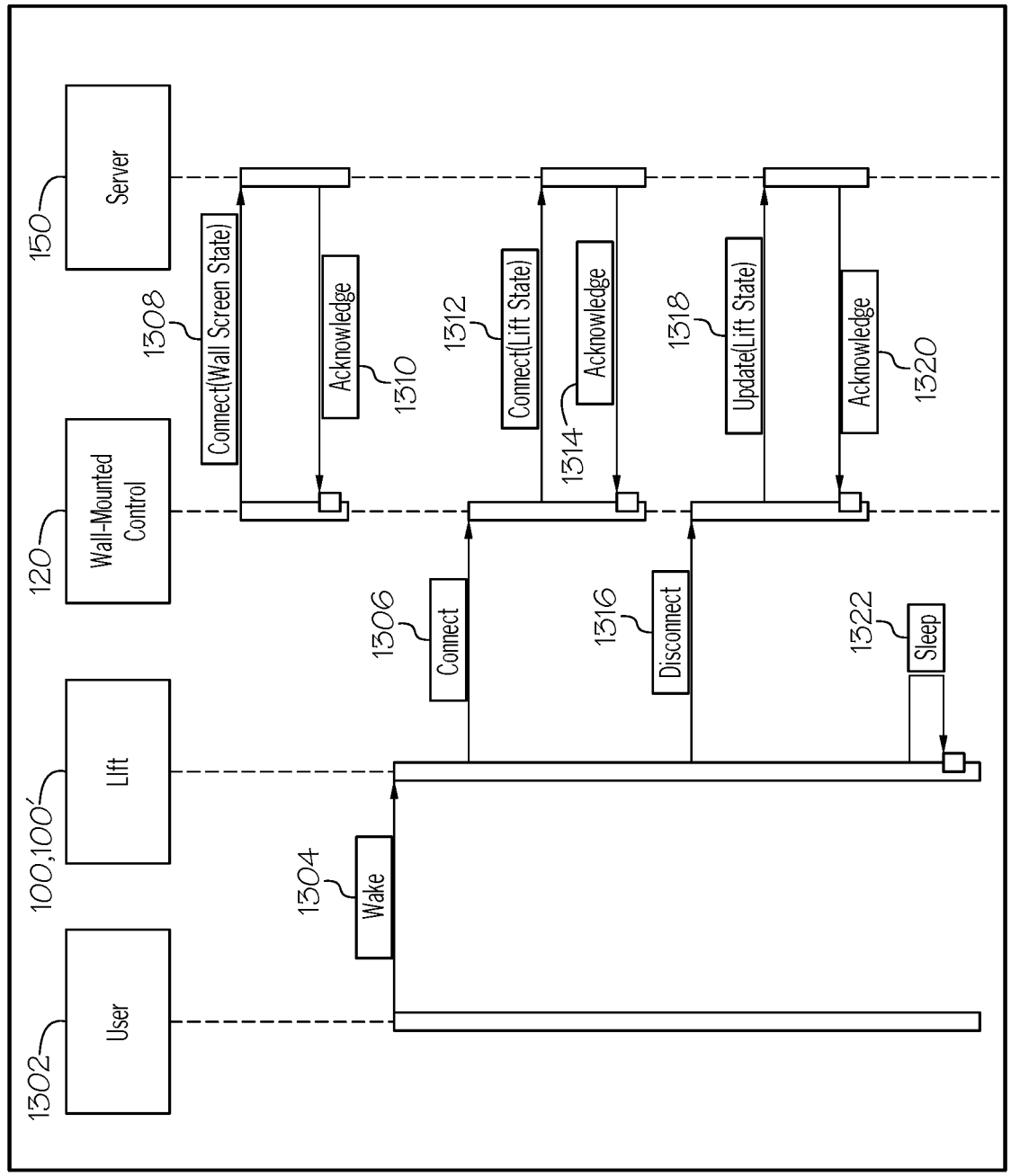
FIG. 13 depicts a flow diagram of an illustrative device connection process according to one or more embodiments shown and described herein.
Figure 14:
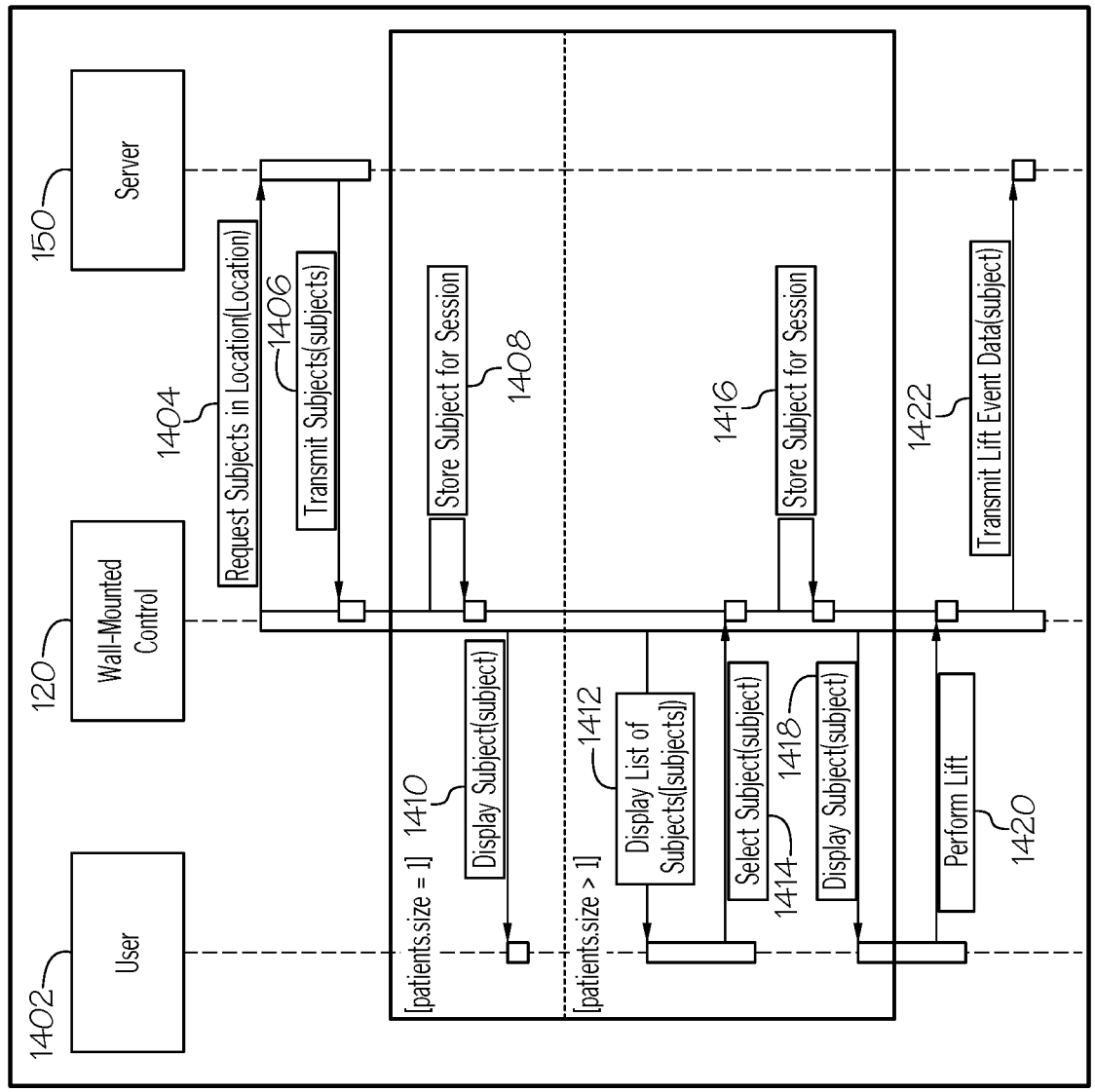
FIG. 14 depicts a flow diagram of an illustrative subject association process according to one or more embodiments shown and described herein.
Figure 15:
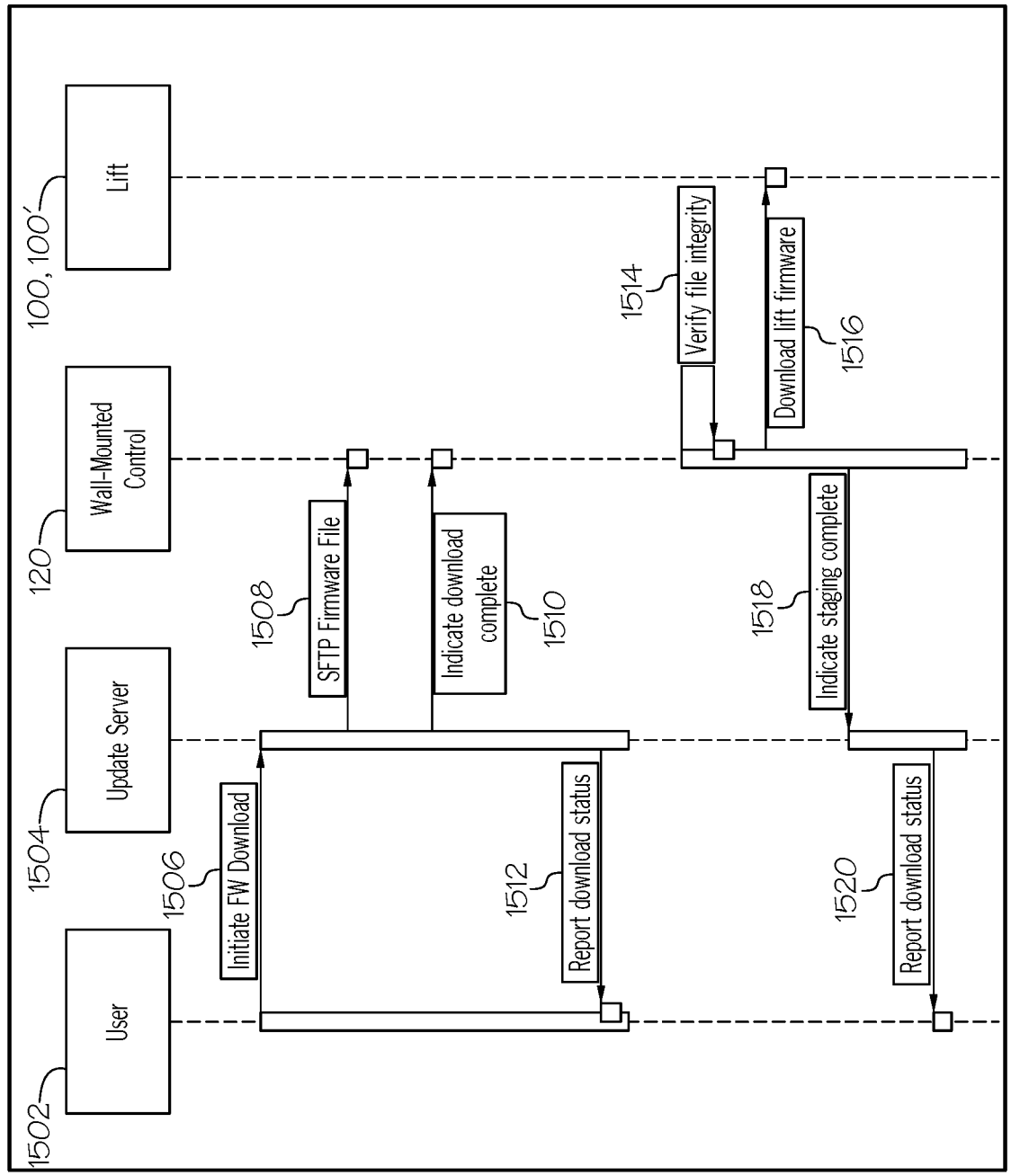
FIG. 15 depicts a flow diagram of an illustrative firmware update process according to one or more embodiments shown and described herein.

The interconnectivity of components of the lift communications system 10 allows for particular communications for the purposes of configuring and using the various components of the lift communications system 10 described herein. For example, the various components may be initially set up as depicted in FIG. 11, configured for location as depicted in FIG. 12, waking the rail-mounted lift 100, the mobile lift 100', and/or other components as depicted in FIG. 13, selecting a subject as depicted in FIG. 14, and/or updating firmware or other software as depicted in FIG. 15.

Figure 11:
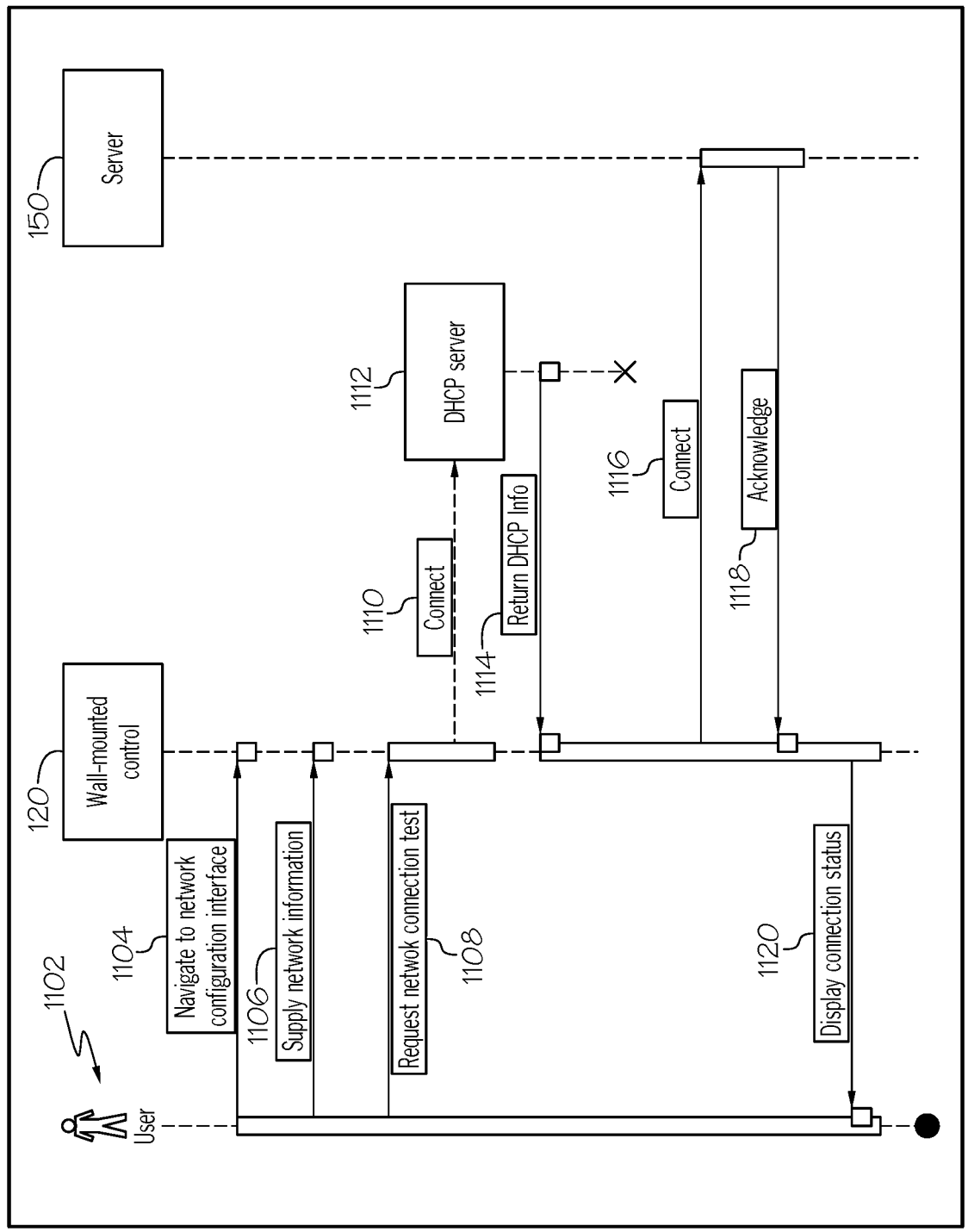
FIG. 11 depicts a flow diagram of an illustrative verifying or displaying a network configuration between connected components according to one or more embodiments shown and described herein.

FIG. 11 depicts a flow diagram of a process of verifying a network configuration between devices according to various embodiments. In the embodiment depicted in FIG. 11, the network configuration determination process may be completed by a user 1102 interacting with the wall-mounted control 120 in order to verify a network connection of the wall-mounted control 120 with various other components, such as a network, the server computing device 150, and/or the like. However, it should be understood that such an embodiment is merely illustrative, and other methods and configurations for completing such a network configuration determination process are contemplated. Furthermore, while the steps depicted with respect to FIG. 11 generally relate to a verification of a network connection of the wall-mounted control 120, this is also illustrative. A similar process may also be completed for each of the components of the lift communications system 10 without departing from the scope of the present disclosure.

Referring to FIGS. 1A-1B and 11, at block 1104, the user 1102 navigates to a network configuration interface portion of a user interface. In embodiments, the network configuration interface may be part of a user interface at the wall-mounted control 120, a user interface at the remote control 130, and/or the like. That is, the user 1102 utilizes the various components of the wall-mounted control 120 and/or the remote control 130 to navigate to the network configuration interface. For example, the user 1102 may utilize the display 122 and/or the one or more user interface controls 124 of the wall-mounted control 120 to navigate to the network configuration interface. In another example, the user 1102 may utilize the display 132 and/or the one or more user interface controls 134 of the remote control 130 to navigate to the network configuration interface. In embodiments where the user 1102 utilizes a device other than the wall-mounted control 120 (e.g., the remote control 130), information may be transmitted to the wall-mounted control 120 via a direct connection to the wall-mounted control 120 (e.g., a direct connection between the remote control 130) for use in configuring the wall-mounted control for a network.

At block 1106, the user 1102 supplies the network information via the network configuration interface. That is, the user 1102 supplies information pertaining to the network to which the wall-mounted control 120 is to connect. In some embodiments, supplying the network information may include manually entering information that identifies a desired network, such as entering a service set identifier (SSID), an internet protocol (IP) address, a media access control (MAC) address, or the like. In other embodiments, supplying the network information may include supplying a code or the like (e.g., a barcode, 3D code, etc.) that contains information pertaining to a particular network to be connected. For example, the user may use the remote control 130 to scan a code that is decodable to obtain information pertaining to the network to which the wall-mounted control 120 is to connect. The network to which the wall-mounted control 120 is to connect is generally a network that communicatively couples the various components of the lift communications system 10 described herein. In some embodiments, the network may be network 11 depicted in FIGS. 10A-10B. In other embodiments, the network may be a direct connection with other devices, such as the direct connections depicted in FIG. 10C.

Still referring to FIGS. 1A-1B and 11, at block 1108, the user 1102 requests a network connection test. That is, the user 1102 may select a menu option in a user interface presented on a device, such as the wall-mounted control 120 and/or the remote control 130, that corresponds to a command to test the network connection between one or more components of the lift communications system with a network. Upon receiving such a request, the wall-mounted control 120 may connect with a dynamic host configuration protocol (DHCP) server 1112 at block 1110. The DHCP server 1112 returns DHCP information at block 1114. The DHCP information is generally a data transmission that contains information corresponding to various details of the network connection, which can be used to verify the network connection between the wall-mounted control 120 and a network.

Once connected to the network, the wall-mounted control 120 may connect to the server computing device 150 at block 1116, and if a connection is established, an acknowledgment may be transmitted by the server computing device 150 to the wall-mounted control 120 at block 1118. As a result of receiving the acknowledgement, the wall-mounted control may display a connection status at block 1120 to the user 1102. For example, a confirmation may be displayed at the wall-mounted control 120 and/or the remote control 130 that confirms the connection of the wall-mounted control to the network or the server computing device 150.

FIG. 12 relates to a process for establishing a location of the various components of the lift communications system 10 (FIGS. 1A-1B). In some embodiments, establishing a location of components may be based on CWS location configurations using an enterprise configuration tool (ECT). The process described herein with respect to FIG. 12 generally relates to an establishment of a fixed location of the wall-mounted control 120 since the wall-mounted control 120 may generally be assigned to a particular location upon installation. However, the present disclosure is not limited to such. That is, other components may also be established in a fixed location using the processes described in FIG. 12 without departing from the scope of the present disclosure.

Referring to FIGS. 1A-1B and 12, an installer 1202 may install devices at block 1206. The installer 1202 is generally a user that has access to software and/or tools for adding components to the network (e.g., network 11 depicted in FIGS. 10A-10B and/or the direct connections depicted in FIG. 10C). The components that may be added include any of the components described herein with respect to FIGS. 1A-1B, as well as other components not specifically described herein. For example, the installer 1202 may configure one or more of the rail-mounted lift 100, the mobile lift 100', the wall-mounted control 120, the remote control 130, the remote display 140, and/or the server computing device 150. In some embodiments, configuring one or more of the above-mentioned components may be completed by connecting a configuration device to each component, which transmits data and/or signals that cause configuration software to be executed. In other embodiments, configuring one or more of the above-mentioned components may be completed by interacting with a user interface of the component to cause pre-installed configuration software to be executed. In either of the embodiments, configuring the components generally includes providing information pertaining to a network to which the component is to be connected (or a direct connection to other components in some embodiments) and then directing the component to connect to the network using network interface hardware for that component, as discussed herein. In some embodiments, one or more logic modules included in the component (e.g., the logic modules discussed herein) may be used to facilitate configuration and connection to the network and/or directly connecting to other components.

Still referring to FIGS. 1A-1B and 12, at block 1208, the installer 1202 may provide a location of one or more devices that have been installed. For example, if the device is the wall-mounted control 120, the installer 1202 may associate an identifier of the space 103 with the wall-mounted control 120 such that other devices will recognize the wall-mounted control 120 being in the space 103. In some embodiments, the installer 1202 may further associate an identifier of the space 103 with the second component 113*b*, 113*b*' such that, when movable devices (e.g., the rail-mounted lift 100, the mobile lift 100', the remote control 130, or the like) are moved in or out of the space 103, the location of the device is updated automatically, as described herein. In some embodiments, for devices that may be movable in and out of the space, such as the rail-mounted lift 100, the mobile lift 100', the remote control 130, or the like, the installer 1202 may not provide a location. Rather, the location of the device is tracked and continually updated to indicate the location of the device as it moves throughout a facility. In other embodiments where a location of a movable device is not automatically updated, a user may provide the device location according to block 1208 to ensure a pairing of devices for use.

At block 1210, the various devices that are associated with the space are configured to communicate with one another, such as by using an ECT. That is, an ECT user 1204, which may be the same individual as the installer 1202 in some embodiments, may configure each of the devices for connecting to the network or via a direct connection. For example, the ECT user 1204 may complete one or more steps described herein with respect to FIG. 11 for each device to be configured. The ECT user 1204 may generally configure the devices by registering the devices with the server computing device 150 in some embodiments such that the server contains data that associates devices together by location and/or network. Accordingly, when the wall-mounted control 120 communicatively connects to the server computing device 150 at block 1212, the server computing device 150 transmits the location of the device(s) that are co-located with the wall-mounted control 120 at block 1214 such that the devices recognize one another on the network or such that a direct connection in both directions can be established.

In some embodiments, the various devices may be connected or disconnected from one another as needed, such as when a device that is capable of being moved between spaces (e.g., the rail-mounted lift 100, the mobile lift 100', the remote control 130, or the like). To preserve energy for the various devices (particularly in embodiments where devices are battery operated and must be periodically charged), certain devices may be put in a sleep state or a wake state. In the sleep state, the device is not used and may be disconnected from the other devices and/or the network. In the wake state, the device is used and may be connected to the other devices and/or the network for use as described herein. FIG. 13 depicts a flow diagram of an illustrative method that may be used to connect or disconnect various devices according to embodiments.

In some embodiments, pairing various devices (e.g., the wall-mounted control 120 with the rail-mounted lift 100 or the mobile lift 100') may include establishing a wireless connection between devices (e.g., a Bluetooth connection). Such a pairing may include a process whereby the installer 1202 or other user presses a button (e.g., either a hardware button or a software button on a user interface) to initiate a pairing process. Upon receiving a signal that the button has been pressed, each device may carry out a series of steps to pair with other devices. For example, certain devices (e.g., peripheral devices such as the rail-mounted lift 100 and/or the mobile lift 100') may generate and transmit a custom advertising packet that includes a custom signature identifying the device. Other devices, particularly central devices such as the wall-mounted control 120, may enter a scanning mode whereby the device receives the custom advertising packet, generates a particularly configured signal for the device, and initiates a connection according to the information contained within the custom advertising packet. In some embodiments, such pairing may be retained in memory to ensure the devices are paired to one another in the future if the devices become disconnected (e.g., if the rail-mounted lift 100 and/or the mobile lift 100' move out of range from the device to which they are connected).

Figure 16B:
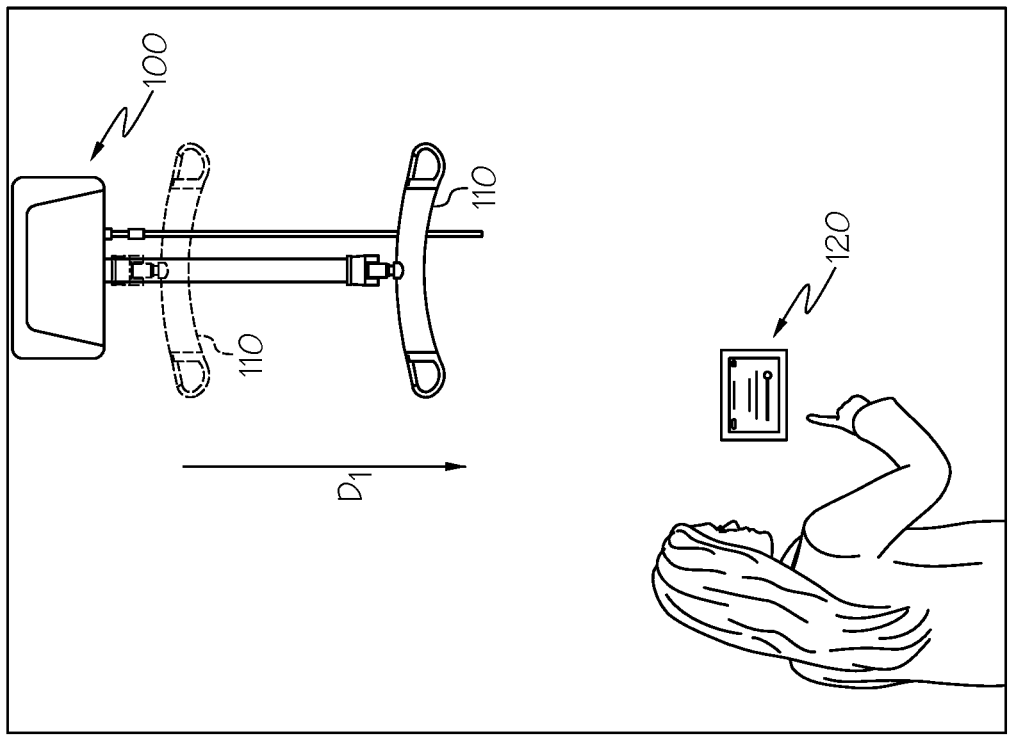
FIG. 16B depicts movement of a rail-mounted lift as the result of user interaction with the activation user interface of FIG. 16A according to one or more embodiments shown and described herein.
Figure 16A:
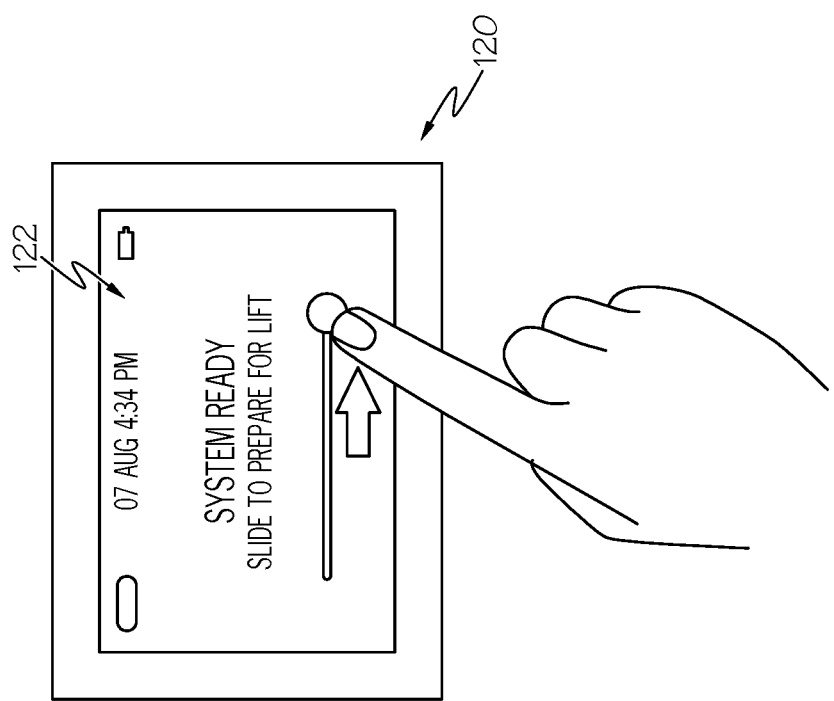
FIG. 16A schematically depicts a user interaction with an activation user interface of a wall-mounted control according to one or more embodiments shown and described herein.

Referring to FIGS. 1A-1B and 13, a user 1302 may wake a device at block 1304. In the embodiment depicted in FIG. 13, the device that is woken is the lift (e.g., the rail-mounted lift 100 or the mobile lift 100'). However, it should be understood that the user may wake other devices in other embodiments (e.g, the wall-mounted control 120 and/or the remote control 130). The user 1302 is generally an individual operating the various components, including the rail-mounted lift 100, the mobile lift 100', the wall-mounted control 120, and/or the remote control 130. The user 1302 may wake the device by actuating a user interface control in some embodiments, such as, for example, pressing a "SLEEP/WAKE" button, pressing a power button, by touching a touchscreen to cause the device to come out of a wake state, and/or the like. In some embodiments, the user 1302 may wake the wall-mounted control 120 by interacting with the user interface provided on the display 122. For example, as depicted in FIG. 16A, the display 122 may display a user interface including the text "SYSTEM READY" and "SLIDE TO PREPARE FOR LIFT," as well as a slider user interface toggle. When the user moves the slider on the user interface, the wall-mounted control 120 may be placed in the wake state.

Referring again to FIGS. 1A-1B and 13, once the lift has been placed in a wake state, the lift may initiate a connection with the wall-mounted control 120 at block 1306. That is, referring also to FIGS. 6 and 7, the communications logic 624 of the lift may transmit one or more signals via the network interface hardware 640, which is received by the network interface hardware 740 of the wall-mounted control 120 and processed by the communications logic 724 to establish a connection with the lift. If the wall-mounted control 120 is not in a wake state (e.g., in a sleep state), the connection attempt at block 1306 may function as a signal to wake the wall-mounted control 120, which then transmits a wall screen state connection signal at block 1308 to the server computing device 150. The server computing device 150 may determine that the wall-mounted control 120 is awake and ready to be paired with the lift, and may transmit an acknowledgement signal at block 1310. In addition, the wall-mounted control 120 may transmit a lift state connection signal at block 1312 to the server computing device 150. Such a signal may generally indicate that a connection between the lift and the wall-mounted control 120 is being attempted. The server computing device 150 may record the connection and transmit an acknowledgement at block 1314. In some embodiments, once the lift and the wall-mounted control 120 are connected with one another, the lift may provide an indicator of such a connection. For example, as depicted in FIG. 16B, the rail-mounted lift 100 may indicate a connection with the wall-mounted control 120 by moving the sling bar 110 from a stowed position to an extended position, as indicated by arrow $D_1$. In another example, the rail-mounted lift 100 and/or the mobile lift 100' (FIG. 1B) may have one or more indicators thereon that indicate connection status (e.g., an indicator LED that is externally located and lights up or changes color based on connection status).

Referring again to FIGS. 1A-1B and 13, in embodiments where it may be desired to disconnect the lift from the wall-mounted control 120 (e.g., when the lift is no longer in use, when the lift is to be removed from the space associated with the wall-mounted control 120, when the lift is undergoing repair or replacement, and/or the like), a disconnect signal may be transmitted by the lift to the wall-mounted control 120 at block 1316. As a result of receiving the disconnect signal, the wall-mounted control 120 may transmit an update in lift state to the server computing device 150 at block 1318 and may receive an acknowledgment from the server computing device 150 at block 1320. It should be understood that this disconnection also may occur when the lift is to be connected to a different wall-mounted control 120 (e.g., when the lift is moved to a different space where a different wall-mounted display is connected to the lift). Such a disconnection may be forced by the connection of the lift with the other wall-mounted display. In some embodiments, the spaces may be lined with a material that does not allow radio signals to pass through, thereby causing the lift to disconnect from the wall-mounted control 120 upon leaving the space. In some embodiments, a user may manually select (e.g., via a user interface on the lift or the wall-mounted control 120) an option to disconnect the lift from the wall-mounted control 120.

If the lift is not being used (e.g., is disconnected from a wall-mounted control 120, has been idle for a predefined period of time, and/or the like), the lift may return to a sleep state at block 1322. It should be understood that while FIG. 13 generally relates to connection of a lift (e.g., the rail-mounted lift 100 and/or the mobile lift 100') to the wall-mounted control 120, this is merely illustrative. In some embodiments, the lift may be connected to another component, such as, for example, the remote control 130, using the processes described with respect to FIG. 13. In some embodiments, the wall-mounted control 120 may be connected to another component, such as, for example, the remote control 130, using the processes described with respect to FIG. 13.

FIG. 14 depicts a flow diagram of an illustrative user association process according to various embodiments. Referring to FIGS. 1A-1B and 14, the wall-mounted control 120 may transmit a request for an identification of one or more subjects in a particular location (e.g., the space 103) to the server computing device 150 at block 1404, which may then transmit a list of identifiers corresponding to subjects at block 1406. Such a request and subsequent transmission may be automatically completed at predetermined time intervals by the wall-mounted control 120 to ensure the most up-to-date information is obtained, or may be completed when a user input corresponding to a subject association request is received (e.g., at the wall-mounted control 120, at the remote control 130, and/or the like). In some embodiments, the identification of the one or more subjects may be all subjects associated with the space 103, regardless of whether a lift is used with such subjects. In some embodiments, block 1404 may be omitted. Rather, the server computing device 150 may automatically push a list of subjects to the wall-mounted control 120 according to block 1406 at a predetermined intervals and/or when the list is updated at the server computing device 150 without receiving a request. In some embodiments, the data that is transmitted from the server computing device 150 to the wall-mounted control 120 may be encrypted or otherwise encoded such that the information pertaining to subjects is only readable by the wall-mounted control 120.

Figure 24:
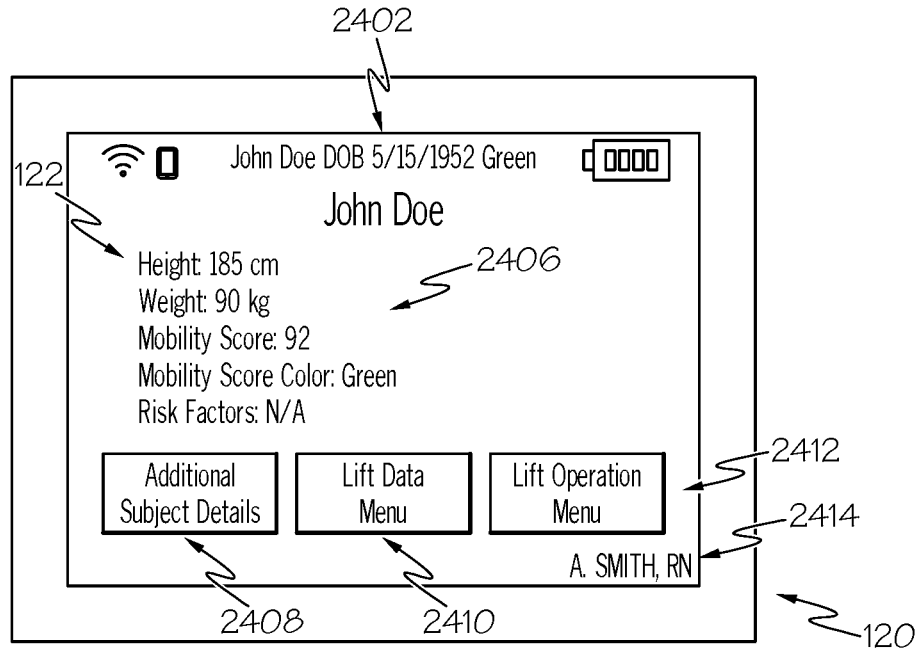
FIG. 24 schematically depicts a screen shot of a user interface on a wall-mounted control configured to display information pertaining to an associated subject, including a subject mobility score, according to one or more embodiments shown and described herein.

At block 1408, the wall-mounted control 120 may store the list of subjects in local storage (e.g., within the other data 758 of the data storage device 750 depicted in FIG. 7). Still referring to FIGS. 1A-1B and 14, if there is only one subject that is received at block 1406 and stored at block 1408, the wall-mounted control 120 may only display the single subject's name and associated information at block 1410. For example, as depicted in FIG. 24, the user interface displayed by the display 122 of the wall-mounted control 120 may include header information 2402 such as name, date of birth (DOB), and/or a quick reference mobility score indicator. The quick reference mobility score indicator is generally an indicator that allows a person viewing the display 122 to quickly discern what the subject's mobility score is. For example, in the embodiment shown in FIG. 24, the subject has a "Green" mobility score, which corresponds to a subject that is generally mobile (e.g., having a mobility score of 92). Other information 2406 that may be provided via the display 122 pertaining to the subject includes, but is not limited to, a subject height, a subject weight, the mobility score, and/or one or more risk factors. The display 122 may also provide an "Additional Subject Details" option button that allows for further information to be displayed about the subject, such as medical records or the like.

Figure 23:
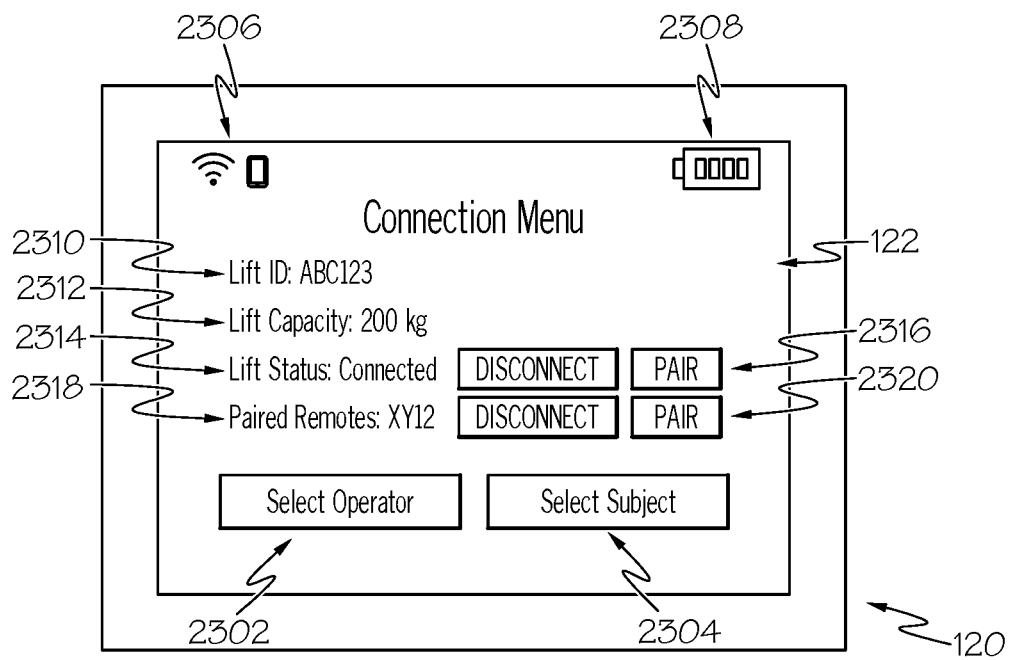
FIG. 23 schematically depicts a screen shot of a user interface on a wall-mounted control configured to display information pertaining to a connected lift and paired remote, as well as options for selecting an operator and/or a subject to associate with the lift according to one or more embodiments shown and described herein.

Referring again to FIGS. 1A-1B and 14, if a plurality of subjects is received at block 1406 and stored at block 1408, the wall-mounted control 120 may display a list of available subjects to a user 1402 (e.g., a caregiver) at block 1412. For example, as depicted in FIG. 23, a user may select a "select subject" button 2304 in the user interface displayed by the display 122 to show the list of subjects according to block 1410. The user may then select a subject at block 1414 by interacting with the user interface (e.g., pressing a button on the user interface corresponding to the subject to be selected). At block 1416, the wall-mounted control 120 may store the selected subject in local storage (e.g., within the other data 758 of the data storage device 750 depicted in FIG. 7).

At block 1418, the wall-mounted control 120 may display information pertaining to the subject. For example, as depicted in FIG. 24, the user interface displayed by the display 122 of the wall-mounted control 120 may include header information 2402 such as name, date of birth (DOB), and/or a quick reference mobility score indicator. The quick reference mobility score indicator is generally an indicator that allows a person viewing the display 122 to quickly discern what the subject's mobility score is. For example, in the embodiment shown in FIG. 24, the subject has a "Green" mobility score, which corresponds to a subject that is generally mobile (e.g., having a mobility score of 92). Other information 2406 that may be provided via the display 122 pertaining to the subject includes, but is not limited to, a subject height, a subject weight, the mobility score, and/or one or more risk factors. The display 122 may also provide an "Additional Subject Details" option button that allows for further information to be displayed about the subject, such as medical records or the like.

Figure 18B:
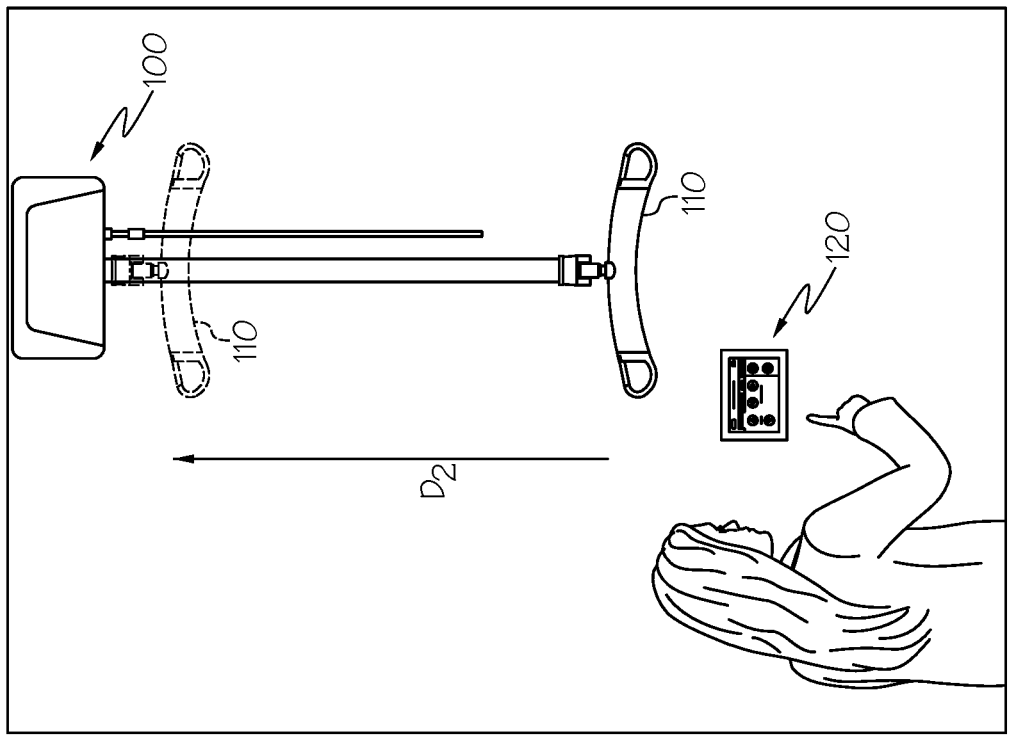
FIG. 18B schematically depicts movement of components of a rail-mounted lift as a result the interaction with the user interface of FIG. 18A according to one or more embodiments shown and described herein.
Figure 18A:
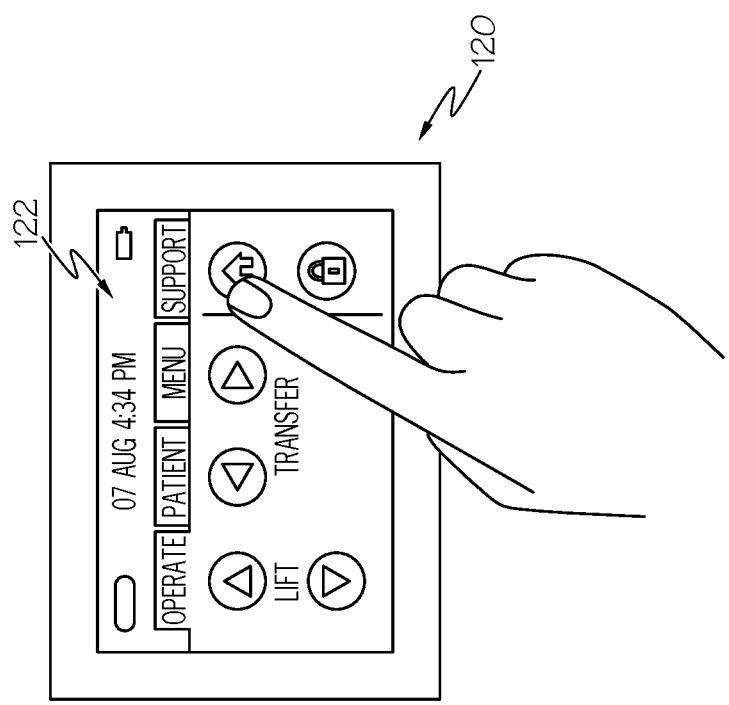
FIG. 18A schematically depicts a user interaction with a user interface of a wall-mounted control according to one or more embodiments shown and described herein.

Referring again to FIGS. 1A-1B and 14, the user 1402 may perform one or more lifting option by interacting with the user interface at block 1420. For example, as shown in FIGS. 18A-18B, the user may select a button displayed by the display 122 of the wall-mounted control 120 to cause movement of the rail-mounted lift unit 100 (or the mobile lift unit (not shown)). In the embodiment depicted in FIGS. 18A-18B, the user has selected the "home" button, which returns the rail-mounted lift unit 100 to a standard, not-in-use positioning that is suitable for movement along the rail 102 (FIG. 1A). That is, the sling bar 110 is raised from an extended position to a stowed position, as indicated by directional arrow $D_2$ in FIG. 18B. The user may also press various buttons displayed by the display 122 (e.g., directional buttons) to move the rail-mounted lift unit (e.g., move the rail-mounted lift unit 100 along the rail 102 (FIG. 1A)), further extend or retract the sling bar 110, and/or the like. Once lifting operation is complete, data pertaining to the lift operation (e.g., lift movement, subject information, any error messages, sensed lift parameters, and/or the like) may be transmitted by the wall-mounted control 120 to the server computing device 150 at block 1422. The data may later be used for the purposes of updating the subject's electronic medical records, for displaying information in the aggregate on the remote display 140 (FIG. 1A), and/or the like. In some embodiments, if a subject is not selected according to block 1414, the various movements of the lift may not be recorded.

In some instances, it may be necessary to update software that is utilized for one or more components of the lift communications system 10 to ensure appropriate operation. Such an update process may be completed by a user with access to an update server that is communicatively coupled to the various components of the lift communications system 10, or by directly accessing one or more components of the lift communications system 10 and requesting an update process. FIG. 15 depicts a flow diagram of an illustrative method of updating the software of the lift 100, 100' via the wall-mounted control 120 according to various embodiments. However, it should be understood that the process described with respect to FIG. 15 can be completed for updating firmware for any of the components of the lift communications system 10 without departing from the scope of the present disclosure.

Referring to FIGS. 1A-1B and 15, a user 1502 (e.g., a service technician) may initiate a firmware download at block 1506 by submitting a request via a user interface to an update server 1504. The update server 1504 is generally a server containing software updates that is periodically updated by a software developer. Upon initiation of the firmware download, the update server 1504 may initiate a connection with the wall-mounted control 120 and may transmit data (e.g., an install package, binary images, and/or the like) to the wall-mounted control 120 via an SSH File Transfer Protocol (SFTP) at block 1508. Alternatively, the user 1502 may directly transmit data (e.g., an install package, binary images, and/or the like) to the wall-mounted control 120 without using the update server 1504. For example, the user 1506 may couple a storage device (e.g., a USB storage drive, a service device, or the like) to the wall-mounted control 120 and transfer the necessary update files.

Once the data has been fully transmitted to the wall-mounted control 120, the update server 1504 may transmit an indicator that indicates the download is complete at block 1510 and transmit a report of the download stats to the user 1502 at block 1512. For example, the user 1502 may receive an indication at a user interface stating "UPDATE FILE TRANSFER COMPLETE" or similar text.

At block 1514, the wall-mounted control 120 may verify the file integrity of the downloaded data to ensure the data has not been compromised, is not corrupted, is complete, and/or the like. If the downloaded data is verified, the wall-mounted control may transmit data (e.g., download the lift firmware) to the lift 100, 100' at block 1516. In some embodiments, the wall mounted control 120 may extract files from the data that is transferred (e.g., extract a Red Hat Package Manager (RPM) from an install package), install necessary files on the wall-mounted control 120, and transfer the remaining binary files to the lift (e.g., the rail-mounted lift 100 or the mobile lift 100'), such as in an inactive, non-volatile memory bank located on the lift (e.g., within the memory 620 and/or the data storage 650 (FIG. 6)).

Alternatively, the user 1502 may directly transmit data (e.g., an install package, binary images, and/or the like) to the lift (e.g., the rail-mounted lift 100 or the mobile lift 100') without using the update server 1504 or the wall-mounted control 120. For example, the user 1506 may couple a storage device (e.g., a USB storage drive, a service device, or the like) to the lift (e.g., the rail-mounted lift 100 or the mobile lift 100') and transfer the necessary update files.

The data (e.g., firmware) may then be downloaded (e.g., flashed) to the lift 100, 100' at block 1516 and once the process is complete, the wall-mounted control 120 may transmit an indicator indicating the staging (e.g., updating) is complete to the update server 1504 at block 1518. The update server 1504 may then provide a report of the download and installation status to the user 1502 at block 1520.

In some embodiments, installing the software update may include use of dual memory banks to ensure that the software update is only completed at a time when the lift is not in use so as to avoid an issue where the lift shuts down for an update in the middle of use. Referring also to FIG. 6, in such embodiments, data is downloaded to an inactive, non-volatile memory bank that is separate from the memory bank that is typically utilized to store operating software (e.g., the operating logic 622 of the memory 620). The separate memory bank is still accessible by the processing device 610 (e.g., an STM32 microprocessor). The data (e.g., binary files) remain in the separate memory bank indefinitely until a command is received to upgrade the system. Once such a command is received (e.g., via the user 1502, the update server 1504, the wall-mounted control 120, or a service tablet), the processing device 610 reads the upgrade package from the non-active bank, transfers the data (e.g., binary images) to each destination (e.g., each of a plurality of microprocessors) via various channels of the local interface 600, and directs each destination to upgrade and reset. The processing device 610 may also upgrade and reset. In some embodiments, destinations the furthest away from the processing device 610 may be upgraded first (e.g., the hand control unit 112 (FIG. 1A)), then the next furthest destinations, and so on, with the processing device 610 being upgraded last. Such a process may ensure that a software upgrade on a destination does not prevent reaching another destination further down the chain due to incompatibility. Once the upgrade and reset process is completed, various components may be re-bonded (e.g., communicatively coupled) such that the lift resumes operation with the new upgrade. In some embodiments, the data that was transferred (both to the lift and the wall-mounted display 120) will remain in storage until overwritten by another image (e.g., a newer update).

In some embodiments, prior to resuming operation of the lift, the various upgraded components may be verified for proper installation and use. For example, a cyclic redundancy check (CRC) may be performed and a result status may be transmitted to the processing device 610 to indicate success or failure. If a success, the destinations may be placed into a bootloader mode to reset the destinations for use.

FIGS. 16A-16B, 17A-17B, 18A-18B, 19A-19B, 20A-20B, and 21-26 depict particular user interfaces of particular uses for which the wall-mounted control 120 can be used. While FIGS. 16A-16B, 17A-17B, 18A-18B, 19A-19B, 20A-20B, and 21-26 relate specifically to user interfaces presented on the wall-mounted control 120, this is merely illustrative. In some embodiments, similar user interfaces may be displayed on the remote control 130 (FIGS. 1A-1B) without departing from the scope of the present disclosure.

As depicted in FIGS. 16A-16B, a user can slide a slider to activate the wall-mounted control 120 and/or the rail-mounted lift 100, as previously described in greater detail herein. When the user slides the slider, the rail-mounted lift unit 100 may activate and move the sling bar 110 to an extended position, as shown in FIG. 16B.

Figure 17B:
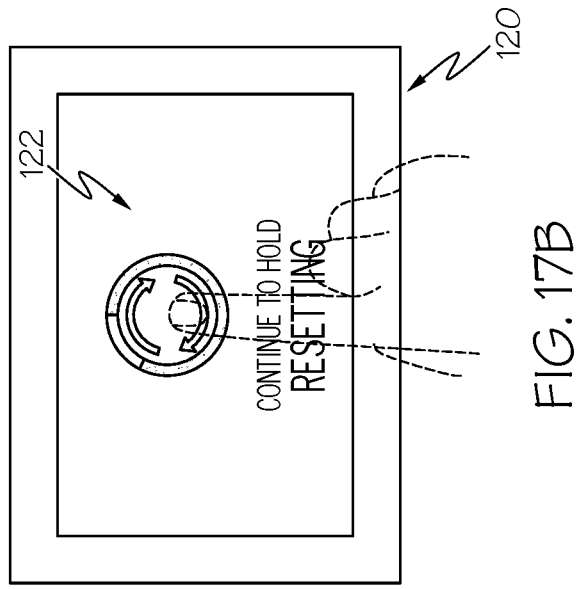
FIG. 17B schematically depicts a screen shot of an interface in a wall-mounted control in a reset mode according to one or more embodiments shown and described herein.
Figure 17A:
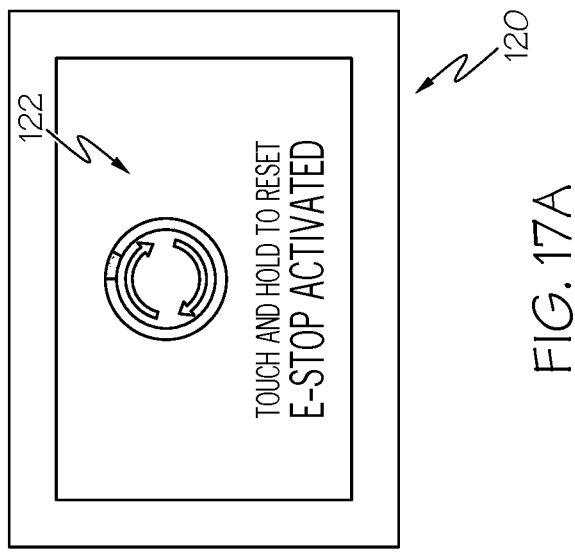
FIG. 17A schematically depicts a screen shot of an interface in a wall-mounted control in an emergency stop according to one or more embodiments shown and described herein.

In some embodiments, the various components of the lift communications system 10 may be placed in an emergency stop mode to prevent further operation thereof. For example, a user may select an emergency stop option in a user interface, which results in the display 122 of the wall-mounted control 120 displaying an emergency stop user interface as depicted in FIG. 17A. The emergency stop user interface may provide instructions such as "TOUCH AND HOLD TO RESET" that direct the user to reset one or more components for further use. As such, as depicted in FIG. 17B, a user touching and holding the display 122 of the wall-mounted control 120 may cause one or more devices (e.g., the lift) to reset for further use.

As previously described herein, FIGS. 18A-18B depict a user actuating a "home" button within the user interface displayed on the display 122 of the wall-mounted control 120. Actuation of such a button may cause the rail-mounted lift unit 100 to retract the belt, thereby moving the sling bar 110 (or other accessory) from an extended position to a retracted position as indicated by directional arrow $D_2$.

Figure 19A:
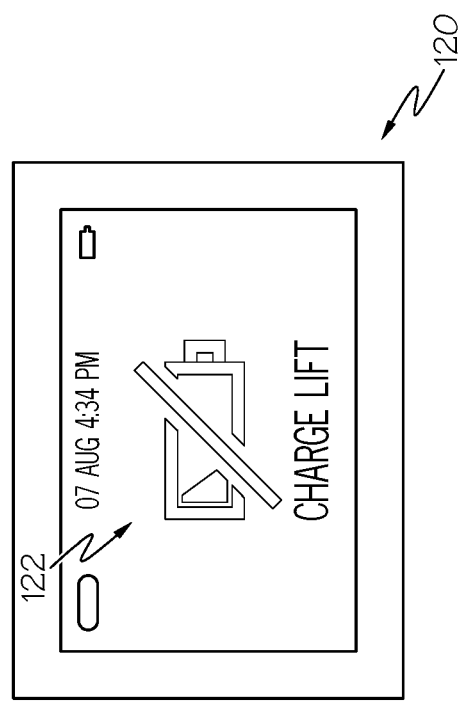
FIG. 19A schematically depicts a screen shot of an interface in a wall-mounted control providing a notification according to one or more embodiments shown and described herein.
Figure 19B:
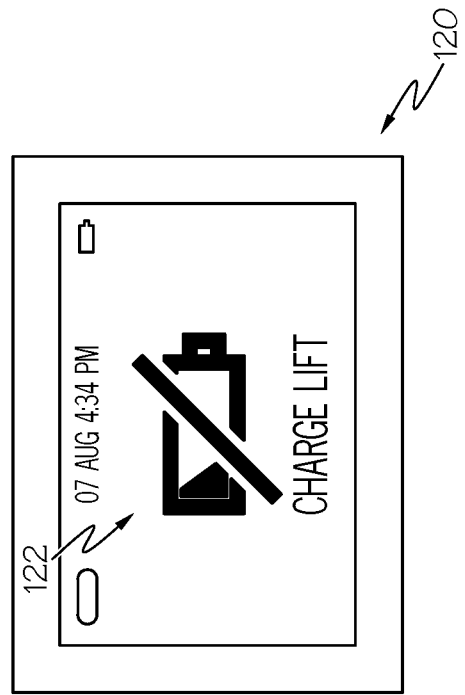
FIG. 19B schematically depicts a screen shot of an interface in a wall-mounted control providing a notification according to one or more embodiments shown and described herein.

In some embodiments, if a battery in a lift associated with the wall-mounted control 120 is low on charge, the wall-mounted control 120 may display a "charge lift" icon on the display 122 as depicted in FIGS. 19A-19B. More specifically, the "charge lift" icon may flash from a light color as depicted in FIG. 19A to a dark color as depicted in FIG. 19B to draw a user's attention that the lift is in need of a charge.

Figure 20B:
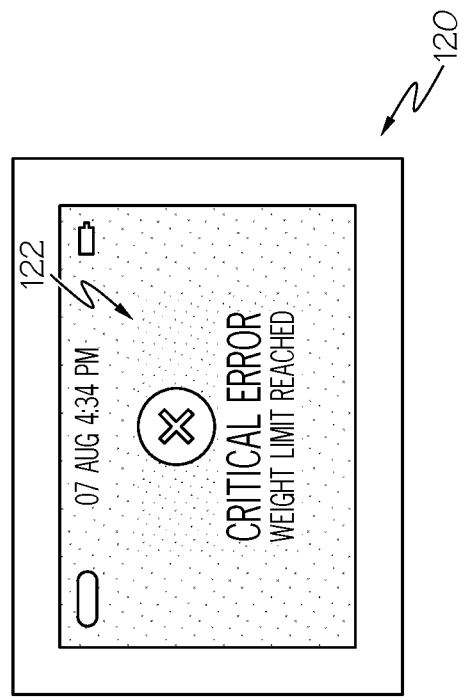
FIG. 20B schematically depicts a screen shot of an interface in a wall-mounted control providing an error notification according to one or more embodiments shown and described herein.
Figure 20A:
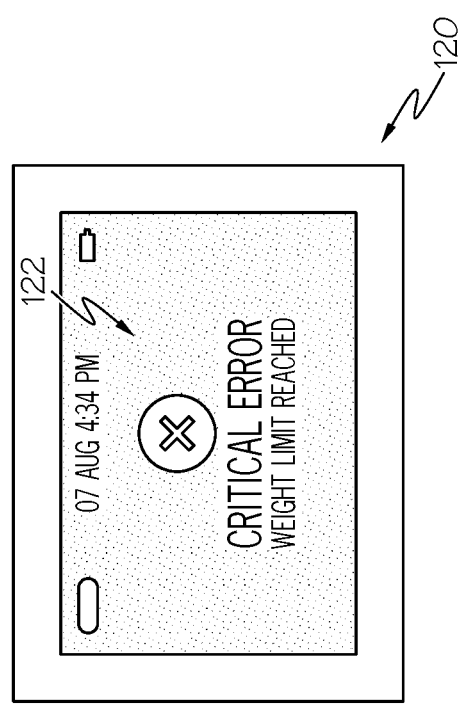
FIG. 20A schematically depicts a screen shot of an interface in a wall-mounted control providing an error notification according to one or more embodiments shown and described herein.

As described herein, the various lifts (e.g., the rail-mounted lift 100 depicted in FIG. 1A and/or the mobile lift 100' depicted in FIG. 1B) may include one or more sensors that are capable of sensing characteristics of a subject being lifted. For example, the various lifts may include one or more load sensors that can sense a load supported by the lift. That is, the load sensors can determine the weight of a subject placed in a sling or otherwise coupled to the sling bar of the lift. As the lift is generally rated for a particular load, any excess of the load can cause damage or incorrect operation of the lift. Accordingly, the load sensor, when sensing a load that exceeds the maximum allowable load for a particular lift, may transmit data and/or signals to the wall-mounted control 120 such that the wall-mounted control 120 displays a "CRITICAL ERROR WEIGHT LIMIT REACHED" message on the display 122 thereof, as depicted in FIGS. 20A-20B. More specifically, the background surrounding the "CRITICAL ERROR WEIGHT LIMIT REACHED" message may flash from a light color as depicted in FIG. 20A to a dark color as depicted in FIG. 20B to draw a user's attention that the load exceeds the maximum allowable amount for the lift.

In some embodiments, it may be desirable to display information to the user that allows a user to learn how to properly operate a lift. For example, if a user desires to learn how to attach accessories or the like to a lift unit (e.g., the rail-mounted lift 100 depicted in FIG. 1A and/or the mobile lift 100' depicted in FIG. 1B), the display 122 on the wall-mounted control 120 may display step-by-step instructions for attaching accessories, as depicted in FIG. 21. More specifically, the embodiment depicted in FIG. 21 indicates three steps. After an elapsed period of time (10 seconds in the embodiment depicted in FIG. 21), the next step may be automatically displayed such that a user can follow along. Alternatively, the user can select the side arrows that are displayed by the display 122 to move to the next display for additional instructions on how to properly operate the lift.

Figure 22:
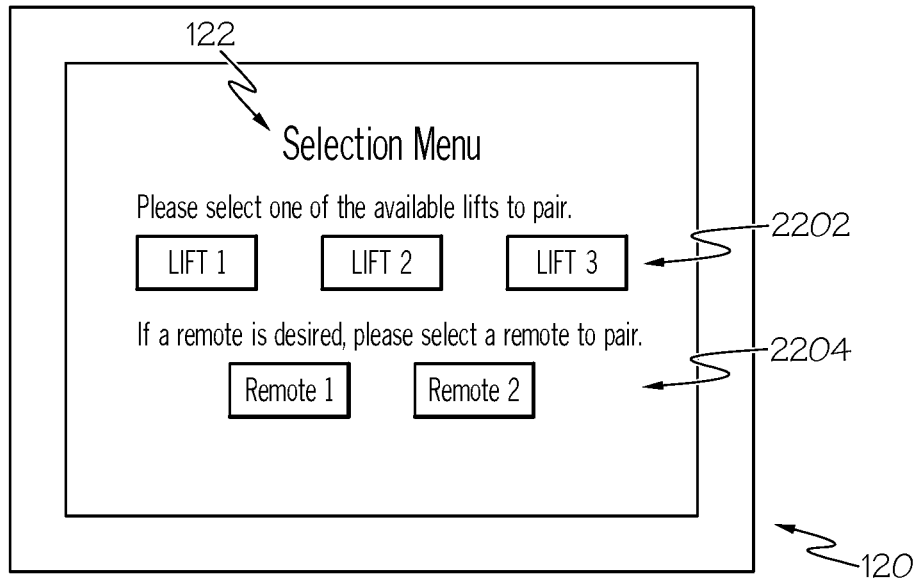
FIG. 22 schematically depicts a screen shot of a user interface on a wall-mounted control configured to select a lift and a remote to pair according to one or more embodiments shown and described herein.

As previously described herein, a wall-mounted control 120 may be communicatively coupled to a plurality of lifts (e.g., the rail-mounted lift 100 depicted in FIG. 1A and/or the mobile lift 100' depicted in FIG. 1B) and/or a plurality of remote controls (e.g., remote control 130 depicted in FIGS. 1A-1B) at the same time. For example, if the wall-mounted control 120 is located in a common area (e.g., a therapy gym or the like) that contains a plurality of lifts and/or a plurality of remote controls, the wall-mounted control 120 may be connected to all devices at the same time. In such embodiments, it may be necessary for a user to select a particular device that the user desires to operate via the wall-mounted control. For example, as shown in FIG. 22, the display 122 of the wall-mounted control 120 may display a selection menu whereby one or more lift selections 2202 and one or more remote selections 2204 are selectable by a user. Upon selection of one of the one or more lift selections 2202 and/or one of the one or more remote selections 2204, the wall-mounted control 120 may connect to the associated lift and/or remote accordingly.

In some embodiments, the wall-mounted display may provide an ability for a user to view details regarding a coupled component, provide inputs for pairing or disconnecting components, providing inputs for selecting an operator, and/or provide inputs for selecting a subject. For example, as depicted in FIG. 23, the display 122 of the wall-mounted control 120 may provide a connection menu interface that displays information about one or more connected devices and/or provides selectable options to a user. For example, a "select operator" button 2302 may allow a user to select one or more operators of the lift. Selection of an operator may be necessary to ensure that only authorized users are able to operate the lift and/or to ensure data corresponding to who operated a lift and when is recorded. In another example, a "select subject" button 2304 may allow a user to select a subject to be supported by the lift, as described herein. Additional information regarding connected components, such as a connection status icon 2306 (indicating which devices are connected and/or a strength of connection) and/or a battery level status icon 2308 (indicating a battery level of a connected component) may also be displayed by the display 122. Details regarding a connected lift, including, but not limited to a lift identification indicator 2310, a lift capacity indicator 2312, a lift connection status indicator 2314 and/or a paired remote status indicator 2318 may also be displayed, as well as lift disconnect/pair selectors 2316 and remote disconnect/pair selectors 2320.

As previously described herein, FIG. 24 depicts the display 122 of the wall-mounted control 120 depicting header information 2402 and/or other information 2406 pertaining to a subject who is being supported by the lift. The user may also select an "Additional Subject Details" button 2408 to view additional details regarding the subject, may select a "Lift Data Menu" button 2410 that navigates to the lift data menu depicted in FIG. 24, and/or a "Lift Operation Menu" button 2412 that navigates to the lift operation menu depicted in FIGS. 18A-18B for example. Also depicted in FIG. 24 is a user indicator 2414, which identifies the user of the wall-mounted control 120.

Figure 25:
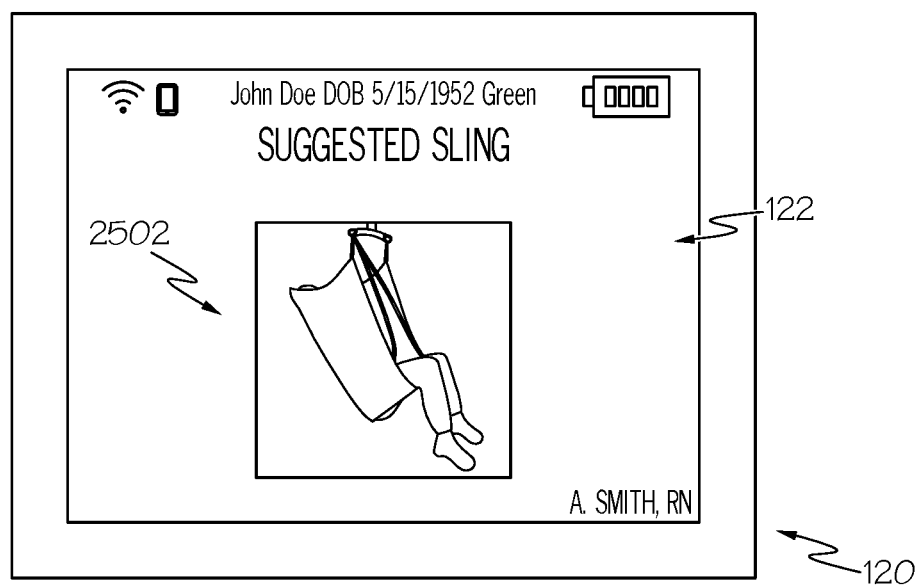
FIG. 25 schematically depicts a screen shot of a user interface on a wall-mounted control configured to display information pertaining to a suggested sling for a particular subject based on data obtained pertaining to the lift and the subject according to one or more embodiments shown and described herein.

In some embodiments, a user may not be aware of or unsure of the type of equipment to be used to hoist a subject. In such embodiments, the wall-mounted control 120 may provide suggestions to the user that allow the user to make a decision based on inputs, stored data, and/or sensed data, as depicted in FIG. 25. For example, if a user supplies his/her identity, selects a subject, and selects a particular lift, the display 122 of the wall-mounted control 120 may provide a suggested components interface 2502 that suggests components such as particular slings or the like. Such slings may be suggested based on the type of equipment being used, various characteristics of the subject, and/or stored information pertaining to what type of equipment a user is authorized to use, trained to use, and/or the like.

Referring again to FIGS. 1A-1B, the various components of the lift communications system 10 may be used to collect and/or process data pertaining to the components of the lift communications system 10, a subject, a user, and/or the like. Illustrative examples of data points include, but are not limited to, a number of lifts undergone in a lifetime of a particular rail-mounted lift 100 and/or mobile lift 100', a number of lifts undergone in a past period (e.g., past seven days) of a particular rail-mounted lift 100 and/or mobile lift 100', a number of error messages generated in a lifetime for a particular component, a service interval for a particular component, an annual service interval for a particular component, a last service date for a particular component, a next service date for a particular component, an amount of power consumed during a lifting activity, an amount of power consumed during a lifting activity since last service, a number of times a component (e.g., the rail-mounted lift 100 and/or the mobile lift 100') has reported being overloaded in a lifetime, a number of times a component (e.g., the rail-mounted lift 100 and/or the mobile lift 100') has reported being overloaded since a previous service, a number of times a component (e.g., the rail-mounted lift 100 and/or the mobile lift 100') has reported being excessively used in a lifetime, a number of times a component (e.g., the rail-mounted lift 100 and/or the mobile lift 100') has reported being excessively used since a previous service, a number of times a component of the rail-mounted lift 100 and/or the mobile lift 100' has reported having reached an upper lift limit (e.g., lifting strap 108 drawn up to highest height) in a lifetime, a number of times a component of the rail-mounted lift 100 and/or the mobile lift 100' has reported having reached an upper lift limit (e.g., lifting strap 108 drawn up to highest height) since a previous service, a number of times a component of the rail-mounted lift 100 and/or the mobile lift 100' has reported having reached a lower lift limit (e.g., lifting strap 108 paid out to lowest height) in a lifetime, a number of times a component of the rail-mounted lift 100 and/or the mobile lift 100' has reported having reached a lower lift limit (e.g., lifting strap 108 paid out to lowest height) since a previous service, a serial number of a particular component (e.g., a motor of the lift unit 104, a mainboard of the lift unit 104, etc.), a software version of a particular component (e.g., a mainboard of the lift unit 104, etc.), a firmware version of a particular component, whether a firmware update is ready for a particular component, details regarding a wireless signal (including, but not limited to, signal strength), a count of the number of times a battery has been fully discharged, a current battery level, a historical battery level, a battery charging status, a low battery warning, conditions that caused an electrical overload, conditions that caused excessive usage, conditions that caused errors, when and where an emergency stop was activated, conditions that resulted in an emergency stop, a communication failure between various components, errors pertaining to location tracking, information pertaining to types of service requested or required, a location of components, a location history of components, a number of days until a service is due, a number of days overdue for service, information pertaining to a language selection, and/or the like. It should be understood that the data points provided herein are merely illustrative, and other data points are contemplated and included within the scope of the present disclosure.

In some embodiments, the various data points, regardless of whether described above, may be particularly useful on particular devices (e.g., the rail-mounted lift 100, the mobile lift 100', the hand control unit 112, the wall-mounted control 120, the remote control 130 (e.g., on a service tool thereof), the remote display 140, or the like), and/or by particular users (e.g., authorized service providers, caregivers, clinical staff, and/or the like). Table 1 below depicts illustrative data points and illustrative use on particular devices and/or by particular users. It should be understood that Table 1 is merely provided for illustrative purposes and is not meant to be limiting.

TABLE 1

| Data Point | Users available to | | Data/visual indication accessible on | | | |
|---|---|---|---|---|---|---|
| | Authorized Service (service, trained tech.) | Caregiver/ Clinical Staff | Lift Unit | Hand Control Unit | Wall-Mounted Control | Remote control |
| Number of lifts-lifetime | Yes | Yes | No | No | Yes | Yes |
| Number of lifts in past 7 days | Yes | Yes | No | No | Yes | Yes |
| Lift event activity-lifetime | Yes | Yes | No | No | Yes | Yes |
| Lift event activity-subject | Yes | Yes | No | No | Yes | Yes |
| Error messages-lifetime | Yes | No | No | No | Yes | Yes |
| Service Interval (Customer) | Yes | No | No | No | Yes | Yes |
| Service Interval-Annual service | Yes | No | No | No | Yes | Yes |
| Last service date | Yes | No | No | No | Yes | Yes |
| Next Service Date | Yes | Yes | No | No | Yes | Yes |
| Power consumed during lifts-lifetime | Yes | No | No | No | Yes | Yes |
| Power consumed during lifts-since last service | Yes | No | No | No | Yes | Yes |
| Number of lifts-lifetime | Yes | No | No | No | Yes | Yes |
| Number of lifts-since last service | Yes | No | No | No | Yes | Yes |
| Number of overloads-lifetime | Yes | No | No | No | Yes | Yes |
| Number of overloads-since last service | Yes | No | No | No | Yes | Yes |
| Number of excessive usage-lifetime | Yes | No | No | No | Yes | Yes |
| Number of excessive usage-since last service | Yes | No | No | No | Yes | Yes |
| Number of Upper lift limit reached-lifetime | Yes | No | No | No | Yes | Yes |

TABLE 1-continued

| | Users available to | | Data/visual indication accessible on | | | |
|---|---|---|---|---|---|---|
| Data Point | Authorized Service (service, trained tech.) | Caregiver/ Clinical Staff | Lift Unit | Hand Control Unit | Wall-Mounted Control | Remote control |
| Number of Upper lift limit reached-since last service | Yes | No | No | No | Yes | Yes |
| Number of Lower lift limit reached-lifetime | Yes | No | No | No | Yes | Yes |
| Number of Lower lift limit reached-since last service | Yes | No | No | No | Yes | Yes |
| Motor serial number | Yes | No | No | No | Yes | Yes |
| Mainboard hardware serial number | Yes | No | No | No | Yes | Yes |
| Mainboard software version | Yes | No | No | No | Yes | Yes |
| Firmware update ready | Yes | No | No | No | Yes | Yes |
| Wireless details (Include signal strength) | Yes | No | No | No | Yes | Yes |
| Battery deep discharge count | Yes | No | No | No | No | Yes |
| Battery level | Yes | Yes | Yes | Yes | Yes | Yes |
| Battery charging status | Yes | Yes | Yes | Yes | Yes | Yes |
| Lower Battery warning | Yes | Yes | Yes | Yes | Yes | Yes |
| Battery degradation level | Yes | No | No | No | No | Yes |
| Overload condition | Yes | Yes | No | No | Yes | Yes |
| Excessive Usage condition | Yes | Yes | No | No | Yes | Yes |
| Error condition (critical) | Yes | Yes | Yes | Yes | Yes | Yes |
| Emergency stop activated | Yes | Yes | No | No | Yes | Yes |
| Communication failure (Hoist to Wall-mounted control) | Yes | Yes | Yes | Yes | Yes | Yes |
| Wireless status | Yes | Yes | Yes | Yes | Yes | Yes |
| Location Error | Yes | Yes | No | No | Yes | Yes |
| Service required | Yes | Yes | Yes | Yes | Yes | Yes |
| Hoist Location | Yes | Yes | No | No | Yes | Yes |
| Days until/past service due | Yes | Yes | No | No | Yes | Yes |
| Language Selection | Yes | Yes | No | No | Yes | Yes |

As noted in Table 1 above, in some embodiments, the data obtained and provided via the various components described herein may be presented to particular users such as caregivers, clinical staff, and/or the like for the purposes of operating the various components. For example, information pertaining to a mobility score of a subject and information pertaining to the type of components included with the rail-mounted lift 100 and/or the mobile lift 100' may enable such users to determine a particular manner to operate the rail-mounted lift 100 and/or the mobile lift 100' for that particular subject and/or ensure that the rail-mounted lift 100 and/or the mobile lift 100' is adequately equipped for the particular subject and/or a particular use.

As also noted in Table 1 above, in some embodiments, the data obtained and provided via the various components described herein may be presented to particular users such as service providers, technicians, and/or the like for the purposes of servicing, repairing, or setting up various components. For example, information pertaining to a last service date for a particular component, including what was completed, and/or the like may be provided to a technician user, who can use the information to conduct a new service without having to refer to notes or information that may not be available (e.g., if the previous service was conducted by a different service provider that does not share service notes).

Figure 26:
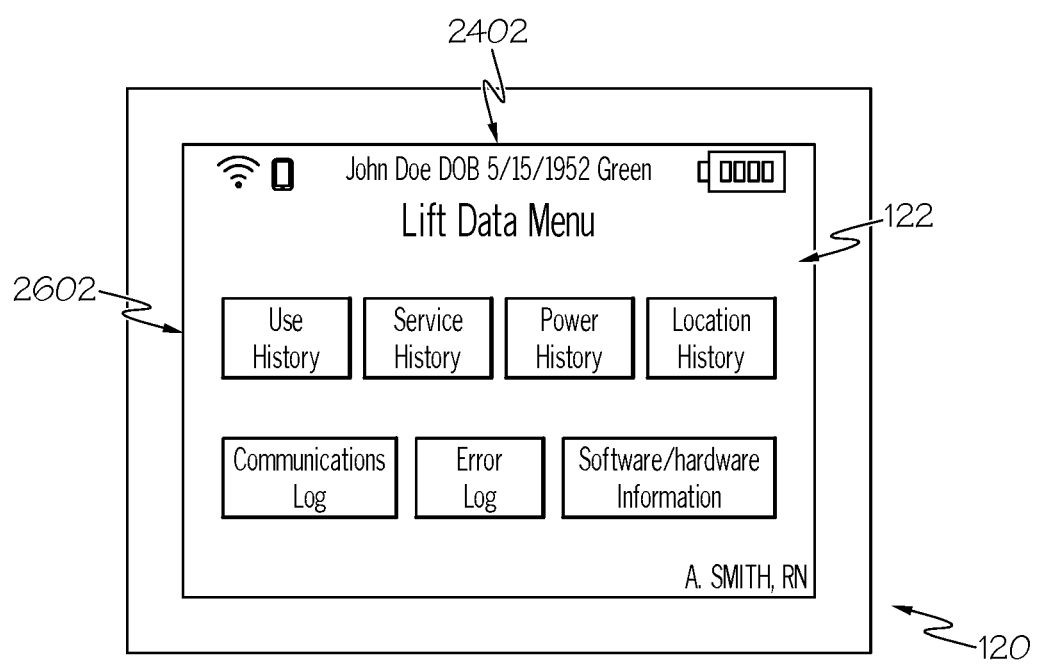
FIG. 26 schematically depicts a screen shot of a user interface on a wall-mounted control configured to display information pertaining to particular data obtained by the lift according to one or more embodiments shown and described herein.

FIG. 26 depicts one illustrative user interface displayed by the display 122 of the wall-mounted control 120 that may provide access to the above-mentioned data to a user. For example, as shown in FIG. 26, the display 122 may display a lift data menu that includes one or more data selection buttons 2602 pertaining to a particular user (e.g., the user indicated in the header information 2402), a particular component, and/or the like. Illustrative examples of the one or more data selection buttons 2602 include, but are not limited to, use history (a log of when the component has been used in the past, as well as details thereof), service history (a log of when the component has been serviced in the past, as well as details thereof), power history (e.g., charge/discharge profiles), location history, a communications log, an error log, and/or information pertaining to software and hardware components.

The various data may also be obtained by an administrator via one or more of the user interfaces described herein for the purposes of monitoring performance, tracking use, ensuring compliance with protocols, and/or the like. For example, if data pertaining to a movement history of a rail-mounted lift 100 and/or a mobile lift 100', a load on the lifting strap 108, and/or the like is provided to an administrator, along with data pertaining to the user that used the rail-mounted lift 100 and/or the mobile lift 100' and which subject was associated with the rail-mounted lift, the administrator can determine whether the user complied with protocol and/or regulations in operating the rail-mounted lift 100 and/or the mobile lift 100'.

In some embodiments, the data obtained by the various components described herein may also be used to automatically populate information into an electronic medical record (EMR) for a subject such that future access of the EMR is up-to-date with more detailed information than what is typically included in an EMR pertaining to rail-mounted lifts. This may be particularly useful in assessing future protocol for a particular subject, determining what has already been completed for a particular subject, and/or the like. As such, the data described herein may be outputted to an external device, such as a server containing EMR data.

Figure 27:
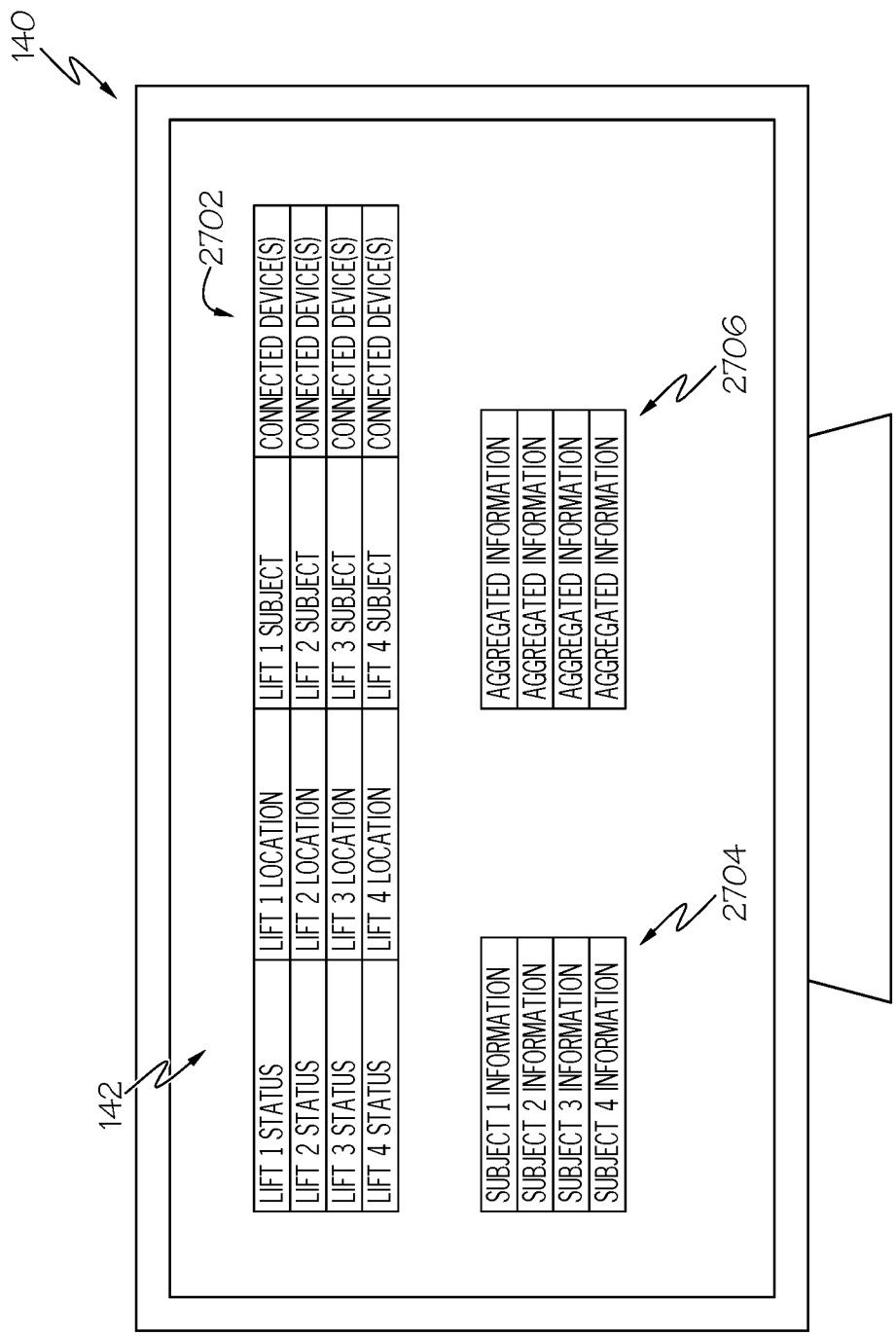
FIG. 27 schematically depicts a screen shot of an interface on a remote display pertaining to one or more lifts, one or more associated devices, one or more subjects, and/or aggregated information according to one or more embodiments shown and described herein.

In some embodiments, such information may be further available at the remote display 140, as depicted in FIG. 27. For example, the display component 142 may display lift/device information 2702 pertaining to one or more lifts and/or devices in a facility, including, but not limited to, the status of the components, the location of the components, associated subjects and/or users, and/or connected devices. The display component 142 may also display subject information 2704 pertaining to particular subjects, such as subjects that are supported by the lifts. Since the areas that the lift supports can be identified, the lift data that is presented via the display component 142 can be linked to the individual subject and other relevant subject data, such as the Banner Mobility Assessment Tool (BMAT), for that subject can also be presented along with the lift activities via the display component 142. Aggregated information 2706 pertaining to a plurality of subjects may also be displayed by the display component 142. In some embodiments, the information provided via the remote display 140 may reset at various intervals such that new information is provided. For example, the remote display 140 presentation of a number of lift activities may be reset at midnight or another time relevant to support the caregiver process in order to enable the caregiver to follow up on safe subject handling protocols.

In some embodiments, the display component 142 of the remote display 140 may show, for a particular period of time, a current number of lift activities since last reset, which, in some embodiments, may be mapped to a particular subject. Such information may provide a user (e.g., a caregiver or other individual following up on caregiver activities), an opportunity to instantly assess if the protocols for subject mobilization have been adhered to. For example, if a head nurse makes a round in the afternoon, he/she can instantly see on the remote display 140 if the lifts have been used or not that day and address possible issues with immobile subjects not being mobilized or mobilized without the aids available to support safe subject handling. Further, the information that is provided via the remote display 140 allows users (e.g., caregivers) to quickly glance at the remote display 140 to obtain information instead of having to take the time to access electronic medical records for a subject to view information.

It should now be understood that the present disclosure relates to a system of interconnected components that allows for a lift to be coupled to an untethered, wall-mounted control and/or a remote control and allows for data to be transmitted between the various components of the lift. The communications between the various components allow for pairing of lift units to particular components based on location, remote control of lift units, display of information that is at least partially from data transmitted from a lift unit, and/or the like.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A lift communications system comprising:
one or more lifts, each one of the one or more lifts being movable within a space; and
a wall-mounted control coupled to a wall of the space, the wall-mounted control configured to communicatively couple to the one or more lifts via a wireless connection,
wherein, when the wall-mounted control is communicatively coupled to a lift of the one or more lifts, the wall-mounted control is configured to direct operation of the lift, receive data from the lift, and provide, via a user interface, one or more movement controls based on potential movement parameters of the lift that are determined from the data.

2. The lift communications system of claim 1, further comprising:
a remote control communicatively coupled to the wall-mounted control, the remote control programmed to selectively operate the lift via the wall-mounted control.

3. The lift communications system of claim 1, further comprising:
a remote display communicatively coupled to at least one of the wall-mounted control and the one or more lifts, the remote display providing information pertaining to operation of the one or more lifts, wherein data pertaining to the operation is generated by the one or more lifts and transmitted to at least one of the wall-mounted control and the remote display.

4. The lift communications system of claim 1, further comprising a server computing device communicatively coupled to at least one of the wall-mounted control and the one or more lifts, the server computing device configured to store and provide information pertaining to operation of the one or more lifts.

5. The lift communications system of claim 1, wherein at least one of the one or more lifts is a rail-mounted lift.

6. The lift communications system of claim 1, wherein at least one of the one or more lifts is a mobile lift.

7. The lift communications system of claim 1, wherein each one of the one or more lifts are configured to communicatively couple to the wall-mounted control via a network.

8. The lift communications system of claim 1, wherein each of the one or more lifts are configured to communicatively couple to the wall-mounted control via a direct connection.

9. The lift communications system of claim 1, wherein each of the one or more lifts are configured to communicatively couple to the wall-mounted control via an access point.

10. A lift communications system comprising:
one or more lifts, each one of the one or more lifts being movable within a space;
a wall-mounted control coupled to a wall of the space, the wall-mounted control configured to communicatively couple to the one or more lifts via a wireless connection, wherein, when the wall-mounted control is communicatively coupled to a lift of the one or more lifts, the wall-mounted control is configured to direct operation of the lift;
a remote control communicatively coupled to the wall-mounted control, the remote control programmed to selectively operate the wall-mounted control; and
a remote display communicatively coupled to the wall-mounted control and the one or more lifts, the remote display providing information pertaining to operation of the one or more lifts,
wherein:
data pertaining to the operation of the one or more lifts is generated by the one or more lifts and is transmitted to the wall-mounted control and the remote display, and
the wall-mounted control provides, via a user interface, one or more movement controls based on potential movement parameters of the lift that are determined from the data.

11. The lift communications system of claim 10, further comprising a server computing device communicatively coupled to at least one of the wall-mounted control and the one or more lifts, the server computing device configured to store and provide information pertaining to operation of the one or more lifts.

12. The lift communications system of claim 10, wherein at least one of the one or more lifts is a rail-mounted lift.

13. The lift communications system of claim 10, wherein at least one of the one or more lifts is a mobile lift.

14. The lift communications system of claim 10, wherein each one of the one or more lifts are configured to communicatively couple to the wall-mounted control via a network.

15. The lift communications system of claim 10, wherein each of the one or more lifts are configured to communicatively couple to the wall-mounted control via a direct connection.

16. The lift communications system of claim 10, wherein each of the one or more lifts are configured to communicatively couple to the wall-mounted control via an access point.

17. The lift communications system of claim 1, wherein the wall-mounted control is battery powered and removable from a mount.

18. The lift communications system of claim 1, wherein the lift of the one or more lifts comprises a battery and the wall-mounted control is configured to display information relating to the battery based on the data from the lift.

19. The lift communications system of claim 1, wherein the user interface comprises controls for performing an emergency stop of the lift.

20. The lift communications system of claim 1, wherein the user interface comprises controls for resetting the lift.

* * * * *